United States Patent [19]

Nakamura et al.

[11] Patent Number: 5,849,217
[45] Date of Patent: Dec. 15, 1998

[54] OPTICALLY ACTIVE COMPOUND, LIQUID CRYSTAL COMPOSITION CONTAINING THE SAME, LIQUID CRYSTAL DEVICE USING THE SAME, LIQUID CRYSTAL APPARATUS AND DISPLAY METHOD

[75] Inventors: Shinichi Nakamura, Isehara; Takao Takiguchi, Tokyo; Takashi Iwaki, Machida; Takeshi Togano, Yokohama; Yoko Kosaka, Atsugi, all of Japan

[73] Assignee: Canon Kabushiki Kaisha, Tokyo, Japan

[21] Appl. No.: 748,971

[22] Filed: Nov. 13, 1996

Related U.S. Application Data

[63] Continuation of Ser. No. 371,854, Jan. 12, 1995, abandoned.

[30] Foreign Application Priority Data

| | | | | |
|---|---|---|---|---|
| Jan. 13, 1994 | [JP] | Japan | ...................................... | 6-014119 |
| May 9, 1994 | [JP] | Japan | ...................................... | 6-119597 |
| Dec. 27, 1994 | [JP] | Japan | ...................................... | 6-337062 |

[51] Int. Cl.$^6$ .......................... C09K 19/34; G02F 1/133; C07D 307/02; C07D 305/12
[52] U.S. Cl. ............................... 252/299.61; 252/299.62; 252/299.63; 319/182; 549/295; 549/313; 549/318; 549/320; 549/322; 549/323; 549/324
[58] Field of Search .................. 252/299.61, 299.62, 252/299.63; 349/182; 549/295, 313, 318, 320, 322, 323, 324

[56] References Cited

U.S. PATENT DOCUMENTS

| | | | |
|---|---|---|---|
| 4,367,924 | 1/1983 | Clark et al. ............................... | 350/334 |
| 4,973,425 | 11/1990 | Kazuhiko et al. ................. | 252/299.61 |
| 5,354,501 | 10/1994 | Nakamura et al. ................. | 252/299.62 |
| 5,385,692 | 1/1995 | Iwaki et al. ........................ | 252/299.62 |

FOREIGN PATENT DOCUMENTS

| | | |
|---|---|---|
| 0388141 | 9/1990 | European Pat. Off. . |
| 4322905 | 1/1994 | Germany . |
| 56-107216 | 8/1981 | Japan . |
| 2138274 | 5/1990 | Japan . |
| 2138385 | 5/1990 | Japan . |
| 2261893 | 10/1990 | Japan . |
| 2286673 | 11/1990 | Japan . |
| 2289561 | 11/1990 | Japan . |
| 3052882 | 3/1991 | Japan . |
| 3058981 | 3/1991 | Japan . |
| 3173878 | 7/1991 | Japan . |
| 3173879 | 7/1991 | Japan . |
| 4193872 | 7/1992 | Japan . |
| 4272989 | 9/1992 | Japan . |
| 4334376 | 11/1992 | Japan . |
| 5-59036 | 3/1993 | Japan . |

OTHER PUBLICATIONS

M. Jaladi et al, "A New preparation of furo–2, 3b furans, and conformational studies by 2D NMR", Tetrahedron Lett. vol. 24 (40) pp. 4307–4310, 1983.
CA 104: 88376, 1986.
CA 115 : 91933, 1991.
CA 121: 230420 1994.
M. Schadt & W. Helfrich, "Voltage—dependent optical activity of a twisted nematic liquid crystal", App. Phys. Lett. v. 18 n. 4 Feb. 15, 1971, pp. 127–128.

*Primary Examiner*—Shean C. Wu
*Attorney, Agent, or Firm*—Fitzpatrick, Cella, Harper & Scinto

[57] ABSTRACT

An optically active compound represented by the formula $R_1—A_1—A_2—X_1—A_3—(CH_2)_p—L—A_4—R_2$, in which $R_1$ is F, CN or straight chain, branched or cyclic alkyl and $R_2$ is H, F, CH or straight chain or branched alkyl; $A_3$ is 1,4-phenylene, pyridine-2,5-diyl, pyrimidine-2,5-diyl, pyrazine-2,5-diyl, pyridazine-3,6-diyl, 1,4-cyclohexylene, 1,3-dioxane-2,5-diyl, 1,3-ditiane-2,5-diyl, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2,6-diyl, quinoxaline-2,6-diyl, quinoline-2,6-diyl, 2,6-naphthylene, indane-2,5-diyl, 2-alkylindane-2,5-diyl, indanone-2,6-diyl, 2-alkylindane-2,6-diyl, coumarane-2,5-diyl and 2-alkylcoumarane-2,5-diyl; $A_1$, $A_2$ and $A_4$ are single bond or $A_3$; $X_1'$ is a single bond, —COO—, —OCO—, —$CH_2O$—, —$OCH_2$—, —$CH_2CH_2$—, —CH=CH— or —C≡C—; p is an integer from 2 to 20; and L is optically active.

25 Claims, 6 Drawing Sheets

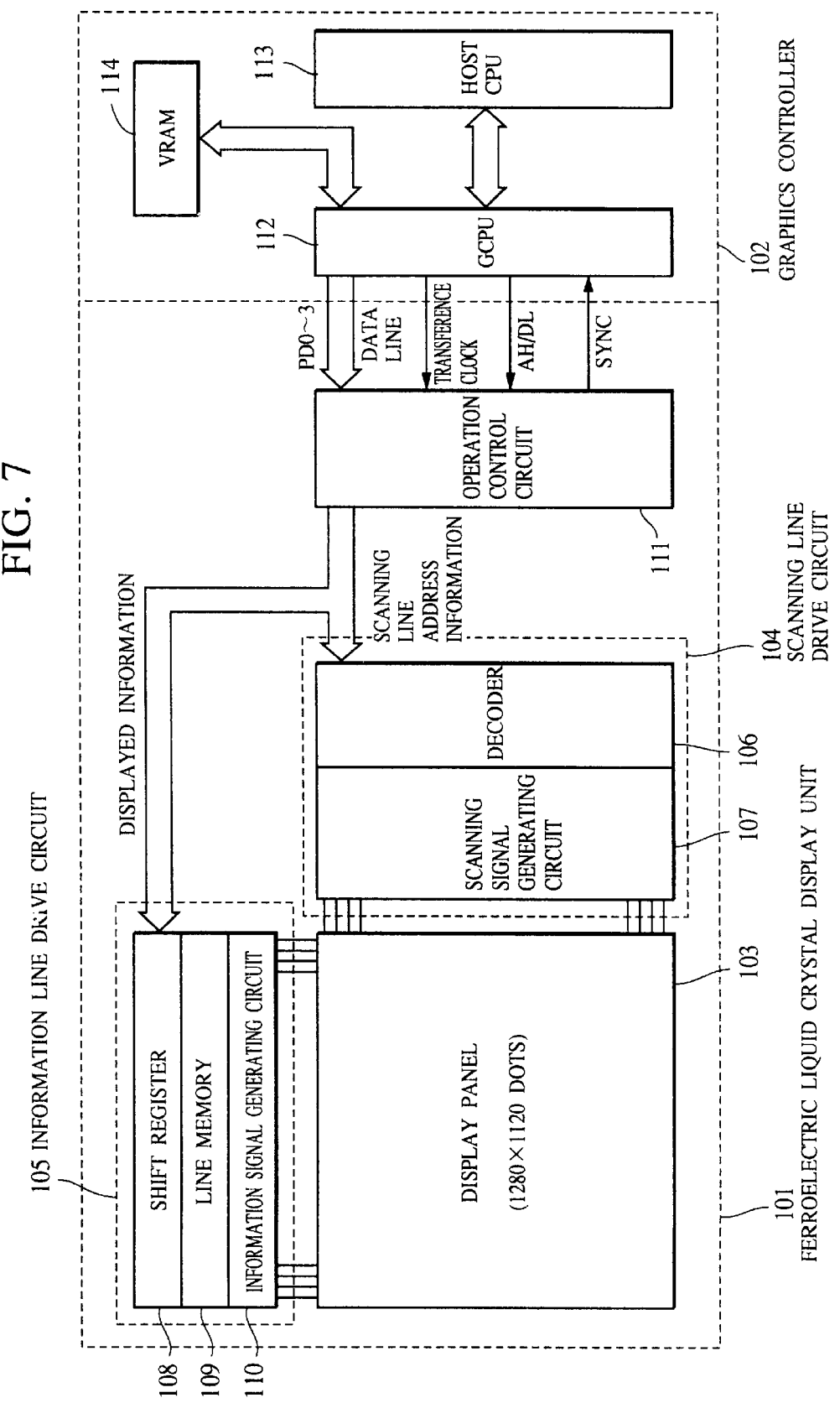

OPTICALLY ACTIVE COMPOUND, LIQUID CRYSTAL COMPOSITION CONTAINING THE SAME, LIQUID CRYSTAL DEVICE USING THE SAME, LIQUID CRYSTAL APPARATUS AND DISPLAY METHOD

This application is a continuation of application Ser. No. 08/371,854, filed Jan. 12, 1995, now abandoned.

BACKGROUND OF THE INVENTION

1. Field of the Invention

The present invention relates to a novel optically active compound, a liquid crystal composition containing the same, a liquid crystal device using the same and a liquid crystal apparatus. More particularly, the present invention relates, to a novel liquid crystal composition having an improved response characteristic with respect to an electric field, a liquid crystal display device using the same, a liquid crystal device for use in a liquid crystal-optical shutter and a display apparatus using the liquid crystal device to display information.

2. Related Background Art

Hitherto, liquid crystal has been used in a variety of industrial fields as an electro-optical device. A major portion of liquid crystal devices uses a TN (Twisted Nematic) type liquid crystal disclosed in, for example, "Voltage Dependent Optical Activity of a Twisted Nematic Liquid Crystal", M. Schadt and W. Helfrich, P.127 and P.128, Vol. 18, No. 4 (Feb. 15, 1971) of "Applied Physics Letters". The TN liquid crystal devices act on the basis of the dielectric arrangement effect of the liquid crystal, the effect being realized by the dielectric anisotropy of liquid crystal molecules such that the direction of the average molecular axis is oriented into a specific direction by the electric field. It has been said that the optical response speed of the TN liquid crystal devices is limited to milliseconds, the speed being unsatisfactory for a multiplicity of applications.

In view of application to a large size and plane display, operation using a simple matrix method is a most advantageous method to reduce the cost and realize a satisfactory manufacturing yield. The simple matrix method employs an electrode structure formed such that a scanning electrode group and a signal electrode group are arranged into a matrix configuration. To operate an electrode structure of the foregoing type, a time division operation method has been employed in which address signals are selectively, sequentially and periodically applied to the scanning electrode group; and predetermined information signals are selectively and in parallel applied to the signal electrode group in synchronization with the address signals.

However, employment of the TN type liquid crystal in the device operated by the foregoing method results in finite application of an electric field to a region (a so-called "semi-selected point") in which a scanning electrode is selected and as well as no signal electrode is selected or a region in which no scanning electrode is selected and as well as a signal electrode is selected. If the difference between voltage applied to the selected point and that applied to the semi-selected point is sufficiently large and if a voltage threshold required to orient liquid crystal molecules perpendicular to the electric field is set to an intermediate voltage between the foregoing voltages, the display device can be operated normally. If the number (N) of the scanning lines is increased, time (the duty ratio), in which an effective electric field is applied to one selected point, is shortened undesirably at a rate of 1/N during scanning the overall screen (one frame). Therefore, the difference between effective voltages respectively applied to the selected point and the non-selected point is reduced in inverse proportion to the number of the scanning lines. As a result, the contrast of the image is undesirably lowered and a problem of cross talk cannot be overcome.

The foregoing phenomenon takes place when liquid crystal having no bistability (the "stable state" is a state where liquid crystal molecules are oriented horizontally with respect to the surface of the electrode and liquid crystal molecules are oriented vertically only when the electric field is effectively applied) is operated by using a time accumulation effect (that is, scanned repeatedly). Therefore, the foregoing problem is an inherent problem that cannot be overcome.

To overcome the foregoing problem, a voltage averaging method, a two-frequency operation method and a multi-matrix method have been suggested, resulting in that a satisfactory effect has not been obtained. Therefore, any of the foregoing methods has been unsatisfactory and trends for enlarging the screen formed by the display devices and for raising the density have encountered limitations.

To overcome the problems experienced with the conventional liquid crystal device, use of a liquid crystal device having bistability has been suggested by Clark and Lagerwall (see Japanese Patent Laid-Open No. 56-107216 and U.S. Pat. No. 4,367,924).

As the bistable liquid crystal, ferroelectric liquid crystal having chiral smectic phase C (phase S*C) or phase H (phase S*H) is usually used. The ferroelectric liquid crystal has bistability with respect to an electric field, the bistability being consisting of a first optically stable state and a second optically stable state. Therefore, unlike the optically modulating devices for use in the foregoing conventional TN type liquid crystal, liquid crystal molecules are oriented in the first optically stable state with respect to either electric field vector and liquid crystal molecules are oriented in the second optically stable state with respect to another electric field. Furthermore, liquid crystal of the foregoing type has characteristics (bistability) of having either of the two stable states in response to the added electric field and as well as maintaining the foregoing state if no electric field is added.

The ferroelectric liquid crystal has an excellent characteristic of a high speed response as well as the bistability. The reason for this is that the spontaneous polarization of the ferroelectric liquid crystal and the applied electric field directly react with each other to induce transition of the state of orientation. As a result, the response speed is, by 3 to 4 orders, higher than that realized due to the reaction between the dielectric anisotropy and the electric field.

Since the ferroelectric liquid crystal latently has the excellent characteristics as described above, use of the characteristics enables the foregoing problems experienced with the conventional TN type device to be overcome substantially essentially. Therefore, applying of the ferroelectric liquid crystal to a high speed optical shutter and a high-density and large-size display is expected. Hence, liquid crystal materials having the ferroelectric characteristic have been widely studied. However, the ferroelectric liquid crystal materials, that have been developed, are unsatisfactory in terms of their characteristics required for the liquid crystal device including the operationality at low temperatures, high speed response and contrast.

In the ferroelectric liquid crystal, response time $\tau$, the intensity Ps of the spontaneous polarization and the viscosity η have the following relationship represented by the following equation (1):

$$\tau = \frac{\eta}{Ps \cdot E} \quad (1)$$

where E is an applied electric field.

Therefore, the response speed can be raised by any of the following methods:

(a) The intensity of the spontaneous polarization is raised.
(b) The viscosity η is reduced.
(c) The applied electric field E is enlarged.

However, the upper limit of the applied electric field is present because the ferroelectric liquid crystal is operated by an IC or the like. Therefore, it is preferable that the applied electric field is minimized. As a result, the viscosity η must be reduced or the intensity Ps of the spontaneous polarization must be enlarged. In general, ferroelectric chiral smectic liquid crystal compound having a large spontaneous polarization involves a trend of having a large internal electric field generated by the spontaneous polarization and therefore encounters a great limitation in allowable device structures which are capable of realizing the bistable state. If the spontaneous polarization is enlarged excessively, the viscosity is also raised, thus resulting in that the response speed cannot be raised as desired.

In a case where the actual temperature range for the display is about 5° C. to about 40° C., the response speed usually changes about 20 times which exceed the limit adjustable by changing the operation voltage and the frequency.

The liquid crystal device adapted to use the refractivity of liquid crystal usually has a transmissivity under a crossed-Nicol represented by the following equation (2):

$$\frac{I}{I_0} = \sin^2 4\theta_a \sin^2 \frac{\Delta nd}{\lambda} \pi \quad (2)$$

where $I_0$ is intensity of incidental light, I is intensity of transmissive light, $\theta_a$ is an apparent tilt angle defined later, Δn is anisotropy of the refractivity, d is the thickness of a liquid crystal layer and λ is the wavelength of incidental light. The tilt angle $\theta_a$ in the foregoing non-spiral structure is caused to appear as the angle of the direction of the average molecule axis of liquid crystal molecules twisted in the first and second states of orientation. According to equation (2), when the apparent tilt angle $\theta_a$ is 22.5°, the maximum transmissivity is made highest. Therefore, the apparent tilt angle $\theta_a$ in the non-spiral structure for realizing the bistability must be closer to 22.5°.

However, application to the non-spiral ferroelectric liquid crystal disclosed by Clark and Lagerwall and having bistability raises the following problems that undesirably lower the contrast.

First, since the tilt angle $\theta_a$ (the half of an angle made by axes of molecules in the two stable states) in the conventional non-spiral ferroelectric liquid crystal formed by an orienting process using a polyimide film subjected to a rubbing process is smaller than the tilt angle (angle θ which is the half of the apex angle of a triangular prism to be described later) of the ferroelectric liquid crystal, the transmissivity is low. Second, although the contrast can be raised in a static state in which no electric field is applied, black images are undesirably lightened because liquid crystal molecules are fluctuated by a small electric field during the non-selected period in the matrix operation in a case where an image is displayed by applying a voltage.

As described above, to realize the ferroelectric liquid crystal device, a liquid crystal composition having a chiral smectic phase is required, which exhibits high speed response, the response speed of which does not considerably depend on temperatures and which has high contrast. Furthermore, uniform switching of the display, excellent visual angle characteristic, low temperature dependency and reduction of loads on the operating IC must be realized by making adequate the spontaneous polarization, chiral smectic pitch C, cholesteric pitch, temperature range, in which the liquid phase is realized, the optical anisotropy, tilt angle and the dielectric anisotropy.

SUMMARY OF THE INVENTION

Accordingly, an object of the present invention is to provide an optically active compound capable of attaining a large spontaneous polarization, having high speed response, capable of reducing the temperature dependency of the response speed and realizing high contrast so as to put into practice a chiral smectic liquid crystal device, in particular, a ferroelectric liquid crystal liquid crystal device, and also to a liquid crystal composition containing the same, in particular a chiral smectic liquid crystal composition, a liquid crystal apparatus, and a display method which uses the foregoing liquid crystal composition.

According to the present invention, there is provided an optically active compound comprising a structure represented by the following general formula (I):

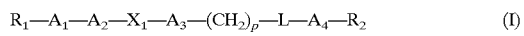

where $R_1$ and $R_2$ respectively are H, F, CN or straight chain, branched or cyclic alkyl group (one or more —$CH_2$— in the alkyl group may be replaced by —O—, —S—, —CO—, —CH(CN)—, —CH═CH— or —C≡C— under condition that hetero atoms do not position adjacent and the hydrogen atom in the alkyl group may be replaced by a fluorine atom) having 1 to 30 carbon atoms, $A_3$ is a group selected from the group consisting of 1, 4-phenylene, pyridine-2,5-diyl, pyrimidine-2,5-diyl, pyrazine-2,5-diyl, pyridazine-3,6-diyl, 1,4-cyclohexylene, 1,3-dioxane-2,5-diyl, 1,3-ditiane-2,5-diyl, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2,6-diyl, quinoxaline-2,6-diyl, quinoline-2,6-diyl, 2,6-naphthylene, indane-2,5-diyl, 2-alkylindane-2,5-diyl (the alkyl group is a straight chain or branched alkyl group having 1 to 18 carbon atoms), indanone-2,6-diyl, 2-alkylindane-2,6-diyl (the alkyl group is a straight chain or branched alkyl group having 1 to 18 carbon atoms), coumarane-2,5-diyl and 2-alkylcoumarane-2,5-diyl (the alkyl group is a straight chain or branched alkyl group having 1 to 18 carbon atoms), each of which may be substituted by at least one substituent selected from the group consisting of F, Cl, Br, $CH_3$, $CF_3$ and CN, $A_1$, $A_2$ and $A_4$ are single bonds or selected from $A_3$, $X_1$ is a single bond, —COO—, —OCO—, —$CH_2O$—, —$OCH_2$—, —$CH_2CH_2$—, —CH═CH— or —C≡C—, p is an integer from 2 to 20, L is optically active butanolyde-2,4-diyl or optically active 4-alkylbutanolyde-2,4-diyl (the alkyl group is straight-chain or branched alkyl group having 1 to 5 carbon atoms) or optically active 2-alkylbutanolyde-2,4-diyl (the alkyl group is straight-chain or branched alkyl group having 1 to 5 carbon atoms).

According to another aspect of the present invention, there is provided a liquid crystal composition containing one or more kinds of the optically active compounds as an essential component.

According to further aspect of the present invention, there are provided a liquid crystal device having the foregoing liquid crystal composition disposed between a pair of electrode substrates, a liquid crystal apparatus having the liquid crystal device, in particular, a display apparatus, and a display method for displaying information by controlling the foregoing liquid crystal composition.

Other and further objects, features and advantages of the invention will be evident from the following detailed description of the preferred embodiments in conjunction with the attached drawings.

BRIEF DESCRIPTION OF THE DRAWINGS

FIG. 7 is a block diagram which illustrates a liquid crystal display apparatus having a chiral smectic liquid crystal device according to the present invention and a graphic controller.

DESCRIPTION OF THE PREFERRED EMBODIMENTS

Figure 1:
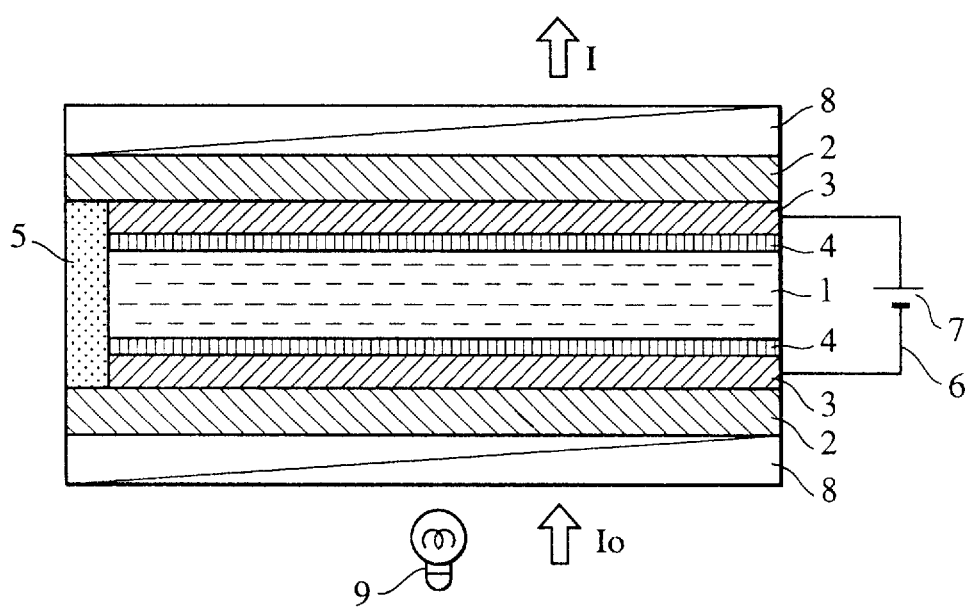
FIG. 1 is a schematic cross sectional view which illustrates an example of a liquid crystal device using liquid crystal having a chiral smectic phase according to the present invention.

Preferred embodiments of the present invention will now be described.

In an optically active compound according to the present invention and represented by chemical formula (I), $R_1$, $R_2$, $A_1$, $A_2$, $A_3$, $A_4$, $X_1$, L and p may be combined within the aforesaid range. Although preferred combinations will be described, individual combinations of the described materials are suitably selected.

Among the optically active compounds represented by general formula (I), a compound satisfying any of requirements (Ia) to (Id) is preferably exemplified in the view points of the temperature range for the liquid crystal phase, miscibility, viscosity and orienting characteristic. (Ia) An optically active compound in which $A_1$ and $A_2$ are respectively single bonds or a group selected from the group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, $CH_3$, $CF_3$ and CN, $A_3$ is 1,4-phenylene, which may be substituted by one or more substituent selected from a group consisting of F, Cl, Br, $CH_3$, $CF_3$ or CN and $A_4$ is a single bond.

(Ib) An optically active compound in which $A_1$ and $A_2$ are respectively single bonds or 1,4-phenylene, which may be substituted by at least one substituent selected from the group consisting of F, Cl, Br, $CH_3$, $CF_3$ and CN, $A_3$ is a material selected from a group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl or coumarane-2,5-diyl and $A_4$ is a single bond.

(Ic) An optically active compound in which $A_1$ is a single bond, $A_2$ and $A_4$ are respectively groups selected from the group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, $CH_3$, $CF_3$ and CN, and $A_3$ is 1,4-phenylene, which may be substituted by at least one substituent selected from the group consisting of F, Cl, Br, $CH_3$, $CF_3$ and CN.

(Id) An optically active compound in which $A_1$ is a single bond, $A_2$ is a single bond or 1,4-phenylene, which may be substituted by at least one substituent selected from the group consisting of F, Cl, Br, $CH_3$, $CF_3$ and CN, $A_3$ is a group selected from the group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl and $A_4$ is 1,4-phenylene, each of which may be substituted by at least one substituent selected from the group consisting of F, Cl, Br, $CH_3$, $CF_3$ and CN.

Further preferred compounds are the following compounds that satisfy any of the following requirements (Iaa to Idb):

(Iaa) An optically active compound in which $A_1$, $A_2$, $A_4$ and $X_1$ are respectively single bonds, and $A_3$ is 1,4-phenylene, which may be substituted by at least one substituent selected from the group consisting of F, Cl, Br, $CH_3$, $CF_3$ and CN.

(Iab) An optically active compound in which $A_1$, $A_4$ and $X_1$ are single bonds, $A_2$ is a group selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, each of which may be substituted by at least one substituent selected from the group consisting of F, Cl, Br, $CH_3$, $CF_3$ and CN, and $A_3$ is 1,4-phenylene, which may be substituted by at least one substituent selected from the group consisting of F, Cl, Br, $CH_3$, $CF_3$ and CN.

(Iac) An optically active compound in which $A_4$ and $X_1$ are single bonds, $A_1$ is pyrimidine-2,5-diyl, $A_2$ and $A_3$ are 1,4-phenylene, which may be substituted by at least one substituent selected from the group consisting of F, Cl, Br, $CH_3$, $CF_3$ and CN.

(Iad) An optically active compound in which $A_4$ and $X_1$ are single bonds, $A_1$ and $A_2$ are groups selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl and indane-2,5-diyl, each of which may be substituted by at least one substituent selected from the group consisting of F, Cl, Br, $CH_3$, $CF_3$ and CN, and $A_3$ is 1,4-phenylene, which may be substituted by at least one substituent selected from the group consisting of F, Cl, Br, $CH_3$, $CF_3$ and CN.

(Iba) An optically active compound in which $A_1$, $A_2$, $A_4$ and $X_1$ are single bonds, $A_3$ is a group selected from the group consisting of pyridine-2,5-diyl, 1,4-cyclohexylene, quinoxaline-2,6-diyl, quinoline-2,6-diyl and 2,6-naphthylene.

(Ibb) An optically active compound in which $A_1$, $A_4$ and $X_1$ are single bonds, $A_2$ is 1,4-phenylene, which may be substituted by at least one substituent selected from the group consisting of F, Cl, Br, $CH_3$, $CF_3$ and CN, and $A_3$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, quinoxaline-2,6-diyl, quinoline-2,6-diyl and 2,6-naphthylene.

(Ica) An optically active compound in which $A_1$ and $X_1$ are single bonds, $A_2$ is a group selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, each of which may be substituted by at least one substituent selected from the group consisting of F, Cl, Br, $CH_3$, $CF_3$ and CN, and $A_3$ and $A_4$ 1,4-phenylene, which may be substituted by at least one substituent selected from the group consisting of F, Cl, Br, $CH_3$, $CF_3$ and CN.

(Ida) An optically active compound in which $A_1$ and $X_1$ are single bonds, $A_3$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, $A_2$ and $A_4$ are 1,4-phenylene, which may be substituted by at least one substituent selected from the group consisting of F, Cl, Br, $CH_3$, $CF_3$ and CN.

(Idb) An optically active compound in which $A_1$, $A_2$ and $X_1$ are single bonds, $A_3$ is a group selected from the group consisting of 1,4-phenylene, pyridine-2,5-diyl, 1,4-cyclohexylene, quinoxaline-2,6-diyl, quinoline-2,6-diyl and 2,6-naphthylene, which may be substituted by at least one substituent selected from the group consisting of F, Cl, Br, $CH_3$, $CF_3$ and CN, and $A_4$ is 1,4-phenylene, which may be substituted by at least one substituent selected from the group consisting of F, Cl, Br, $CH_3$, $CF_3$ and CN.

In a case where 1,4-phenylene having one or two substituents (F, Cl, Br, $CH_3$, $CF_3$ or CN) is contained in the optically active compound represented by general formula (I), preferred substituent is any of F, Cl, Br and $CF_3$, and more preferably F.

In the structure in general formula (I), L is usually optically active 4-butanolyde-2,4-diyl or optically active 4-alkyl-4-butanolyde-2,4-diyl (the alkyl group is straight-chain or branched alkyl group having 1 to 5 carbon atoms) or optically active 2-alkyl-4-butanolyde-2,4-diyl (the alkyl group is straight-chain or branched alkyl group having 1 to 5 carbon atoms).

$R_1$ and $R_2$ are selected from (i) to (xvi).

 (i)

 (ii)

 (iii)

 (iv)

$C_hF_{2h+1}(CH_2)_i-Y_1-$ (v)

$C_kF_{2k+1}(OC_2F_4)_wOCF_2CH_2O-$ (vi)

H (vii)

F (viii)

 (ix)

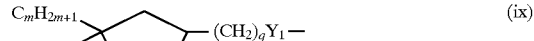 (x)

 (xi)

 (xii)

 (xiii)

 (xiv)

 (xv)

 (xvi)

where a is an integer from 1 to 16, d, g and i are integers from 0 to 7, b, e, h, j and k are integers from 1 to 10, f and w respectively are 0 or 1, m, n, q, r, s and t are integers from 0 and 10 in which $b+d \leq 16$, $e+f+g \leq 16$ and $h+i \leq 16$ are satisfied, E is $CH_3$ or $CF_3$, $Y_1$ is a single bond, —O—, —COO— or —OCO—, $Y_2$ is —COO—, —$CH_2$O—, —$CH_2CH_2$O—, —$CH_2CH_2CH_2$O— or —$CH_2CH_2$—, $Y_3$ is a single bond, —COO—, —$CH_2$O—O, —OCO— or —$OCH_2$ which may be optically active materials, and p is preferably an integer from 2 to 12, and further preferably an integer from 2 to 9.

The five-membered cyclic lacton-based compound serving as the optically active compound and a liquid crystal composition containing the same have been disclosed in Japanese Patent Laid-Open No. 2-138274, Japanese Patent Laid-Open No. 2-138385 (U.S. Pat. No. 4,973,425), Japanese Patent Laid-Open No. 2-261893, Japanese Patent Laid-Open No. 2-286673, Japanese Patent Laid-Open No. 2-289561, Japanese Patent Laid-Open No. 3-52882, Japanese Patent Laid-Open No. 3-58981, Japanese Patent Laid-Open No. 3-173878, Japanese Patent Laid-Open No. 3-173879, Japanese Patent Laid-Open No. 4-193872 and Japanese Patent Laid-Open No. 4-334376. However, the foregoing compounds have a structure that the linking portion of the lactone ring and that of the mesogen skeleton are bonded with a methyleneoxy group or a single bond and no disclosure has been made about the compound according to the present invention in which the lactone ring is bonded by an alkylene bond. Furthermore, no description has been made about the characteristics and effects of the compound according to the present invention. According to the present invention, there is provided a novel optically active five-membered cyclic lactone compound characterized in that the lactone ring and the mesogen skeleton are bonded with each other by the alkylene bond which is flexible and attains low viscosity. The present invention is structured based on a knowledge that the foregoing compound is capable of attaining a large spontaneous polarization, having high speed response, capable of reducing the temperature dependency of the response speed and realizing high contrast.

As the optically active compound represented by general formula (I), it is particularly preferable that a compound specifically represented by the following general formula (I') is employed:

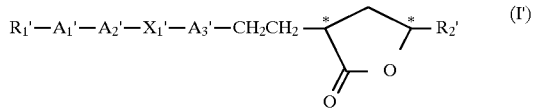

(I')

where $R_1'$ is H, F, CN or a straight, branched or cyclic alkyl group (one or more —$CH_2$— in the alkyl group may he replaced by —O—, —S—, —CO—, —CH (CN)—, —CH=CH— or —C≡C— under condition that hetero atoms do not position adjacent and the hydrogen atom in the alkyl group may be replaced by a fluorine atom) having 1 to 20 carbon atoms, $R_2'$ is a straight or branched alkyl group (one or more —$CH_2$— in the alkyl group may be replaced by —O—, —CO— or —CH=CH— under condition that hetero atoms do not position adjacent and the hydrogen atom in the alkyl group may be replaced by a fluorine atom), $A_3'$ is a group selected from the group consisting of 1,4-phenylene, pyridine-2,5-diyl, pyrimidine-2,5-diyl, pyrazine-2,5-diyl, pyridazine-3,6-diyl, 1,4-cyclohexylene, 1,3-dioxane-2,5-diyl, 1,3-ditiane-2,5-diyl, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl, alkylindane-2,5-diyl (the alkyl group is a straight chain or branched alkyl group having 1 to 18 carbon atoms), indanone-2,6-diyl, 2-alkylindane-2,6-diyl (the alkyl group is a straight chain or branched alkyl group having 1 to 18 carbon atoms), coumarane-2,5-diyl and 2-alkylcoumarane-2,5-diyl (the alkyl group is a straight chain or branched alkyl group having 1 to 18 carbon atoms), each of which may be substituted by at least one substituent selected from the group consisting of F, Cl, Br, $CH_3$, $CF_3$ and CN, $A_1'$ and $A_2'$ are respectively single bonds or selected from $A_3'$, $X_1'$ is a single bond, —COO—, —OCO—, —$CH_2O$—, —$OCH_2$—, —$CH_2CH_2$—, —CH=CH— or —C≡C—, and * represents optically active characteristic.

Among the optically active compounds represented by general formula (I'), it is preferable to employ a compound satisfying the following condition (Ia') or (Ib') in viewpoints of the temperature range for the liquid crystal phase, the mixing easiness, the viscosity and orienting easiness for the liquid crystal:

(Ia') An optically active compound in which $A_1'$ and $A_2'$ are single bonds or groups selected from the group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, $CH_3$, $CF_3$ and CN and $A_3$ is 1,4-phenylene, which may be substituted by at least one substituent selected from the group consisting of F, Cl, Br, $CH_3$, $CF_3$ and CN and $A_4$ is a single bond.

(Ib') An optically active compound in which $A_1'$ and $A_2'$ are single bonds or 1,4-phenylene, which may be substituted by at least one substituent selected from the group consisting of F, Cl, Br, $CH_3$, $CF_3$ and CN, $A_3'$ is a group selected from the group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl.

As the optically active compound represented by general formula (I'), it is preferable that any material represented by (Iaa') to (Ibb') be employed.

(Iaa') An optically active compound in which $A_1'$, $A_2'$ and $X_1'$ are single bonds and $A_3'$ is 1,4-phenylene, which may be at least one substituent selected from the group consisting of F, Cl, Br, $CH_3$, $CF_3$ and CN.

(Iab') An optically active compound in which $A_1'$ is a single bond and both of $A_2'$ and $A_3'$ are 1,4-phenylene, which may be at least one substituent selected from the group consisting of F, Cl, Br, $CH_3$, $CF_3$ and CN.

(Iac') An optically active compound in which $A_1'$ and $X_1'$ are single bonds, $A_2'$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, $A_3'$ is 1,4-phenylene, which may be substituted by at least one substituent selected from the group consisting of F, Cl, Br, $CH_3$, $CF_3$ and CN.

(Iba') An optically active compound in which $A_1'$, $A_2'$ and $X_1'$ are single bonds and $A_3'$ is a group selected from the group consisting of pyridine-2,5-diyl, 1,4-cyclohexylene, quinoxaline-2,6-diyl, quinoline-2,6-diyl and 2,6-naphthylene.

(Ibb') An optically active compound in which $A_1'$ and $X_1'$ are single bonds, $A_2'$ is 1,4-phenylene, which may be substituted by at least one substituent selected from the group consisting of F, Cl, Br, $CH_3$, $CF_3$ and CN and $A_3'$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, quinoxaline-2,6-diyl, quinoline-2,6-diyl and 2,6-naphthylene.

In the optically active compound represented by general formula (I'), it is preferable that $R_1'$ and $R_2'$ are materials selected from a group consisting of (i') to (v').

$$n\text{-}C_{a'}H_{2a'+1}-Y_1'-\quad\quad\quad (i')$$

$$C_{b'}H_{2b'+1}\underset{|}{\overset{CH_3}{CH}}(CH_2)_{d'}-Y_1'-\quad\quad\quad (ii')$$

$$C_{e'}H_{2e'+1}O(CH_2)_{f'}\underset{|}{\overset{CH_3}{CH}}(CH_2)_{g'}-Y_1'-\quad\quad\quad (iii')$$

$$C_{j'}H_{2j'+1}\underset{|}{\overset{F}{CH}}-Y_2'-\quad\quad\quad (iv')$$

$$C_{h'}F_{2h'+1}(CH_2)_{i'}-Y_1'-\quad\quad\quad (v')$$

where a' is an integer from 1 to 16, d', g' and i' respectively are integers from 0 to 7, b', e', h' and j' respectively are integers from 1 to 10, f' is 0 or 1 in which $b'+d' \leq 16$, $e'+f'+g' \leq 16$ and $h'+i' \leq 16$ are satisfied, $Y_1'$ is a single bond, —O—, —COO— or —OCO— and $Y_2'$ is —COO— or —CH$_2$O—, which may be optically active.

The optically active compound according to the present invention can be prepared by a method in which a lactone ring is formed in the final stage thereof and which is exemplified by a method (A) having the steps of converting an alcohol into tosyl so as to be prepared into a malonic acid derivative; and causing it to react with an optically active oxirane and a method (B) having the steps of coupling oxirane having a olefin terminal with 9-BBN; and causing it to react with a derivative of a malonic acid. The optically active compound can be prepared by forming the lactone ring and by subjecting it to a coupling reaction (preparation examples (C) and (D)).

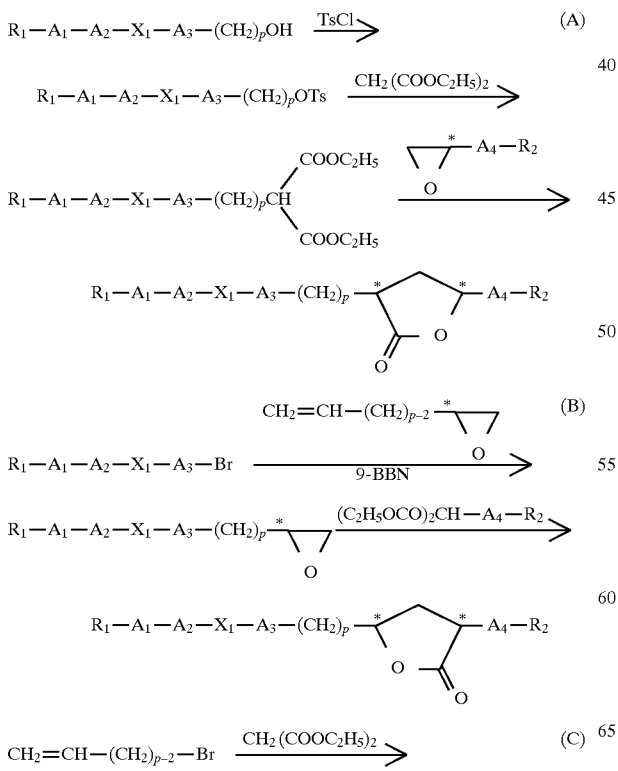

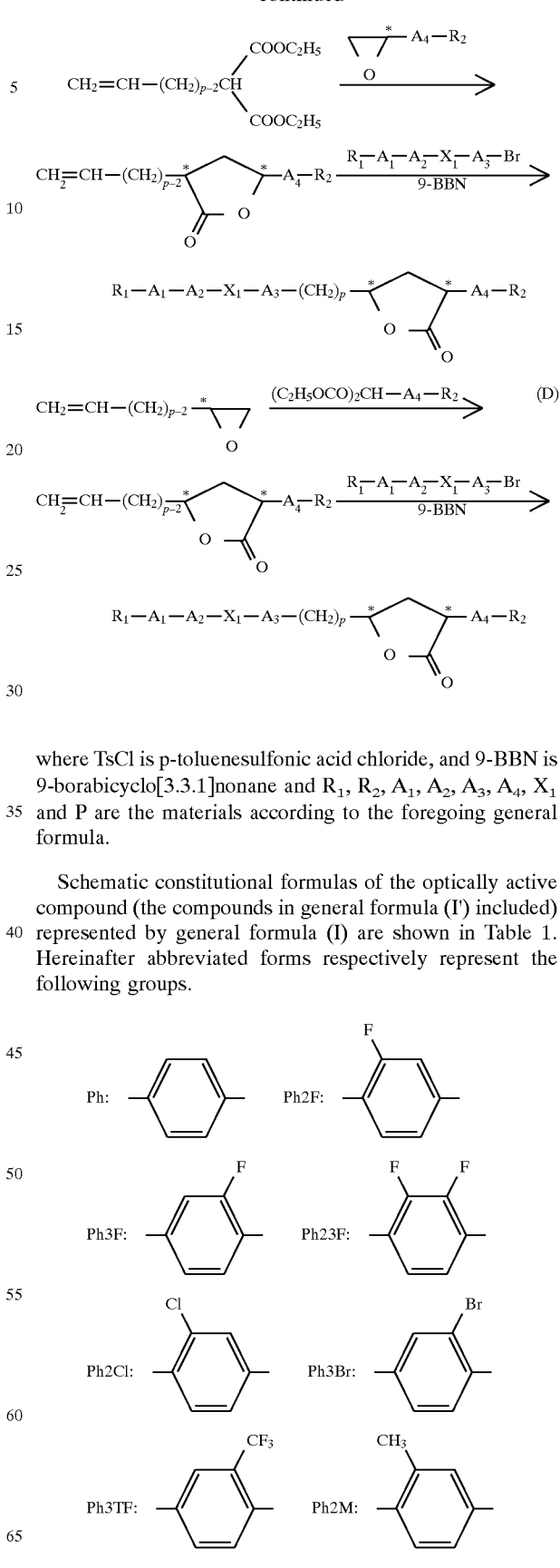

where TsCl is p-toluenesulfonic acid chloride, and 9-BBN is 9-borabicyclo[3.3.1]nonane and $R_1$, $R_2$, $A_1$, $A_2$, $A_3$, $A_4$, $X_1$ and P are the materials according to the foregoing general formula.

Schematic constitutional formulas of the optically active compound (the compounds in general formula (I') included) represented by general formula (I) are shown in Table 1. Hereinafter abbreviated forms respectively represent the following groups.

Ph2CN: 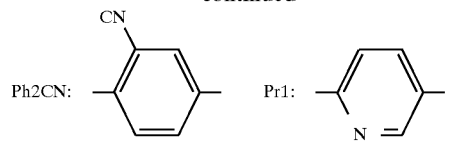 Pr1: 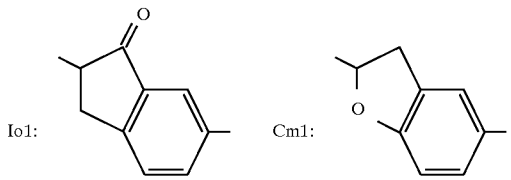
Pr2: 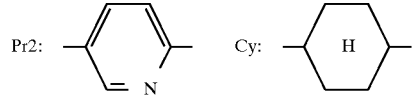 Cy:
Py1: 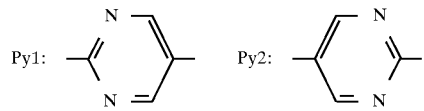 Py2:
Pa: 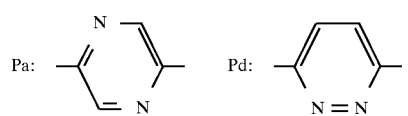 Pd:
Dt2: 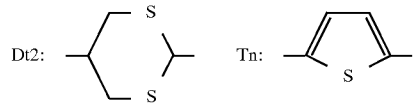 Tn:
Tz1:  Tz2:
Td: 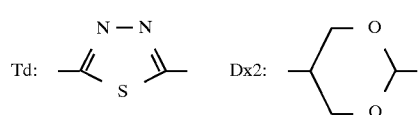 Dx2:
Boa2: 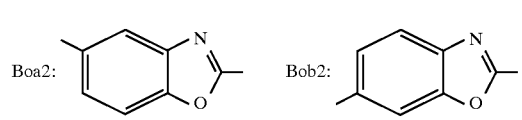 Bob2:
Bta2: 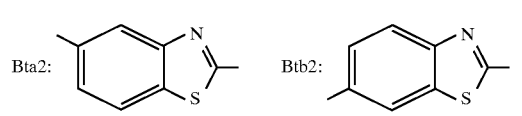 Btb2:
Np: 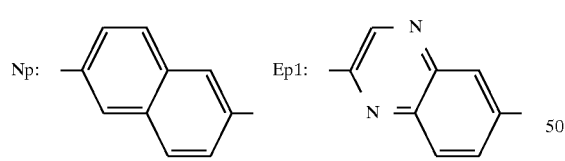 Ep1:
Ep2: 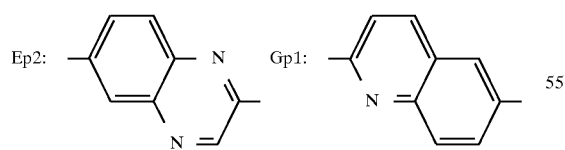 Gp1:
Gp2: 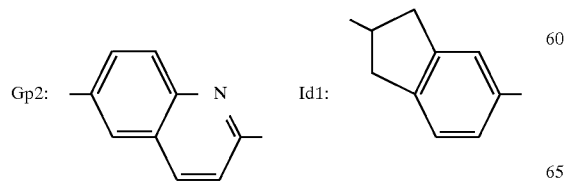 Id1:
Io1: 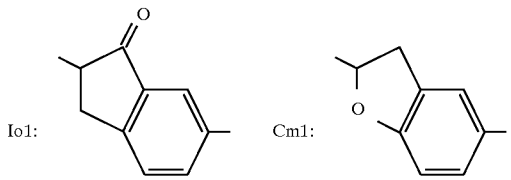 Cm1:
Ha2: 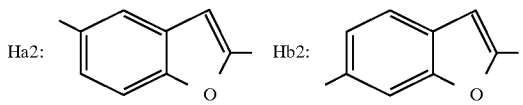 Hb2:
L1: 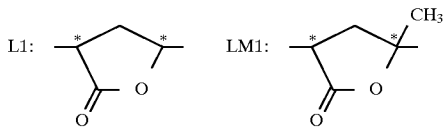 LM1:
L2: 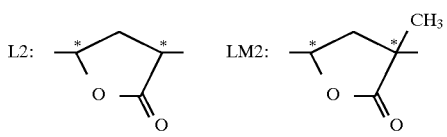 LM2:
Ox (t): 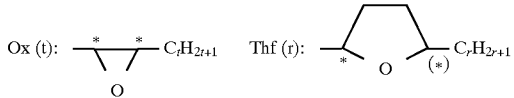 Thf (r):
Dp (s): 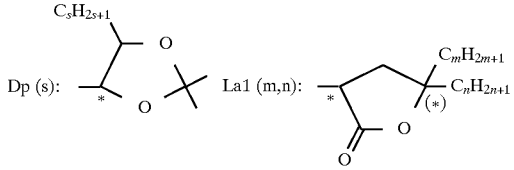 La1 (m,n):
La2 (m,n): 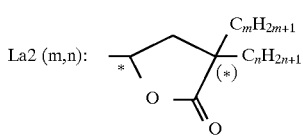
Lc1 (m,n): 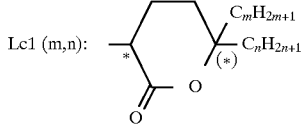
Lc2 (m,n): 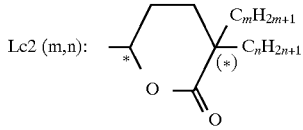 Pla: 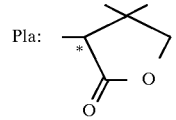

TABLE 1

| No. | R₁ | A₁ | A₂ | X₁ | A₃ | p | L | A₄ | R₂ |
|---|---|---|---|---|---|---|---|---|---|
| 1 | $C_6H_{13}$ | — | — | — | Ph | 2 | L1 | — | $C_8H_{17}$ |
| 2 | $C_8H_{17}O$ | — | — | — | Ph | 2 | L1 | — | $C_{18}H_{37}$ |
| 3 | $C_5H_{11}O$ | — | — | — | Ph2F | 2 | L1 | — | $C_6H_{13}$ |
| 4 | $CH_3O$ | — | Ph | — | Ph | 2 | L1 | — | $C_6H_{13}$ |
| 5 | $C_6H_{13}'CHF(CH_2)_2O$ | — | Ph | — | Ph | 2 | L1 | — | $C_6H_{13}$ |
| 6 | $C_7H_{15}O$ | — | Ph | — | Ph23F | 2 | L1 | — | $C_6H_{13}$ |
| 7 | $C_6H_{13}$ | — | Ph | —$OCH_2$— | Ph | 2 | L1 | — | $C_9H_{19}$ |
| 8 | $C_6F_{13}CH_2O$ | — | Ph | —C≡C— | Ph | 2 | L1 | — | $C_5H_{11}$ |
| 9 | $C_8H_{17}O$ | — | Ph | —COO— | Ph | 2 | L1 | — | $C_6H_{13}$ |
| 10 | $C_8H_{17}$ | — | Pr1 | — | Ph | 2 | L1 | — | $C_8H_{17}$ |
| 11 | $C_{10}H_{21}$ | — | Pr2 | — | Ph | 2 | L1 | — | $C_4H_9$ |
| 12 | $C_{11}H_{23}$ | — | Pr2 | — | Ph | 2 | L1 | — | $C_6H_{13}$ |
| 13 | $C_{12}H_{25}$ | — | Pr2 | —COO— | Ph | 2 | L1 | — | $C_8H_{17}$ |
| 14 | $C_4H_9O$ | — | Py1 | — | Ph | 2 | L1 | — | $C_{10}H_{21}$ |
| 15 | $C_{13}H_{27}$ | — | Py2 | — | Ph | 2 | L1 | — | $C_5H_{11}$ |
| 16 | $C_6H_{13}O$ | — | Py2 | — | Ph | 2 | L1 | — | $C_8H_{17}$ |
| 17 | $C_6H_{13}'CHFCH_2O$ | — | Py2 | — | Ph | 2 | L1 | — | $C_9H_{19}$ |
| 18 | $C_5H_{11}O$ | — | Py2 | — | Ph23F | 2 | L1 | — | $C_4H_9$ |
| 19 | $C_{10}H_{21}$ | — | Py2 | — | Ph | 2 | L1 | — | $C_6H_{13}$ |
| 20 | $C_8H_{17}$ | — | Py2 | — | Ph3F | 2 | L1 | — | $C_7H_{15}$ |
| 21 | $C_6H_{13}$ | — | Cy | — | Ph | 2 | L1 | — | $C_4H_8OC_4H_9$ |
| 22 | $C_7H_{15}OCO$ | — | Cy | — | Ph | 2 | L1 | — | $C_{14}H_{29}$ |
| 23 | $C_6H_{13}$ | — | Cy | —CH=CH— | Ph | 2 | L1 | — | $C_{10}H_{21}$ |
| 24 | $C_3H_7$ | — | Cy | —COO— | Ph | 2 | L1 | — | $C_6H_{13}$ |
| 25 | $C_5H_{11}$ | — | Pa | — | Ph | 2 | L1 | — | $C_8H_{17}$ |
| 26 | $C_{10}H_{21}$ | — | Pd | — | Ph | 2 | L1 | — | $C_6H_{13}$ |
| 27 | $C_6H_{13}$ | — | Dt2 | — | Ph | 2 | L1 | — | $(CH_2)_7CH=CH_2$ |
| 28 | $C_8H_{17}$ | — | Tn | — | Ph | 2 | L1 | — | $C_9H_{19}$ |
| 29 | $C_6H_{13}'CHFCH_2CH_2$ | — | Py2 | — | Ph | 2 | L1 | — | $C_6H_{13}$ |
| 30 | $C_5H_{11}$ | — | Tz1 | — | Ph | 2 | L1 | — | $C_8H_{17}$ |
| 31 | $C_9H_{19}O$ | — | Tz2 | — | Ph | 2 | L1 | — | $C_5H_{11}$ |
| 32 | $C_2H_5$ | — | Td | — | Ph | 2 | L1 | — | $C_8H_{17}$ |
| 33 | $C_{10}H_{21}$ | — | Dx2 | — | Ph | 2 | L1 | — | $C_7H_{15}$ |
| 34 | $C_6H_{13}$ | — | Boa2 | — | Ph | 2 | L1 | — | $C_{10}H_{21}$ |
| 35 | $C_7H_{15}$ | — | Bob2 | — | Ph | 2 | L1 | — | $C_6H_{13}$ |
| 36 | $C_{16}H_{33}O$ | — | Bta2 | — | Ph | 2 | L1 | — | $C_6H_{13}$ |
| 37 | $C_6H_{13}$ | — | Btb2 | — | Ph | 2 | L1 | — | $C_{14}H_{29}$ |
| 38 | $C_5H_{11}$ | — | Np | —COO— | Ph | 2 | L1 | — | $C_7H_{15}$ |
| 39 | $C_8H_{17}'CFHCH_2O$ | — | Ep1 | — | Ph | 2 | L1 | — | $C_{10}H_{21}$ |
| 40 | $C_4H_9$ | — | Ep2 | — | Ph | 2 | L1 | — | $C_6H_{13}$ |
| 41 | $C_6H_{13}$ | — | Gp1 | — | Ph | 2 | L1 | — | $C_{12}H_{25}$ |
| 42 | $C_7H_{15}$ | — | Gp2 | — | Ph | 2 | L1 | — | $C_6H_{13}$ |
| 43 | $C_6H_{13}$ | — | Cm1 | — | Ph | 2 | L1 | — | $C_8H_{17}$ |
| 44 | $C_8H_{17}$ | — | Io1 | — | Ph | 2 | L1 | — | $C_6H_{13}$ |
| 45 | $C_{20}H_{41}$ | — | Id1 | —COO— | Ph | 2 | L1 | — | $C_4H_9$ |
| 46 | $C_{11}H_{23}$ | — | Id1 | — | Ph | 2 | L1 | — | $C_8H_{17}$ |
| 47 | $C_8H_{17}$ | — | Id1 | — | Ph | 2 | L1 | — | $C_8H_{17}$ |
| 48 | $C_5H_{11}$ | — | Id1 | — | Ph2F | 2 | L1 | — | $C_6H_{13}$ |
| 49 | $C_6H_{13}$ | — | Tn | — | Ph | 2 | L1 | — | $C_7H_{15}$ |
| 50 | $C_4H_9O$ | — | Tz2 | — | Ph | 2 | L1 | — | $C_9H_{19}$ |
| 51 | $C_{12}H_{25}$ | — | Btb2 | — | Ph | 2 | L1 | — | $C_8H_{17}$ |
| 52 | $C_6H_{13}O$ | — | Btb2 | — | Ph | 2 | L1 | — | $C_9H_{19}$ |
| 53 | $CH_2=CH(CH_2)_3O$ | — | Ep2 | — | Ph | 2 | L1 | — | $C_6H_{13}$ |
| 54 | $C_9H_{19}$ | — | Gp2 | — | Ph | 2 | L1 | — | $C_5H_{11}$ |
| 55 | $C_5H_{11}O$ | — | Np | — | Ph | 2 | L1 | — | $C_{10}H_{21}$ |
| 56 | $C_6H_{13}$ | Ph | Ph | — | Ph | 2 | L1 | — | $C_3H_7$ |
| 57 | F | Pr2 | Ph | — | Ph | 2 | L1 | — | $C_6H_{13}$ |
| 58 | $C_3H_7$ | Py2 | Ph | — | Ph | 2 | L1 | — | $C_8H_{17}$ |
| 59 | $C_5H_{11}$ | — | Ha2 | — | Ph | 2 | L1 | — | $C_{11}H_{23}$ |
| 60 | $C_6H_{13}$ | Ph | Pr2 | — | Ph | 2 | L1 | — | $C_6H_{13}$ |
| 61 | $C_9H_{19}$ | Ph | Pr1 | — | Ph | 2 | L1 | — | $C_5H_{11}$ |
| 62 | $C_{13}H_{27}$ | Ph | Cy | — | Ph3Br | 2 | L1 | — | $C_7H_{15}$ |
| 63 | $C_{10}H_{21}O$ | Ph | Py1 | — | Ph | 2 | L1 | — | $C_6H_{13}$ |
| 64 | $C_7H_{15}$ | Ph | Py2 | — | Ph | 2 | L1 | — | $C_{10}H_{21}$ |
| 65 | $C_4H_9$ | Ph3TF | Pa | — | Ph | 2 | L1 | — | $(CH_2)_3CH(CH_3)_2$ |
| 66 | H | — | Hb2 | — | Ph | 2 | L1 | — | $C_8H_{17}$ |
| 67 | $C_8H_{17}$ | Ph | Tn | — | Ph | 2 | L1 | — | $C_5H_{11}$ |
| 68 | $C_2H_5$ | Ph | Tz1 | — | Ph2M | 2 | L1 | — | $C_3H_7$ |
| 69 | $C_6H_{13}$ | Ph | Tz2 | — | Ph | 2 | L1 | — | $C_6H_{13}$ |
| 70 | $C_{10}H_{21}$ | Ph | Td | — | Ph | 2 | L1 | — | $C_7H_{15}$ |
| 71 | $C_{10}H_{21}$ | — | Ph | — | Py1 | 2 | L1 | — | $C_6H_{13}$ |
| 72 | $C_6H_{13}$ | — | Ph | — | Py1 | 2 | L1 | — | $C_6H_{13}$ |
| 73 | $C_6H_{13}OCO$ | — | Ph | — | Py1 | 2 | L1 | — | $C_5H_{11}$ |
| 74 | $C_7H_{15}$ | — | — | — | Pr2 | 2 | L1 | — | $C_{10}H_{21}$ |
| 75 | $C_9H_{19}$ | — | Ph | — | Pr2 | 2 | L1 | — | $C_8H_{17}$ |
| 76 | $C_3H_7$ | — | Ph | — | Pr2 | 2 | L1 | — | $C_6H_{13}$ |
| 77 | $C_5H_{11}O$ | — | — | — | Cy | 2 | L1 | — | $C_4H_9$ |

TABLE 1-continued

| No. | R₁ | A₁ | A₂ | X₁ | A₃ | p | L | A₄ | R₂ |
|---|---|---|---|---|---|---|---|---|---|
| 78 | C₄H₉ | — | Ph | —CH₂O— | Cy | 2 | L1 | — | C₇H₁₅ |
| 79 | C₁₂H₂₅ | — | Ph | — | Cy | 2 | L1 | — | C₃H₇ |
| 80 | C₆H₁₃C≡C | — | Ph | — | Pa | 2 | L1 | — | C₆H₁₃ |
| 81 | C₈H₁₇O | — | Ph | — | Pd | 2 | L1 | — | C₅H₁₁ |
| 82 | C₃H₇ | — | Ph2Cl | — | Tn | 2 | L1 | — | C₁₀H₂₁ |
| 83 | C₄H₉ | — | Ph | — | Tn | 2 | L1 | — | C₇H₁₅ |
| 84 | C₈H₁₇ | — | Ph | — | Tz1 | 2 | L1 | — | C₁₂H₂₅ |
| 85 | C₄H₉OCH(CH₃)COO | — | Ph | — | Tz1 | 2 | L1 | — | C₅H₁₁ |
| 86 | C₆H₁₃ | — | Ph2F | — | Td | 2 | L1 | — | (CH₂)₃CH(CH₃)C₆H₁₃ |
| 87 | C₅H₁₁ | — | — | — | Np | 2 | L1 | — | C₉H₁₉ |
| 88 | C₈H₁₇OCH₂CH₂ | — | Ph | — | Np | 2 | L1 | — | C₅H₁₁ |
| 89 | C₁₁H₂₃ | — | Ph | — | Np | 2 | L1 | — | C₆H₁₃ |
| 90 | C₅H₁₁ | — | — | — | Ep1 | 2 | L1 | — | C₄H₉ |
| 91 | CH₃ | — | Ph | — | Ep1 | 2 | L1 | — | C₇H₁₅ |
| 92 | C₆H₁₃ | — | Ph | — | Ep1 | 2 | L1 | — | C₆H₁₃ |
| 93 | C₉H₁₉O | — | — | — | Gp1 | 2 | L1 | — | C₈H₁₇ |
| 94 | C₈H₁₇ | — | Ph | — | Gp1 | 2 | L1 | — | C₁₀H₂₁ |
| 95 | C₃H₇COO | — | Ph | — | Gp1 | 2 | L1 | — | C₁₁H₂₃ |
| 96 | C₄H₉ | — | Ph | — | Id1 | 2 | L1 | — | C₇H₁₅ |
| 97 | C₁₂H₂₅ | — | Ph | — | Io1 | 2 | L1 | — | C₆H₁₃ |
| 98 | C₁₀H₂₁ | — | Ph | — | Cm1 | 2 | L1 | — | C₅H₁₁ |
| 99 | C₆H₁₃ | — | Ph | — | Ph | 2 | L1 | — | (CH₂)₄C₃F₇ |
| 100 | C₃H₇ | Ph | Ph | — | Py1 | 2 | L1 | — | C₇H₁₅ |
| 101 | C₄H₉ | Ph2CN | Ph | — | Pr1 | 2 | L1 | — | C₄H₉ |
| 102 | C₅H₁₁ | Ph | Ph3F | — | Tz1 | 2 | L1 | — | C₃H₇ |
| 103 | CN | Ph | Ph | — | Tn | 2 | L1 | — | CH₃ |
| 104 | C₇H₁₅ | Tn | Ph | — | Py1 | 2 | L1 | — | C₈H₁₇ |
| 105 | C₁₀H₂₁ | Ph | Ph | — | Cy | 2 | L1 | — | C₆H₁₃ |
| 106 | C₆H₁₃ | — | — | — | Ph | 8 | L1 | — | C₈H₁₇ |
| 107 | C₈H₁₇O | — | — | — | Ph | 12 | L1 | — | C₁₈H₃₇ |
| 108 | C₅H₁₁O | — | — | — | Ph2F | 4 | L1 | — | C₆H₁₃ |
| 109 | CH₃O | — | Ph | — | Ph | 3 | L1 | — | C₆H₁₃ |
| 110 | C₆H₁₃'CHF(CH₂)₂O | — | Ph | — | Ph | 4 | L1 | — | C₆H₁₃ |
| 111 | C₇H₁₅O | — | Ph | — | Ph23F | 6 | L1 | — | C₆H₁₃ |
| 112 | C₆H₁₃ | — | Ph | —OCH₂— | Ph | 11 | L1 | — | C₉H₁₉ |
| 113 | C₆F₁₃CH₂O | — | Pu | —C≡C— | Ph | 4 | L1 | — | C₅H₁₁ |
| 114 | C₈H₁₇O | — | Ph | —COO— | Ph | 6 | L1 | — | C₆H₁₃ |
| 115 | C₈H₁₇ | — | Pr1 | — | Ph | 5 | L1 | — | C₈H₁₇ |
| 116 | C₁₀H₂₁ | — | Pr2 | — | Ph | 4 | L1 | — | C₄H₉ |
| 117 | C₁₁H₂₃ | — | Pr2 | — | Ph | 8 | L1 | — | C₆H₁₃ |
| 118 | C₁₂H₂₅ | — | Pr2 | —COO— | Ph | 10 | L1 | — | C₈H₁₇ |
| 119 | C₄H₉O | — | Py1 | — | Ph | 9 | L1 | — | C₁₀H₂₁ |
| 120 | C₁₃H₂₇ | — | Py2 | — | Ph | 7 | L1 | — | C₅H₁₁ |
| 121 | C₆H₁₃O | — | Py2 | — | Ph | 3 | L1 | — | C₈H₁₇ |
| 122 | C₆H₁₃'CHFCH₂CH₂ | — | Py2 | — | Ph | 4 | L1 | — | C₉H₁₉ |
| 123 | C₅H₁₁O | — | Py2 | — | Ph23F | 4 | L1 | — | C₄H₉ |
| 124 | C₁₀H₂₁ | — | Py2 | — | Ph | 6 | L1 | — | C₆H₁₃ |
| 125 | C₈H₁₇ | — | Py2 | — | Ph3F | 7 | L1 | — | C₇H₁₅ |
| 126 | C₈H₁₇ | — | Py2 | — | Ph | 4 | L1 | — | CH₂OC₆H₁₃ |
| 127 | C₁₀H₂₁ | — | Py2 | — | Ph | 8 | L1 | — | C₆H₁₃ |
| 128 | C₁₀H₂₁ | — | Py2 | — | Ph | 5 | L1 | — | C₆H₁₃ |
| 129 | C₃H₇ | — | Cy | —COO— | Ph | 6 | L1 | — | C₆H₁₃ |
| 130 | C₅H₁₁ | — | Pa | — | Ph | 4 | L1 | — | C₈H₁₇ |
| 131 | C₁₀H₂₁ | — | Pd | — | Ph | 7 | L1 | — | C₆H₁₃ |
| 132 | C₆H₁₃ | — | Dt2 | — | Ph | 9 | L1 | — | (CH₂)₅CH=CH₂ |
| 133 | C₈H₁₇ | — | Tn | — | Ph | 4 | L1 | — | C₉H₁₉ |
| 134 | C₅H₁₁ | — | Tz1 | — | Ph | 8 | L1 | — | C₈H₁₇ |
| 135 | C₉H₁₉O | — | Tz2 | — | Ph | 9 | L1 | — | C₅H₁₁ |
| 136 | C₂H₅ | — | Td | — | Ph | 8 | L1 | — | C₈H₁₇ |
| 137 | C₁₀H₂₁ | — | Dx2 | — | Ph | 5 | L1 | — | C₇H₁₅ |
| 138 | C₆H₁₃ | — | Boa2 | — | Ph | 4 | L1 | — | C₁₀H₂₁ |
| 139 | C₇H₁₅ | — | Bob2 | — | Ph | 6 | L1 | — | C₆H₁₃ |
| 140 | C₁₆H₃₃O | — | Bta2 | — | Ph | 4 | L1 | — | C₆H₁₃ |
| 141 | C₆H₁₃ | — | Btb2 | — | Ph | 6 | L1 | — | C₁₄H₂₉ |
| 142 | C₅H₁₁ | — | Np | —COO— | Ph | 4 | L1 | — | C₇H₁₅ |
| 143 | C₈H₁₇'CFHCH₂O | — | Ep1 | — | Ph | 6 | L1 | — | C₁₀H₂₁ |
| 144 | C₄H₉ | — | Ep2 | — | Ph | 8 | L1 | — | C₆H₁₃ |
| 145 | C₆H₁₃ | — | Gp1 | — | Ph | 12 | L1 | — | C₁₂H₂₅ |
| 146 | C₇H₁₅ | — | Gp2 | — | Ph | 7 | L1 | — | C₆H₁₃ |
| 147 | C₆H₁₃ | — | Cm1 | — | Ph | 4 | L1 | — | C₈H₁₇ |
| 148 | C₈H₁₇ | — | Io1 | — | Ph | 8 | L1 | — | C₆H₁₃ |
| 149 | C₂₀H₄₁ | — | Id1 | —COO— | Ph | 4 | L1 | — | C₄H₉ |
| 150 | C₁₁H₂₃ | — | Id1 | — | Ph | 9 | L1 | — | C₈H₁₇ |
| 151 | C₈H₁₇ | — | Id1 | — | Ph | 10 | L1 | — | C₈H₁₇ |
| 152 | C₅H₁₁ | — | Id1 | — | Ph2F | 3 | L1 | — | C₆H₁₃ |
| 153 | C₆H₁₃ | — | Tn | — | Ph | 4 | L1 | — | C₇H₁₅ |
| 154 | C₄H₉O | — | Tz2 | — | Ph | 6 | L1 | — | C₉H₁₉ |

TABLE 1-continued

| No. | R₁ | A₁ | A₂ | X₁ | A₃ | p | L | A₄ | R₂ |
|---|---|---|---|---|---|---|---|---|---|
| 155 | C₁₂H₂₅ | — | Btb2 | — | Ph | 8 | L1 | — | C₆H₁₃ |
| 156 | C₆H₁₃O | — | Btb2 | — | Ph | 7 | L1 | — | C₉H₁₉ |
| 157 | CH₂=CH(CH₂)₃O | — | Ep2 | — | Ph | 5 | L1 | — | C₆H₁₃ |
| 158 | C₉H₁₉ | — | Gp2 | — | Ph | 4 | L1 | — | C₅H₁₁ |
| 159 | C₅H₁₁O | — | Np | — | Ph | 4 | L1 | — | C₁₀H₂₁ |
| 160 | C₆H₁₃ | Ph | Ph | — | Ph | 6 | L1 | — | C₃H₇ |
| 161 | F | Pr2 | Ph | — | Ph | 8 | L1 | — | C₆H₁₃ |
| 162 | C₃H₇ | Py2 | Ph | — | Ph | 9 | L1 | — | C₈H₁₇ |
| 163 | C₅H₁₁ | — | Ha2 | — | Ph | 14 | L1 | — | C₁₁H₂₃ |
| 164 | C₆H₁₃ | Ph | Pr2 | — | Ph | 3 | L1 | — | C₆H₁₃ |
| 165 | C₉H₁₉ | Ph | Pr1 | — | Ph | 4 | L1 | — | C₅H₁₁ |
| 166 | C₁₃H₂₇ | Ph | Cy | — | Ph3Br | 6 | L1 | — | C₇H₁₅ |
| 167 | C₁₀H₂₁O | Ph | Py1 | — | Ph | 4 | L1 | — | C₆H₁₃ |
| 168 | C₇H₁₅ | Ph | Py2 | — | Ph | 6 | L1 | — | C₁₀H₂₁ |
| 169 | C₄H₉ | Ph3TF | Pa | — | Ph | 6 | L1 | — | (CH₂)₃CH(CH₃)₂ |
| 170 | H | — | Hb2 | — | Ph | 8 | L1 | — | C₈H₁₇ |
| 171 | C₈H₁₇ | Ph | Tn | — | Ph | 10 | L1 | — | C₅H₁₁ |
| 172 | C₂H₅ | Ph | Tz1 | — | Ph2M | 11 | L1 | — | C₃H₇ |
| 173 | C₆H₁₃ | Ph | Tz2 | — | Ph | 4 | L1 | — | C₆H₁₃ |
| 174 | C₁₀H₂₁ | Ph | Td | — | Ph | 4 | L1 | — | C₇H₁₅ |
| 175 | C₁₀H₂₁ | — | Ph | — | Py1 | 4 | L1 | — | C₆H₁₃ |
| 176 | C₆H₁₃ | — | Ph | — | Py1 | 5 | L1 | — | C₅H₁₃ |
| 177 | C₆H₁₃OCO | — | Ph | — | Py1 | 6 | L1 | — | C₅H₁₁ |
| 178 | C₇H₁₅ | — | — | — | Pr2 | 18 | L1 | — | C₁₀H₂₁ |
| 179 | C₉H₁₉ | — | Ph | — | Pr2 | 4 | L1 | — | C₈H₁₇ |
| 180 | C₃H₇ | — | Ph | — | Pr2 | 8 | L1 | — | C₆H₁₃ |
| 181 | C₅H₁₁O | — | — | — | Cy | 20 | L1 | — | C₄H₉ |
| 182 | C₄H₉ | — | Ph | —CH₂O— | Cy | 4 | L1 | — | C₇H₁₅ |
| 183 | C₁₂H₂₅ | — | Ph | — | Cy | 6 | L1 | — | C₃H₇ |
| 184 | C₆H₁₃C≡C | — | Ph | — | Pa | 5 | L1 | — | C₆H₁₃ |
| 185 | C₈H₁₇O | — | Ph | — | Pd | 7 | L1 | — | C₅H₁₁ |
| 186 | C₃H₇ | — | Ph2Cl | — | Tn | 13 | L1 | — | C₁₀H₂₁ |
| 187 | C₄H₉ | — | Ph | — | Tn | 4 | L1 | — | C₇H₁₅ |
| 188 | C₈H₁₇ | — | Ph | — | Tz1 | 6 | L1 | — | C₁₂H₂₅ |
| 189 | C₄H₉OCH(CH₃)COO | — | Ph | — | Tz1 | 4 | L1 | — | C₅H₁₁ |
| 190 | C₆H₁₃ | — | Ph2F | — | Td | 4 | L1 | — | (CH₂)₃CH(CH₃)C₆H₁₃ |
| 191 | C₅H₁₁ | — | — | — | Np | 6 | L1 | — | C₉H₁₉ |
| 192 | C₈H₁₇OCH₂CH₂ | — | Ph | — | Np | 6 | L1 | — | C₅H₁₁ |
| 193 | C₁₁H₂₃ | — | Ph | — | Np | 8 | L1 | — | C₆H₁₃ |
| 194 | C₅H₁₁ | — | — | — | Ep1 | 8 | L1 | — | C₄H₉ |
| 195 | CH₃ | — | Ph | — | Ep1 | 9 | L1 | — | C₇H₁₅ |
| 196 | C₆H₁₃ | — | Ph | — | Ep1 | 10 | L1 | — | C₆H₁₃ |
| 197 | C₉H₁₉O | — | — | — | Gp1 | 4 | L1 | — | C₈H₁₇ |
| 198 | C₈H₁₇ | — | Ph | — | Gp1 | 5 | L1 | — | C₁₀H₂₁ |
| 199 | C₃H₇COO | — | Ph | — | Gp1 | 7 | L1 | — | C₁₁H₂₃ |
| 200 | C₄H₉ | — | Ph | — | Id1 | 12 | L1 | — | C₇H₁₅ |
| 201 | C₁₂H₂₅ | — | Ph | — | Io1 | 4 | L1 | — | C₆H₁₃ |
| 202 | C₁₀H₂₁ | — | Ph | — | Cm1 | 4 | L1 | — | C₅H₁₁ |
| 203 | C₆H₁₃ | — | Ph | — | Ph | 6 | L1 | — | (CH₂)₄C₃F₇ |
| 204 | C₃H₇ | Ph | Ph | — | Py1 | 8 | L1 | — | C₇H₁₅ |
| 205 | C₄H₉ | Ph2CN | Ph | — | Pr1 | 7 | L1 | — | C₄H₉ |
| 206 | C₅H₁₁ | Ph | Ph3F | — | Tz1 | 4 | L1 | — | C₃H₇ |
| 207 | CN | Ph | Ph | — | Tn | 6 | L1 | — | CH₃ |
| 208 | C₇H₁₅ | Tn | Ph | — | Py1 | 4 | L1 | — | C₈H₁₇ |
| 209 | C₁₀H₂₁ | Ph | Ph | — | Cy | 4 | L1 | — | C₅H₁₃ |
| 210 | | | | | | | | | |
| 211 | C₆H₁₃ | — | — | — | Ph | 2 | L1 | Ph | H |
| 212 | C₈H₁₇O | — | — | — | Ph | 8 | L2 | Ph | OCH₃ |
| 213 | C₅H₁₁O | — | — | — | Ph2F | 2 | L1 | Ph2F | C₆H₁₃ |
| 214 | CH₃O | — | Ph | — | Ph | 4 | L2 | Ph | H |
| 215 | C₆H₁₃'CHF(CH₂)₂O | — | Ph | — | Ph | 2 | L1 | Ph | C₆H₁₃ |
| 216 | C₇H₁₅O | — | Ph | — | Ph23F | 2 | L1 | Ph | C₆H₁₃ |
| 217 | C₆H₁₃ | — | Ph | —OCH₂— | Ph | 4 | L1 | Ph | H |
| 218 | C₆F₁₃CH₂O | — | Ph | —C≡C— | Ph | 2 | L1 | Ph | C₅H₁₁ |
| 219 | C₈H₁₇O | — | Ph | —COO— | Ph | 7 | L2 | Pr1 | H |
| 220 | C₈H₁₇ | — | Pr1 | — | Ph | 7 | L2 | Ph | OCH₃ |
| 221 | C₁₀H₂₁ | — | Pr2 | — | Ph | 2 | L1 | Ph | H |
| 222 | C₁₁H₂₃ | — | Pr2 | — | Ph | 4 | L1 | Ph | C₆H₁₃ |
| 223 | C₁₂H₂₅ | — | Pr2 | —COO— | Ph | 8 | L2 | Ph | OC₆H₁₃ |
| 224 | C₄H₉O | — | Py1 | — | Ph | 2 | L1 | Cy | H |
| 225 | C₁₃H₂₇ | — | Py2 | — | Ph | 2 | L1 | Ph | C₅H₁₁ |
| 226 | C₆H₁₃O | — | Py2 | — | Ph | 6 | L2 | Ph | C₆H₁₃ |
| 227 | C₆H₁₃'CHFCH₂O | — | Py2 | — | Ph | 4 | L1 | Ph | H |
| 228 | C₅H₁₁O | — | Py2 | — | Ph23F | 2 | L1 | Ph | C₄H₉ |
| 229 | C₁₀H₂₁ | — | Py2 | — | Ph | 2 | L1 | Ph | H |
| 230 | C₈H₁₇ | — | Py2 | — | Ph3F | 2 | L1 | Ph | C₆H₁₃ |
| 231 | C₆H₁₃ | — | Cy | — | Ph | 4 | L2 | Ph | C₂H₄OC₄H₉ |
| 232 | C₈H₁₇OCO | — | Cy | — | Ph | 2 | L1 | Pd | H |

TABLE 1-continued

| No. | R₁ | A₁ | A₂ | X₁ | A₃ | p | L | A₄ | R₂ |
|---|---|---|---|---|---|---|---|---|---|
| 233 | C₆H₁₃ | — | Cy | —CH=CH— | Ph | 5 | L1 | Ph | OC₁₀H₂₁ |
| 234 | C₃H₇ | — | Cy | —COO— | Ph | 2 | L1 | Tz2 | H |
| 235 | C₅H₁₁ | — | Pa | — | Ph | 5 | L2 | Ph | C₈H₁₇ |
| 236 | C₁₀H₂₁ | — | Pd | — | Ph | 2 | L1 | Ph | OCH₃ |
| 237 | C₆H₁₃ | — | Dt2 | — | Ph | 6 | L2 | Ph | (CH₂)₅CH=CH₂ |
| 238 | C₈H₁₇ | — | Tn | — | Ph | 2 | L1 | Ph | H |
| 239 | C₅H₁₁ | — | Tz1 | — | Ph | 2 | L1 | Ph | H |
| 240 | C₆H₁₃'CHFCH₂CH₂ | — | Py2 | — | Ph | 4 | L1 | Py1 | H |
| 241 | C₉H₁₉O | — | Tz2 | — | Ph | 2 | L1 | Ph | C₆H₁₃ |
| 242 | C₂H₅ | — | Td | — | Ph | 2 | L2 | Ph | H |
| 243 | C₁₀H₂₁ | — | Dx2 | — | Ph | 4 | L2 | Ph | C₇H₁₅ |
| 244 | C₆H₁₃ | — | Boa2 | — | Ph | 2 | L1 | Ph | H |
| 245 | C₇H₁₅ | — | Bob2 | — | Ph | 2 | L1 | Ph | OCH₃ |
| 246 | C₁₆H₃₃O | — | Bta2 | — | Ph | 2 | L1 | Ph | H |
| 247 | C₆H₁₃ | — | Btb2 | — | Ph | 4 | L2 | Tn | C₁₄H₂₉ |
| 248 | C₅H₁₁ | — | Np | —COO— | Ph | 2 | L1 | Ph | H |
| 249 | C₈H₁₇'C(CF₃)HCH₂O | — | Ep1 | — | Ph | 2 | L1 | Ph | H |
| 250 | C₄H₉ | — | Ep2 | — | Ph | 2 | L1 | Ph | C₆H₁₃ |
| 251 | C₆H₁₃ | — | Gp1 | — | Ph | 6 | L2 | Ph | OCH₃ |
| 252 | C₇H₁₅ | — | Gp2 | — | Ph | 2 | L1 | Ph | H |
| 253 | C₆H₁₃ | — | Cm1 | — | Ph | 10 | L2 | Ph | C₆H₁₃ |
| 254 | C₈H₁₇ | — | Io1 | — | Ph | 4 | L1 | Ph | H |
| 255 | C₂₀H₄₁ | — | Id1 | —COO— | Ph | 2 | L1 | Ph | C₄H₉ |
| 256 | C₁₁H₂₃ | — | Id1 | — | Ph | 4 | L2 | Ph | H |
| 257 | C₈H₁₇ | — | Id1 | — | Ph | 2 | L1 | Ph | H |
| 258 | C₅H₁₁ | — | Id1 | — | Ph2F | 2 | L1 | Ph | C₆H₁₃ |
| 259 | C₆H₁₃ | — | Tn | — | Ph | 8 | L2 | Ph | C₇H₁₅ |
| 260 | C₄H₉O | — | Tz2 | — | Ph | 2 | L1 | Ph | C₉H₁₉ |
| 261 | C₁₂H₂₅ | — | Btb2 | — | Ph | 9 | L1 | Ph | H |
| 262 | C₆H₁₃O | — | Btb2 | — | Ph | 2 | L1 | Ph | C₆H₁₃ |
| 263 | CH₂=CH(CH₂)₅O | — | Ep2 | — | Ph | 7 | L2 | Ph | H |
| 264 | C₉H₁₉ | — | Gp2 | — | Ph | 2 | L1 | Ph | OCH₃ |
| 265 | C₅H₁₁O | — | Np | — | Ph | 2 | L1 | Np | C₁₀H₂₁ |
| 266 | C₆H₁₃ | Ph | Ph | — | Ph | 2 | L1 | Ph | C₃H₇ |
| 267 | F | Pr2 | Ph | — | Ph | 2 | L1 | Ph | H |
| 268 | C₃H₇ | Py2 | Ph | — | Ph | 7 | L1 | Ph | H |
| 269 | C₅H₁₁ | — | Ha2 | — | Ph | 7 | L2 | Ph | C₁₁H₂₃ |
| 270 | C₆H₁₃ | Ph | Pr2 | — | Ph | 4 | L2 | Ph | H |
| 271 | C₉H₁₉ | Ph | Pr1 | — | Ph | 2 | L1 | Ph | C₆H₁₃ |
| 272 | C₁₃H₂₇ | Ph | Cy | — | Ph3Br | 2 | L1 | Ph | C₇H₁₅ |
| 273 | C₁₀H₂₁O | Ph | Py1 | — | Ph | 2 | L1 | Ph | H |
| 274 | C₇H₁₅ | Ph | Py2 | — | Ph | 2 | L1 | Ph | C₁₀H₂₁ |
| 275 | C₄H₉ | Ph3TF | Pa | — | Ph | 6 | L2 | Ph | C₆H₁₃ |
| 276 | H | — | Hb2 | — | Ph | 2 | L1 | Ph | H |
| 277 | C₈H₁₇ | Ph | Tn | — | Ph | 4 | L1 | Ph3F | C₅H₁₁ |
| 278 | C₂H₅ | Ph | Tz1 | — | Ph2M | 2 | L1 | Ph | H |
| 279 | C₆H₁₃ | Ph | Tz2 | — | Ph | 8 | L2 | Ph | H |
| 280 | C₁₀H₂₁ | Ph | Td | — | Ph | 2 | LM1 | Ph | C₆H₁₃ |
| 281 | C₁₀H₂₁ | — | Ph | — | Py1 | 2 | L1 | Ph | H |
| 282 | C₆H₁₃ | — | Ph | — | Py1 | 3 | L2 | Ph | C₆H₁₃ |
| 283 | C₆H₁₃OCO | — | Ph | — | Py1 | 2 | L1 | Ph | H |
| 284 | C₇H₁₅ | — | — | — | Pr2 | 2 | L1 | Ph | C₆H₁₃ |
| 285 | C₉H₁₉ | — | Ph | — | Pr2 | 6 | L2 | Ph | H |
| 286 | C₃H₇ | — | Ph | — | Pr2 | 2 | L1 | Ph | OCH₃ |
| 287 | C₅H₁₁O | — | — | — | Cy | 6 | L1 | Ep1 | H |
| 288 | C₄H₉ | — | Ph | —CH₂O— | Cy | 2 | L1 | Ph | C₇H₁₅ |
| 289 | C₁₂H₂₅ | — | Ph | — | Cy | 4 | L2 | Ph | H |
| 290 | C₆H₁₃C≡C | — | Ph | — | Pa | 2 | L1 | Ph | H |
| 291 | C₈H₁₇O | — | Ph | — | Pd | 8 | L2 | Ph | C₅H₁₁ |
| 292 | C₃H₇ | — | Ph2Cl | — | Tn | 2 | L1 | Ph | H |
| 293 | C₄H₉ | — | Ph | — | Tn | 2 | L1 | Ph | H |
| 294 | C₈H₁₇ | — | Ph | — | Tz1 | 2 | L1 | Ph | H |
| 295 | C₄H₉OCH(CH₃)COO | — | Ph | — | Tz1 | 6 | L1 | Ph | C₅H₁₁ |
| 296 | C₆H₁₃ | — | Ph2F | — | Td | 2 | L1 | Ph | C₆H₁₃ |
| 297 | C₅H₁₁ | — | — | — | Np | 2 | L1 | Gp1 | H |
| 298 | C₈H₁₇OCH₂CH₂ | — | Ph | — | Np | 5 | L2 | Ph | C₅H₁₁ |
| 299 | C₁₁H₂₃ | — | Ph | — | Np | 2 | L1 | Ph | C₆H₁₃ |
| 300 | C₅H₁₁ | — | — | — | Ep1 | 2 | L1 | Ph | OC₄H₉ |
| 301 | CH₃ | — | Ph | — | Ep1 | 7 | L2 | Ph | C₇H₁₅ |
| 302 | C₆H₁₃ | — | Ph | — | Ep1 | 2 | L1 | Ph | H |
| 303 | C₉H₁₉O | — | — | — | Gp1 | 2 | L1 | Ph | C₆H₁₃ |
| 304 | C₈H₁₇ | — | Ph | — | Gp1 | 4 | L1 | Ph | H |
| 305 | C₃H₇COO | — | Ph | — | Gp1 | 8 | L2 | Ph | OCH₃ |
| 306 | C₄H₉ | — | Ph | — | Id1 | 2 | L1 | Ph | H |
| 307 | C₁₂H₂₅ | — | Ph | — | Io1 | 2 | L1 | Ph | C₆H₁₃ |
| 308 | C₁₀H₂₁ | — | Ph | — | Cm1 | 2 | L2 | Ph | H |
| 309 | C₆H₁₃ | — | Ph | — | Ph | 2 | L1 | Ph | C₆H₁₃ |

TABLE 1-continued

| No. | $R_1$ | $A_1$ | $A_2$ | $X_1$ | $A_3$ | p | L | $A_4$ | $R_2$ |
|---|---|---|---|---|---|---|---|---|---|
| 310 | $C_{10}H_{21}$ | — | Py2 | — | Ph | 2 | LM1 | — | $C_7H_{15}$ |
| 311 | $C_8H_{17}$ | — | Py2 | — | Ph | 4 | LM1 | — | $C_6H_{13}$ |
| 312 | $C_5H_{11}$ | — | Ph | — | Ph | 2 | LM1 | — | $C_5H_{11}$ |
| 313 | $C_6H_{13}$ | Py2 | Ph | — | Ph | 3 | LM1 | — | $C_8H_{17}$ |
| 314 | $C_7H_{15}$ | — | Ph | — | Ph | 6 | LM2 | — | $C_8H_{17}$ |
| 315 | $C_{10}H_{21}$ | Py2 | Ph | — | Ph | 2 | LM2 | — | $C_6H_{13}$ |
| 316 | $C_6H_{13}$ | — | — | — | Ph | 10 | L2 | — | $C_8H_{17}$ |
| 317 | $C_8H_{17}O$ | — | — | — | Ph | 8 | L2 | — | $C_{18}H_{37}$ |
| 318 | $C_5H_{11}O$ | — | — | — | Ph2F | 6 | L2 | — | $C_6H_{13}$ |
| 319 | $CH_3O$ | — | Ph | — | Ph | 4 | L2 | — | $C_6H_{13}$ |
| 320 | $C_5H_{11}'CHF(CH_2)_2O$ | — | Ph | — | Ph | 8 | L2 | — | $C_6H_{13}$ |
| 321 | $C_7H_{15}O$ | — | Ph | — | Ph23F | 12 | L2 | — | $C_6H_{13}$ |
| 322 | $C_6H_{13}$ | — | Ph | —$OCH_2$— | Ph | 4 | L2 | — | $C_9H_{19}$ |
| 323 | $C_6F_{13}CH_2O$ | — | Ph | —C≡C— | Ph | 6 | L2 | — | $C_5H_{11}$ |
| 324 | $C_8H_{17}O$ | — | Ph | —COO— | Ph | 8 | L2 | — | $C_6H_{13}$ |
| 325 | $C_8H_{17}$ | — | Pr1 | — | Ph | 9 | L2 | — | $C_8H_{17}$ |
| 326 | $C_{10}H_{21}$ | — | Pr2 | — | Ph | 6 | L2 | — | $C_4H_9$ |
| 327 | $C_{11}H_{23}$ | — | Pr2 | — | Ph | 4 | L2 | — | $C_6H_{13}$ |
| 328 | $C_{12}H_{25}$ | — | Pr2 | —COO— | Ph | 5 | L2 | — | $C_8H_{17}$ |
| 329 | $C_4H_9O$ | — | Py1 | — | Ph | 6 | L2 | — | $C_{10}H_{21}$ |
| 330 | $C_{13}H_{27}$ | — | Py2 | — | Ph | 2 | L2 | — | $C_5H_{11}$ |
| 331 | $C_6H_{13}O$ | — | Py2 | — | Ph | 4 | L2 | — | $C_8H_{17}$ |
| 332 | $C_6H_{13}'(CF_3)CH_2O$ | — | Py2 | — | Ph | 6 | L2 | — | $C_9H_{19}$ |
| 333 | $C_5H_{11}O$ | — | Py2 | — | Ph23F | 8 | L2 | — | $C_4H_9$ |
| 334 | $C_{10}H_{21}$ | — | Py2 | — | Ph | 2 | L2 | — | $C_6H_{13}$ |
| 335 | $C_8H_{17}$ | — | Py2 | — | Ph3F | 7 | L2 | — | $C_7H_{15}$ |
| 336 | $C_6H_{13}$ | — | Cy | — | Ph | 8 | L2 | — | $C_3H_6OC_4H_9$ |
| 337 | $C_6H_{13}OCO$ | — | Cy | — | Ph | 2 | L2 | — | $C_{14}H_{29}$ |
| 338 | $C_6H_{13}$ | — | Cy | —CH=CH— | Ph | 5 | L2 | — | $C_{10}H_{21}$ |
| 339 | $C_3H_7$ | — | Cy | —COO— | Ph | 6 | L2 | — | $C_6H_{13}$ |
| 340 | $C_5H_{11}$ | — | Pa | — | Ph | 4 | L2 | — | $C_8H_{17}$ |
| 341 | $C_{10}H_{21}$ | — | Pd | — | Ph | 5 | L2 | — | $C_6H_{13}$ |
| 342 | $C_6H_{13}$ | — | Dt2 | — | Ph | 3 | L2 | — | $(CH_2)_2CH=CH_2$ |
| 343 | $C_8H_{17}$ | — | Tn | — | Ph | 8 | L2 | — | $C_9H_{19}$ |
| 344 | $C_6H_{13}'CHFCH_2CH_2$ | — | Py2 | — | Ph | 4 | L2 | — | $C_6H_{13}$ |
| 345 | $C_5H_{11}$ | — | Tz1 | — | Ph | 6 | L2 | — | $C_8H_{17}$ |
| 346 | $C_9H_{19}O$ | — | Tz2 | — | Ph | 4 | L2 | — | $C_5H_{11}$ |
| 347 | $C_2H_5$ | — | Td | — | Ph | 8 | L2 | — | $C_8H_{17}$ |
| 348 | $C_{10}H_{21}$ | — | Dx2 | — | Ph | 10 | L2 | — | $C_7H_{15}$ |
| 349 | $C_6H_{13}$ | — | Boa2 | — | Ph | 11 | L2 | — | $C_{10}H_{21}$ |
| 350 | $C_7H_{15}$ | — | Bob2 | — | Ph | 2 | L2 | — | $C_6H_{13}$ |
| 351 | $C_{16}H_{33}O$ | — | Bta2 | — | Ph | 4 | L2 | — | $C_6H_{13}$ |
| 352 | $C_6H_{13}$ | — | Btb2 | — | Ph | 6 | L2 | — | $C_{14}H_{29}$ |
| 353 | $C_5H_{11}$ | — | Np | —COO— | Ph | 8 | L2 | — | $C_7H_{15}$ |
| 354 | $C_8H_{17}'CFHCH_2O$ | — | Ep1 | — | Ph | 5 | L2 | — | $C_{10}H_{21}$ |
| 355 | $C_4H_9$ | — | Ep2 | — | Ph | 2 | L2 | — | $C_6H_{13}$ |
| 356 | $C_6H_{13}$ | — | Gp1 | — | Ph | 3 | L2 | — | $C_{12}H_{25}$ |
| 357 | $C_7H_{15}$ | — | Gp2 | — | Ph | 6 | L2 | — | $C_6H_{13}$ |
| 358 | $C_6H_{13}$ | — | Cm1 | — | Ph | 4 | L2 | — | $C_8H_{17}$ |
| 359 | $C_8H_{17}$ | — | Io1 | — | Ph | 8 | L2 | — | $C_6H_{13}$ |
| 360 | $C_{20}H_{41}$ | — | Id1 | —COO— | Ph | 10 | L2 | — | $C_4H_9$ |
| 361 | $C_{11}H_{23}$ | — | Id1 | — | Ph | 2 | L2 | — | $C_8H_{17}$ |
| 362 | $C_8H_{17}$ | — | Id1 | — | Ph | 4 | L2 | — | $C_8H_{17}$ |
| 363 | $C_5H_{11}$ | — | Id1 | — | Ph2F | 6 | L2 | — | $C_6H_{13}$ |
| 364 | $C_6H_{13}$ | — | Tn | — | Ph | 18 | L2 | — | $C_7H_{15}$ |
| 365 | $C_4H_9O$ | — | Tz2 | — | Ph | 9 | L2 | — | $C_9H_{19}$ |
| 366 | $C_{12}H_{25}$ | — | Btb2 | — | Ph | 8 | L2 | — | $C_6H_{13}$ |
| 367 | $C_6H_{13}O$ | — | Btb2 | — | Ph | 5 | L2 | — | $C_9H_{19}$ |
| 368 | $CH_2=CH(CH_2)_8O$ | — | Ep2 | — | Ph | 4 | L2 | — | $C_6H_{13}$ |
| 369 | $C_9H_{19}$ | — | Gp2 | — | Ph | 4 | L2 | — | $C_5H_{11}$ |
| 370 | $C_5H_{11}O$ | — | Np | — | Ph | 6 | L2 | — | $C_{10}H_{21}$ |
| 371 | $C_6H_{13}$ | Ph | Ph | — | Ph | 2 | L2 | — | $C_3H_7$ |
| 372 | F | Pr2 | Ph | — | Ph | 5 | L2 | — | $C_6H_{13}$ |
| 373 | $C_3H_7$ | Py2 | Ph | — | Ph | 2 | L2 | — | $C_8H_{17}$ |
| 374 | $C_5H_{11}$ | — | Ha2 | — | Ph | 5 | L2 | — | $C_{11}H_{23}$ |
| 375 | $C_6H_{13}$ | Ph | Pr2 | — | Ph | 6 | L2 | — | $C_6H_{13}$ |
| 376 | $C_9H_{19}$ | Ph | Pr1 | — | Ph | 4 | L2 | — | $C_5H_{11}$ |
| 377 | $C_{13}H_{27}$ | Ph | Cy | — | Ph3Br | 9 | L2 | — | $C_7H_{15}$ |
| 378 | $C_{10}H_{21}O$ | Ph | Py1 | — | Ph | 4 | L2 | — | $C_6H_{13}$ |
| 379 | $C_7H_{15}$ | Ph | Py2 | — | Ph | 6 | L2 | — | $C_{10}H_{21}$ |
| 380 | $C_4H_9$ | Ph3TF | Pa | — | Ph | 7 | L2 | — | $(CH_2)_5CH(CH_3)_2$ |
| 381 | H | — | Hb2 | — | Ph | 8 | L2 | — | $C_8H_{17}$ |
| 382 | $C_8H_{17}$ | Ph | Tn | — | Ph | 8 | L2 | — | $C_5H_{11}$ |
| 383 | $C_2H_5$ | Ph | Tz1 | — | Ph2M | 3 | L2 | — | $C_3H_7$ |
| 384 | $C_6H_{13}$ | Ph | Tz2 | — | Ph | 4 | L2 | — | $C_6H_{13}$ |
| 385 | $C_{10}H_{21}$ | Ph | Td | — | Ph | 6 | L2 | — | $C_7H_{15}$ |
| 386 | $C_{10}H_{21}$ | — | Ph | — | Py1 | 2 | L2 | — | $C_6H_{13}$ |

TABLE 1-continued

| No. | R₁ | A₁ | A₂ | X₁ | A₃ | p | L | A₄ | R₂ |
|---|---|---|---|---|---|---|---|---|---|
| 387 | C₆H₁₃ | — | Ph | — | Py1 | 4 | L2 | — | C₆H₁₃ |
| 388 | C₆H₁₃OCO | — | Ph | — | Py1 | 6 | L2 | — | C₅H₁₁ |
| 389 | C₇H₁₅ | — | — | — | Pr2 | 4 | L2 | — | C₁₀H₂₁ |
| 390 | C₉H₁₉ | — | Ph | — | Pr2 | 8 | L2 | — | C₈H₁₇ |
| 391 | C₃H₇ | — | Ph | — | Pr2 | 11 | L2 | — | C₅H₁₃ |
| 392 | C₅H₁₁O | — | — | — | Cy | 4 | L2 | — | C₄H₉ |
| 393 | C₄H₉ | — | Ph | —CH₂O— | Cy | 6 | L2 | — | C₇H₁₅ |
| 394 | C₁₂H₂₅ | — | Ph | — | Cy | 8 | L2 | — | C₃H₇ |
| 395 | C₆H₁₃C≡C | — | Ph | — | Pa | 9 | L2 | — | C₆H₁₃ |
| 396 | C₈H₁₇O | — | Ph | — | Pd | 4 | L2 | — | C₅H₁₁ |
| 397 | C₃H₇ | — | Ph2Cl | — | Tn | 5 | L2 | — | C₁₀H₂₁ |
| 398 | C₄H₉ | — | Ph | — | Tn | 6 | L2 | — | C₇H₁₅ |
| 399 | C₈H₁₇ | — | Ph | — | Tz1 | 8 | L2 | — | C₁₂H₂₅ |
| 400 | C₄H₉OCH(CH₃)COO | — | Ph | — | Tz1 | 4 | L2 | — | C₅H₁₁ |
| 401 | C₆H₁₃ | — | Ph2F | — | Td | 6 | L2 | — | CH₂CH(CH₃)C₆H₁₃ |
| 402 | C₅H₁₁ | — | — | — | Np | 8 | L2 | — | C₉H₁₉ |
| 402 | C₈H₁₇OCH₂CH₂ | — | Ph | — | Np | 7 | L2 | — | C₅H₁₁ |
| 404 | C₁₁H₂₃ | — | Ph | — | Np | 10 | L2 | — | C₅H₁₃ |
| 405 | C₅H₁₁ | — | — | — | Ep1 | 15 | L2 | — | C₄H₉ |
| 406 | CH₃ | — | Ph | — | Ep1 | 2 | L2 | — | C₇H₁₅ |
| 407 | C₆H₁₃ | — | Ph | — | Ep1 | 4 | L2 | — | C₆H₁₃ |
| 408 | C₉H₁₉O | — | — | — | Gp1 | 14 | L2 | — | C₈H₁₇ |
| 409 | C₈H₁₇ | — | Ph | — | Gp1 | 3 | L2 | — | C₁₀H₂₁ |
| 410 | C₃H₇COO | — | Ph | — | Gp1 | 4 | L2 | — | C₁₁H₂₃ |
| 411 | C₄H₉ | — | Ph | — | Id1 | 6 | L2 | — | C₇H₁₅ |
| 412 | C₁₂H₂₅ | — | Ph | — | Io1 | 8 | L2 | — | C₆H₁₃ |
| 413 | C₁₀H₂₁ | — | Ph | — | Cm1 | 4 | L2 | — | C₅H₁₁ |
| 414 | C₆H₁₃ | — | Ph | — | Ph | 6 | L2 | — | (CH₂)₂C₄F₉ |
| 415 | C₃H₇ | Ph | Ph | — | Py1 | 8 | L2 | — | C₇H₁₅ |
| 416 | C₄H₉ | Ph2CN | Ph | — | Pr1 | 3 | L2 | — | C₄H₉ |
| 417 | C₅H₁₁ | Ph | Ph3F | — | Tz1 | 8 | L2 | — | C₃H₇ |
| 418 | CN | Ph | Ph | — | Tn | 4 | L2 | — | CH₃ |
| 419 | C₇H₁₅ | Tn | Ph | — | Py1 | 6 | L2 | — | C₈H₁₇ |
| 420 | C₁₀H₁₁ | Ph | Ph | — | Cy | 8 | L2 | — | C₆H₁₃ |
| 421 | C₄F₉OCF₂CF₂OCF₂CH₂O | — | — | — | Ph | 2 | L1 | — | C₈H₁₇ |
| 422 | C₄F₉OCF₂CF₂OCF₂CH₂O | — | — | — | Ph | 4 | L2 | — | C₁₈H₃₇ |
| 423 | C₂F₅OCF₂CH₂O | — | — | — | PH2F | 6 | L1 | Ph | C₆H₁₃ |
| 424 | C₂F₅OCF₂CH₂O | — | Ph | — | Ph | 2 | L1 | — | C₆H₁₃ |
| 425 | C₄F₉OCF₂CF₂OCF₂CH₂O | — | Ph | — | Ph | 2 | L1 | — | C₆H₁₃ |
| 426 | C₄F₉OCF₂CF₂OCF₂CH₂O | — | Ph | — | Ph23F | 4 | L2 | — | C₆H₁₃ |
| 427 | C₄F₉OCF₂CF₂OCF₂CH₂O | — | Ph | —OCH₂— | Ph | 2 | L1 | — | C₉H₁₉ |
| 428 | C₂F₅OCF₂CH₂O | — | Ph | —C≡C— | Ph | 2 | L1 | Ph | H |
| 429 | C₄F₉OCF₂CF₂OCF₂CH₂O | — | Ph | —COO— | Ph | 3 | L1 | — | C₅H₁₃ |
| 430 | C₄F₉OCF₂CF₂OCF₂CH₂O | — | Pr1 | — | Ph | 2 | L1 | — | C₈H₁₇ |
| 431 | C₄F₉OCF₂CF₂OCF₂CH₂O | — | Pr2 | — | Ph | 4 | L1 | Ph | OCH₂C₆F₁₃ |
| 432 | C₂F₅OCF₂CH₂O | — | Pr2 | — | Ph | 5 | L2 | — | C₆H₁₃ |
| 433 | C₄F₉OCF₂CF₂OCF₂CH₂O | — | Pr2 | —COO— | Ph | 2 | L1 | — | C₈H₁₇ |
| 434 | C₄F₉OCF₂CF₂OCF₂CH₂O | — | Py1 | — | Ph | 2 | L1 | — | C₁₀H₂₁ |
| 435 | C₂F₅OCF₂CH₂O | — | Py2 | — | Ph | 6 | L2 | — | C₅H₁₁ |
| 436 | C₄F₉OCF₂CF₂OCF₂CH₂O | — | Ph | — | Py1 | 8 | L1 | — | C₈H₁₇ |
| 437 | C₄F₉OCF₂CF₂OCF₂CH₂O | — | Py2 | — | Ph | 2 | L1 | — | C₉H₁₉ |
| 438 | C₄F₉OCF₂CF₂OCF₂CH₂O | — | Py2 | — | Ph23F | 2 | L1 | — | C₄H₉ |
| 439 | C₂F₅OCF₂CH₂O | — | Ph | — | Py1 | 2 | L1 | Ph | C₆H₁₃ |
| 440 | C₄F₉OCF₂CF₂OCF₂CH₂O | — | Py2 | — | Ph3F | 2 | L1 | — | C₇H₁₅ |
| 441 | C₄F₉OCF₂CF₂OCF₂CH₂O | — | Cy | — | Ph | 8 | L2 | — | C₄H₈OC₄F₉ |
| 442 | C₂F₅OCF₂CH₂O | — | Np | — | Ph | 2 | L1 | — | C₁₄H₂₉ |
| 443 | C₄F₉OCF₂CF₂OCF₂CH₂O | — | Cy | —CH=CH— | Ph | 4 | L1 | — | C₁₀H₂₁ |
| 444 | C₄F₉OCF₂CF₂OCF₂CH₂O | — | Ep2 | —COO— | Ph | 3 | L1 | — | C₆H₁₃ |
| 445 | C₄F₉OCF₂CF₂OCF₂CH₂O | — | Pa | — | Ph | 7 | L1 | — | C₈H₁₇ |
| 446 | C₄F₉OCF₂CF₂OCF₂CH₂O | — | Ph | — | Pd | 2 | L1 | Ph | C₆H₁₃ |
| 447 | C₄F₉OCF₂CF₂OCF₂CH₂O | — | Py2 | — | Ph | 2 | L1 | — | (CH₂)₆CH=CH₂ |
| 448 | C₄F₉OCF₂CF₂OCF₂CH₂O | — | Ph | — | Tn | 2 | L1 | — | C₉H₁₉ |
| 449 | C₂F₅OCF₂CH₂O | — | Py2 | — | Ph | 6 | L2 | — | C₆H₁₃ |
| 450 | C₄F₉OCF₂CF₂OCF₂CH₂O | — | Gp2 | — | Ph | 2 | L1 | — | C₈H₁₇ |
| 451 | C₂F₅OCF₂CH₂O | — | Tz2 | — | Ph | 2 | L1 | Ph | H |
| 452 | C₄F₉OCF₂CF₂OCF₂CH₂O | — | Td | — | Ph | 9 | L1 | — | C₈H₁₇ |
| 453 | C₄F₉OCF₂CF₂OCF₂CH₂O | — | Dx2 | — | Ph | 2 | L1 | — | C₇H₁₅ |
| 454 | C₂F₅OCF₂CH₂O | — | Bta2 | — | Ph | 2 | L1 | — | C₁₀H₂₁ |
| 455 | C₄F₉OCF₂CF₂OCF₂CH₂O | — | Btb2 | — | Ph | 4 | L1 | — | C₆H₁₃ |
| 456 | C₆F₁₃CH₂O | — | Py2 | — | Ph | 2 | L1 | — | C₆H₁₃ |
| 457 | C₅F₁₁CH₂O | — | Ph | — | Py1 | 4 | L2 | — | C₁₄H₂₉ |
| 458 | C₆F₁₃CH₂O | — | Np | —COO— | Ph | 2 | L1 | Ph | C₇H₁₅ |
| 459 | C₈F₁₇CH₂O | — | Py1 | — | Ph | 5 | L1 | — | C₁₀H₂₁ |
| 460 | C₁₀F₂₁CH₂O | — | Py2 | — | Ph | 2 | L1 | — | C₆H₁₃ |
| 461 | C₄F₉CH₂O | — | Gp1 | — | Pr1 | 2 | L1 | — | C₁₂H₂₅ |
| 462 | C₃F₇CH₂O | — | Pr2 | — | Ph | 6 | L2 | Ph | OCH₂CF₂OC₂F₅ |
| 463 | C₆F₁₃CH₂O | — | Py1 | — | Py1 | 2 | L1 | — | C₈H₁₇ |

TABLE 1-continued

| No. | $R_1$ | $A_1$ | $A_2$ | $X_1$ | $A_3$ | p | L | $A_4$ | $R_2$ |
|---|---|---|---|---|---|---|---|---|---|
| 464 | $C_6F_{13}CH_2O$ | — | Ph | — | Ph | 8 | L2 | — | $C_6H_{13}$ |
| 465 | $C_9F_{19}CH_2O$ | — | Ph | —COO— | Ph | 2 | L1 | — | $C_4H_9$ |
| 466 | $C_8F_{17}CH_2O$ | — | Ph | — | Cy | 2 | L1 | Ph | H |
| 467 | $C_8H_{17}$ | — | Py2 | — | Ph | 2 | L1 | Ph | $CF_3$ |
| 468 | $C_5H_{11}$ | — | Py2 | — | Ph2F | 4 | L2 | Ph | $CF_3$ |
| 469 | $C_6H_{13}$ | — | Py2 | — | Ph | 2 | L1 | — | $CF_3$ |
| 470 | $C_2F_5OCF_2CH_2O$ | — | Ph | — | Ph | 2 | L1 | — | $CF_3$ |
| 471 | $C_8F_{17}CH_2O$ | — | Ph | — | Ph | 6 | L2 | — | $CF_3$ |
| 472 | $C_6H_{13}O$ | — | Ph | — | Ph | 4 | L2 | Ph | F |
| 473 | $CH_2=CH(CH_2)_3O$ | — | Ph | — | Ph | 6 | L2 | Ph | F |
| 474 | $C_9H_{19}$ | — | Ph | — | Ph | 7 | L2 | Ph | F |
| 475 | $C_5H_{11}O$ | — | Ph | — | Ph | 4 | L2 | Ph | CN |
| 476 | $C_{10}H_{21}$ | — | Py2 | — | Ph | 8 | L2 | — | $CH_3$ |
| 477 | $C_2F_5OCF_2CH_2O$ | Pr2 | Ph | — | Ph | 3 | L2 | — | CN |
| 478 | $C_8H_{17}$ | — | Id1 | — | Ph | 2 | L1 | Ph | $OCH_3$ |
| 479 | $C_{10}H_{21}$ | — | Py2 | — | Ph | 2 | L1 | — | $(CH_2)_6CH=CH_2$ |
| 480 | $C_{10}H_{21}$ | — | Py2 | — | Ph | 2 | L1 | — | $CH_2OC_6H_{13}$ |
| 481 | $C_8H_{17}$ | — | Ep2 | — | Ph | 2 | L1 | — | $C_6H_{13}$ |
| 482 | $C_8H_{17}$ | — | Gp2 | — | Ph | 4 | L1 | — | $C_6H_{13}$ |
| 483 | $C_{10}H_{21}O$ | — | Py2 | — | Ph | 2 | L1 | — | $C_6H_{13}$ |
| 484 | $C_{10}H_{21}O$ | — | Py2 | — | Ph | 2 | L1 | — | $C_5H_{11}$ |
| 485 | $C_{10}H_{21}O$ | — | Py2 | — | Ph | 2 | L1 | — | $C_8H_{17}$ |
| 486 | $C_8H_{17}$ | — | Py2 | — | Ph | 2 | L1 | — | $C_6H_{13}$ |
| 487 | $C_8H_{17}$ | — | Py2 | — | Ph | 2 | L1 | — | $C_6H_{13}$ |
| 488 | $C_8H_{17}$ | — | Py2 | — | Ph | 2 | L1 | — | $C_5H_{11}$ |
| 489 | $C_{10}H_{21}O$ | — | Py2 | — | Ph | 4 | L1 | — | $C_6H_{13}$ |
| 490 | $C_{10}H_{21}O$ | — | Py2 | — | Ph | 5 | L1 | — | $C_6H_{13}$ |
| 491 | $La1(0,6)CH_2CH_2$ | — | Py2 | — | Ph | 2 | L1 | — | $C_6H_{13}$ |
| 492 | $La2(0,6)CH_2O$ | — | Ph | — | Ph | 4 | L1 | — | $C_6H_{13}$ |
| 493 | $Lc1(0,5)$ | — | Ph | — | Ph | 2 | L1 | — | $C_7H_{15}$ |
| 494 | $Lc2(1,1)OCO$ | — | Ph | — | Ph | 5 | L1 | — | $C_{10}H_{21}$ |
| 495 | P1a-OCO | — | Ph | — | Ph | 2 | L2 | — | $C_6H_{13}$ |
| 496 | Thf(0)-COO | — | Ph | — | Ph | 2 | L1 | — | $C_{10}H_{21}$ |
| 497 | $Dp(2)-CH_2O$ | — | Ph | — | Ph | 6 | L2 | — | $C_{10}H_{21}$ |
| 498 | $Ox(3)-CH_2O$ | — | Ph | — | Ph | 2 | L1 | — | $C_8H_{17}$ |
| 499 | Ox(4)-COO | — | Ph | — | Ph | 8 | L2 | — | $C_6H_{13}$ |
| 500 | La1(0,6) | — | Ph | — | Ph | 2 | L1 | — | $C_4H_9$ |
| 501 | $C_{10}H_{21}O$ | — | Py2 | — | Ph | 2 | L1 | — | $CH_2OC_6H_{13}$ |
| 502 | $La1(0,5)-(CH2)4$ | — | Py2 | — | Ph | 4 | L1 | — | $C_6H_{13}$ |
| 503 | $C_{10}H_{21}$ | — | Py2 | — | Ph | 2 | L1 | — | $C_3H_7$ |
| 504 | $C_{10}H_{21}$ | — | Py2 | — | Ph | 4 | L1 | — | $C_6H_{13}$ |
| 505 | $C_{10}H_{21}$ | — | Py2 | — | Ph | 3 | L1 | — | $C_6H_{13}$ |
| 506 | $C_{10}H_{21}$ | — | Py2 | — | Ph | 4 | L2 | — | $C_6H_{13}$ |
| 507 | $C_5H_{11}$ | — | Cy | — | Ph | 4 | L2 | — | $C_6H_{13}$ |
| 508 | $C_{10}H_{21}$ | — | Ph | — | Py1 | 4 | L2 | — | $C_6H_{13}$ |

According to the present invention, there is also provided compounds represented by the following general formula (II) as compounds relating to the compounds represented by general formula (I):

$$CH_2=CH-(CH_2)_{p'}-L'-R_2 \quad (II)$$

where p' is an integer from 0 to 18, L' is optically active 4-butanolyde-2,4-diyl and $R_2$ is $R_2$ is F, CN or straight chain, branched or cyclic alkyl group (one or more —$CH_2$— in the alkyl group may be replaced by —O—, —S—, —CO—, —CH (CN)—, —CH=CH— or —C≡C— under condition that hetero atoms do not position adjacent) which has 3 to 30 carbon atoms and which can be substituted.

In the optically active compound represented by general formula (II), it is preferable that p' is an integer from 0 to 10, and more preferably an integer from 0 to 4, and most preferably an integer 0, 2 or 4.

L' is preferably 4-butanolyde-2,4-diyl and R2 is preferably a straight chain alkyl group having 4 to 10 carbon atoms.

In the viewpoints of easily performing the preparing process and obtaining stability, it is preferable that L' in the compound represented by general formula (II) is 4-butanolyde-2,4-diyl and $R_2$ is a straight chain hexyl group.

The optically active compound represented by general formula (II) is advantageous to serve as an intermediate material for preparing the optically active compound represented by general formula (I) in a case where L' is 4-butanolyde-2,4-diyl and as well as $R_2$ is —$C_6H_{13}$—. Furthermore, it is an effective compound to serve as an intermediate material for preparing a functional material and any of a variety of optically active materials (refer to the foregoing preparing methods B to D).

Schematic constitutional formula of the optically active compound represented by general formula (II) is shown in Table 2.

$$CH_2=CH_2(CH_2)_{p'}-L'-R_2 \quad (II)$$

TABLE 2

| No. | P' | L' | R2 |
|---|---|---|---|
| 509 | 0 | L1 | $C_6H_{13}$ |
| 510 | 1 | L1 | $C_6H_{13}$ |
| 511 | 2 | L1 | $C_6H_{13}$ |
| 512 | 3 | L1 | $C_6H_{13}$ |
| 513 | 4 | L1 | $C_6H_{13}$ |
| 514 | 5 | L1 | $C_6H_{13}$ |

TABLE 2-continued

| No. | P' | L' | R2 |
|---|---|---|---|
| 515 | 6 | L1 | $C_6H_{13}$ |
| 516 | 7 | L1 | $C_6H_{13}$ |
| 517 | 8 | L1 | $C_6H_{13}$ |
| 518 | 9 | L1 | $C_6H_{13}$ |
| 519 | 10 | L1 | $C_6H_{13}$ |
| 520 | 0 | L2 | $C_6H_{13}$ |
| 521 | 1 | L2 | $C_6H_{13}$ |
| 522 | 2 | L2 | $C_6H_{13}$ |
| 523 | 3 | L2 | $C_6H_{13}$ |
| 524 | 4 | L2 | $C_6H_{13}$ |
| 525 | 5 | L2 | $C_6H_{13}$ |
| 526 | 6 | L2 | $C_6H_{13}$ |
| 527 | 7 | L2 | $C_6H_{13}$ |
| 528 | 8 | L2 | $C_6H_{13}$ |
| 529 | 9 | L2 | $C_6H_{13}$ |
| 530 | 10 | L2 | $C_6H_{13}$ |
| 531 | 0 | L1 | $C_3H_7$ |
| 532 | 1 | L1 | $C_3H_7$ |
| 533 | 2 | L1 | $C_3H_7$ |
| 534 | 3 | L1 | $C_3H_7$ |
| 535 | 4 | L1 | $C_3H_7$ |
| 536 | 5 | L1 | $C_3H_7$ |
| 537 | 6 | L1 | $C_3H_7$ |
| 538 | 7 | L1 | $C_3H_7$ |
| 539 | 8 | L1 | $C_3H_7$ |
| 540 | 9 | L1 | $C_3H_7$ |
| 541 | 10 | L1 | $C_3H_7$ |
| 542 | 0 | L2 | $C_3H_7$ |
| 543 | 1 | L2 | $C_3H_7$ |
| 544 | 2 | L2 | $C_3H_7$ |
| 545 | 3 | L2 | $C_3H_7$ |
| 546 | 4 | L2 | $C_3H_7$ |
| 547 | 5 | L2 | $C_3H_7$ |
| 548 | 6 | L2 | $C_3H_7$ |
| 549 | 7 | L2 | $C_3H_7$ |
| 550 | 8 | L2 | $C_3H_7$ |
| 551 | 9 | L2 | $C_3H_7$ |
| 552 | 10 | L2 | $C_3H_7$ |
| 553 | 0 | L1 | $C_4H_9$ |
| 554 | 1 | L1 | $C_4H_9$ |
| 555 | 2 | L1 | $C_4H_9$ |
| 556 | 3 | L1 | $C_4H_9$ |
| 557 | 4 | L1 | $C_4H_9$ |
| 558 | 5 | L1 | $C_4H_9$ |
| 559 | 6 | L1 | $C_4H_9$ |
| 560 | 7 | L1 | $C_4H_9$ |
| 561 | 8 | L1 | $C_4H_9$ |
| 562 | 9 | L1 | $C_4H_9$ |
| 563 | 10 | L1 | $C_4H_9$ |
| 564 | 0 | L2 | $C_4H_9$ |
| 565 | 1 | L2 | $C_4H_9$ |
| 566 | 2 | L2 | $C_4H_9$ |
| 567 | 3 | L2 | $C_4H_9$ |
| 568 | 4 | L2 | $C_4H_9$ |
| 569 | 5 | L2 | $C_4H_9$ |
| 570 | 6 | L2 | $C_4H_9$ |
| 571 | 7 | L2 | $C_4H_9$ |
| 572 | 8 | L2 | $C_4H_9$ |
| 573 | 9 | L2 | $C_4H_9$ |
| 574 | 10 | L2 | $C_4H_9$ |
| 575 | 0 | L1 | $C_5H_{11}$ |
| 576 | 1 | L1 | $C_5H_{11}$ |
| 577 | 2 | L1 | $C_5H_{11}$ |
| 578 | 3 | L1 | $C_5H_{11}$ |
| 579 | 4 | L1 | $C_5H_{11}$ |
| 580 | 5 | L1 | $C_5H_{11}$ |
| 581 | 6 | L1 | $C_5H_{11}$ |
| 582 | 7 | L1 | $C_5H_{11}$ |
| 583 | 8 | L1 | $C_5H_{11}$ |
| 584 | 9 | L1 | $C_5H_{11}$ |
| 585 | 10 | L1 | $C_5H_{11}$ |
| 586 | 0 | L2 | $C_5H_{11}$ |
| 587 | 1 | L2 | $C_5H_{11}$ |
| 588 | 2 | L2 | $C_5H_{11}$ |
| 589 | 3 | L2 | $C_5H_{11}$ |
| 590 | 4 | L2 | $C_5H_{11}$ |
| 591 | 5 | L2 | $C_5H_{11}$ |
| 592 | 6 | L2 | $C_5H_{11}$ |
| 593 | 7 | L2 | $C_5H_{11}$ |
| 594 | 8 | L2 | $C_5H_{11}$ |
| 595 | 9 | L2 | $C_5H_{11}$ |
| 596 | 10 | L2 | $C_5H_{11}$ |
| 597 | 0 | L1 | $C_7H_{15}$ |
| 598 | 1 | L1 | $C_7H_{15}$ |
| 599 | 2 | L1 | $C_7H_{15}$ |
| 600 | 3 | L1 | $C_7H_{15}$ |
| 601 | 4 | L1 | $C_7H_{15}$ |
| 602 | 5 | L1 | $C_7H_{15}$ |
| 603 | 6 | L1 | $C_7H_{15}$ |
| 604 | 7 | L1 | $C_7H_{15}$ |
| 605 | 8 | L1 | $C_7H_{15}$ |
| 606 | 9 | L1 | $C_7H_{15}$ |
| 607 | 10 | L1 | $C_7H_{15}$ |
| 608 | 0 | L2 | $C_7H_{15}$ |
| 609 | 1 | L2 | $C_7H_{15}$ |
| 610 | 2 | L2 | $C_7H_{15}$ |
| 611 | 3 | L2 | $C_7H_{15}$ |
| 612 | 4 | L2 | $C_7H_{15}$ |
| 613 | 5 | L2 | $C_7H_{15}$ |
| 614 | 6 | L2 | $C_7H_{15}$ |
| 615 | 7 | L2 | $C_7H_{15}$ |
| 616 | 8 | L2 | $C_7H_{15}$ |
| 617 | 9 | L2 | $C_7H_{15}$ |
| 618 | 10 | L2 | $C_7H_{15}$ |
| 619 | 0 | L1 | $C_8H_{17}$ |
| 620 | 1 | L1 | $C_8H_{17}$ |
| 621 | 2 | L1 | $C_8H_{17}$ |
| 622 | 3 | L1 | $C_8H_{17}$ |
| 623 | 4 | L1 | $C_8H_{17}$ |
| 624 | 5 | L1 | $C_8H_{17}$ |
| 625 | 6 | L1 | $C_8H_{17}$ |
| 626 | 7 | L1 | $C_8H_{17}$ |
| 627 | 8 | L1 | $C_8H_{17}$ |
| 628 | 9 | L1 | $C_8H_{17}$ |
| 629 | 10 | L1 | $C_8H_{17}$ |
| 630 | 0 | L2 | $C_8H_{17}$ |
| 631 | 1 | L2 | $C_8H_{17}$ |
| 632 | 2 | L2 | $C_8H_{17}$ |
| 633 | 3 | L2 | $C_8H_{17}$ |
| 634 | 4 | L2 | $C_8H_{17}$ |
| 635 | 5 | L2 | $C_8H_{17}$ |
| 636 | 6 | L2 | $C_8H_{17}$ |
| 637 | 7 | L2 | $C_8H_{17}$ |
| 638 | 8 | L2 | $C_8H_{17}$ |
| 639 | 9 | L2 | $C_8H_{17}$ |
| 640 | 10 | L2 | $C_8H_{17}$ |

The liquid crystal composition according to the present invention can be prepared by mixing one or more optically active compounds represented by general formula (I), preferably (I'), and one or more other liquid crystal compounds (mesomorphic compounds) at an adequate ratio. The number of the other liquid crystal compounds to be used together is 1 to 50, preferably 1 to 30, and most preferably 3 to 30.

The "mesomorphic compound" according to the present invention is required to be liquid crystal or serve as a preferred component of a liquid crystal composition in the composition.

It is preferable that the liquid crystal composition according to the present invention be a chiral smectic liquid crystal composition, and in particular, be a ferroelectric chiral smectic liquid crystal composition.

The "other liquid crystal compound" according to the present invention may be any of the following materials disclosed in Japanese Patent Laid-Open No. 4-272989: compounds (III) to (XII), preferably (IIIa) to (XIId), and more preferably (IIIaa) to (XIIdb). Furthermore, any of the following compounds may be employed: compounds (III) to (VI), preferably (IIIa) to (VIf) and more preferably (IIIaa) to (VIfa), in which $R'_1$ and/or $R'_2$ is —$(CH_2)_E C_G F_{2G+1}$ (where E is an integer from 0 to 10 and G is an integer from 1 to 15), a compound (VII) or (VIII), preferably (VIIa) to (VIIIb) and more preferably (VIIIba) or (VIIIbb) in which $R'_3$ and/or $R'_4$ is the same, and a compound (IX) to (XII), preferably (IXa) to (XIId) and more preferably (IXba) or (XIIdb) in which $R'_5$ and/or $R'_6$ is the same. Moreover, the following liquid crystal compound represented by the following general formulas (XIII) to (XVIII) may be used:

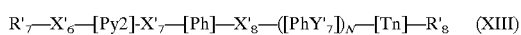   (XIII)

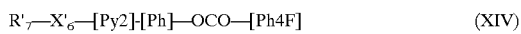   (XIV)

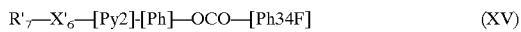   (XV)

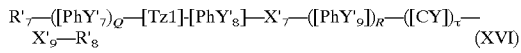   (XVI)

   (XVII)

   (XVIII)

where $R'_7$ and $R'_8$ are straight or branched alkyl groups having 1 to 18 hydrogen atoms or carbon atoms, wherein one or two or more —$CH_2$— groups, which are not positioned adjacent may, except the —$CH_2$— groups which are directly bonded to $X'_6$ and $X'_9$, be replaced by —O—, —CO—, —OCO—, —COO—, —CH(CN)— or —C(CN)($CH_3$).

It is preferable that $R'_7$ and $R'_8$ be (i) to (viii). (i) A straight chain alkyl group having 1 to 15 carbon atoms.

   (ii)

where p is an integer from 0 to 5 and q is an integer from 2 to 11, and which may be optically active.

   (iii)

where r is an integer from 0 to 6, s is an integer 0 or 1 and t is an integer from 1 to 14, and which may be optically active.

   (iv)

where w is an integer from 1 to 15, and which may be optically active.

   (v)

where A is an integer from 0 to 2 and B is an integer from 1 to 15, and which may be optically active.

   (vi)

where C is an integer from 0 to 2 and D is an integer from 1 to 15, and which may be optically active.

   (vii)

where E is an integer from 0 to 10 and G is an integer from 1 to 15.

—H   (viii)

wherein N, Q, R and T respective are integer 0 or 1, $Y'_7$, $Y'_8$ and $Y'_9$ respective are H or F, $A'_4$ is Ph or Np, $X'_6$ and $X'_9$ respectively are single bonds, —COO—, —OCO— or —O—, $X'_7$ and $X'_8$ are single bonds, —COO—, —OCO—, —$CH_2O$— or —$OCH_2$—.

As a preferred compound of (XIII), the following compound (XIIIa) is exemplified:

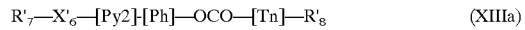   (XIIIa)

As a preferred compound of (XVI), the following compounds (XVIa) and (XVIb) are exemplified:

   (XVIa)

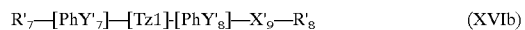   (XVIb)

As a preferred compound of (XVII), the following compounds (XVIIa) and (XVIIb) are exemplified:

   (XVIIa)

   (XVIIb)

As a preferred compound of (XVIII), the following compounds (XVIIIa) and (XVIIIc) are exemplified:

   (XVIIIa)

   (XVIIIb)

   (XVIIIc)

As preferred compounds of (XVIa) and (XVIb), the following compounds (XVIaa) to (XVIbc) are exemplified:

   (XVIaa)

   (XVIba)

   (XVIbb)

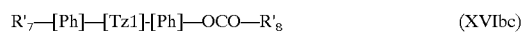   (XVIbc)

wherein abbreviated forms Ph, Py2, Tn, Tz1, Cy, Boa2 and Btb2 are defined similarly to the foregoing definitions and other abbreviated forms represent the following groups:

PhY'$_7$: 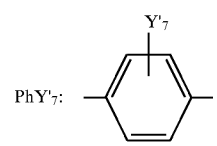

PhY'$_8$: 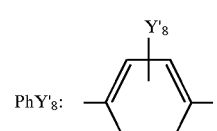

PhY'$_9$: 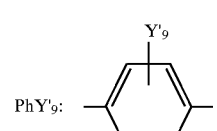

Ph4F: 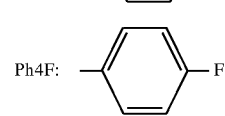

-continued

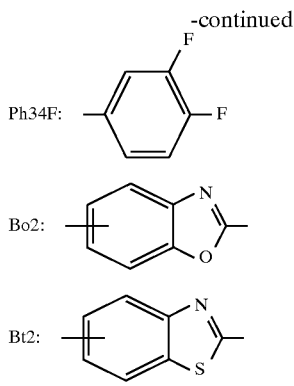

Ph34F:

Bo2:

Bt2:

In a case where the optically active compound according to the present invention and one or more kinds of the foregoing liquid crystal compounds or the liquid crystal compositions are mixed, it is preferable that the ratio of the optically active compound according to the present invention in the liquid crystal composition obtained by mixing be 1 wt % to 80 wt %. To put into practice the chiral smectic liquid crystal device, in particular, the ferroelectric liquid crystal device, a multiplicity of conditions, such as the liquid crystal characteristic, high speed response, high contrast and uniform switching, must be met in a wide temperature range. However, any single compound cannot satisfy all of the foregoing conditions. Therefore, multiple kinds of compounds respectively having individual advantage are usually used to prepare the liquid crystal composition. From the foregoing viewpoint, it is preferable that the ratio of the optically active compound according to the present invention in the liquid crystal composition be 1 wt % to 60 wt %. To cause the characteristics of the other liquid crystal compounds to be exhibited, it is preferable that the ratio be 1 wt % to 40 wt %. If the ratio is lower than 1 wt %, the effect of the compound according to the present invention is unsatisfactory.

It is preferable that two or more kinds of the optically active compounds according to the present invention be used. In this case, the ratio of the mixture of the two or more kinds of the optically active compounds according to the present invention in the liquid crystal composition prepared by mixing is 1 wt % to 80 wt %. In the viewpoint of preparing the liquid crystal composition composed of multiple kinds of compounds, it is preferable that the ratio be 1 wt % to 60 wt %, and more preferably 1 wt % to 40 wt % to cause the characteristics of the other liquid crystal compounds to exhibit.

It is preferable that the chiral smectic phase liquid crystal layer, in particular, the liquid crystal layer of the liquid crystal device according to the present invention be subjected to the processes such that the liquid crystal composition prepared as described above is, in a vacuum state, heated to an isotropic liquid temperature; it is enclosed in a cell for the device; it is gradually cooled to form the liquid crystal layer; and then the temperature is returned to room temperature.

FIG. 1 is schematic cross sectional view which illustrates an example of the liquid crystal device having the chiral smectic phase liquid crystal layer, in particular, a ferroelectric liquid crystal liquid crystal layer according to the present invention to describe the structure of the liquid crystal device. Referring to FIG. 1, reference numeral 1 represents a liquid crystal layer, 2 represents a glass substrate, 3 represents a transparent electrode, 4 represents an insulating orientation control layer, 5 represents a spacer, 6 represents a lead wire, 7 represents a power source, 8 represents a polarizing plate and 9 represents a light source.

The two glass plates 2 are coated with the transparent electrodes 3 made of thin films of $In_2O_3$, $SnO_2$ or ITO (Indium Tin Oxide). Then, polymer thin films, such as polyimide, are rubbed with gauze or acetate filling cloth or the like so that the insulating orientation control layer 4 is formed to orient the liquid crystal in the rubbing direction.

The insulating orientation control layer 4 may be composed of two layers consisting of: an inorganic insulating layer, the insulating material of which is any of the following materials: a silicon nitride, a silicon carbide containing hydrogen, a silicon oxide, a boron nitride, a boron nitride containing hydrogen, a cerium oxide, an aluminum oxide, a zirconium oxide, a titanium oxide and magnesium fluoride; and a orientation control layer made of an organic insulating material, such as polyvinyl alcohol, polyimide, polyamideimide, polyester imide, polyparaxylene, polyester, polycarbonate, polyvinyl acetal, polyvinyl chloride, polyvinyl acetate, polyamide, polystyrene, cellulose resin, melamine resin, urea resin, acryl resin or photoresist resin. As an alternative to this, the insulating orientation control layer 4 may be formed solely by an insulating orientation control layer mainly composed of inorganic substances or an insulating orientation control layer mainly composed of organic substances. If the insulating orientation control layer is mainly made of inorganic substances, it can be formed by an evaporating method. If it is mainly made of organic substances, the insulating orientation control layer can be formed by using a solution in which the organic insulating substances are dissolved or a solution of the precursor of the organic insulating substances (in a quantity of 0.1 wt % to 20 wt % of the solvent) and by hardening the material under a predetermined hardening condition (for example, with heat) by a spinner coating method, a dipping coating method, a screen printing method, a spray coating method or a roll coating method.

The thickness of the insulating orientation control layer 4 is usually 10 Å to 1 $\mu$m, preferably 10 Å to 3000 Å, and most preferably 10 Å to 1000 Å. The two glass substrates 2 are positioned at arbitrary interval by the spacer 5. For example, silica beads or alumina beads each having a predetermined diameter are used as the spacer 5 to be held between the two glass substrates 2. Then, a sealing material, for example, an epoxy bond is used to seal the peripheral portion. As the spacer, a polymer film or glass fiber may be used. The foregoing chiral smectic liquid crystal composition is enclosed between the two glass substrates 2.

The liquid crystal layer 1, in which the liquid crystal has been enclosed, usually has a thickness of 0.5 $\mu$m to 20 $\mu$m, and preferably 1 $\mu$m to 5 $\mu$m.

Figure 2:
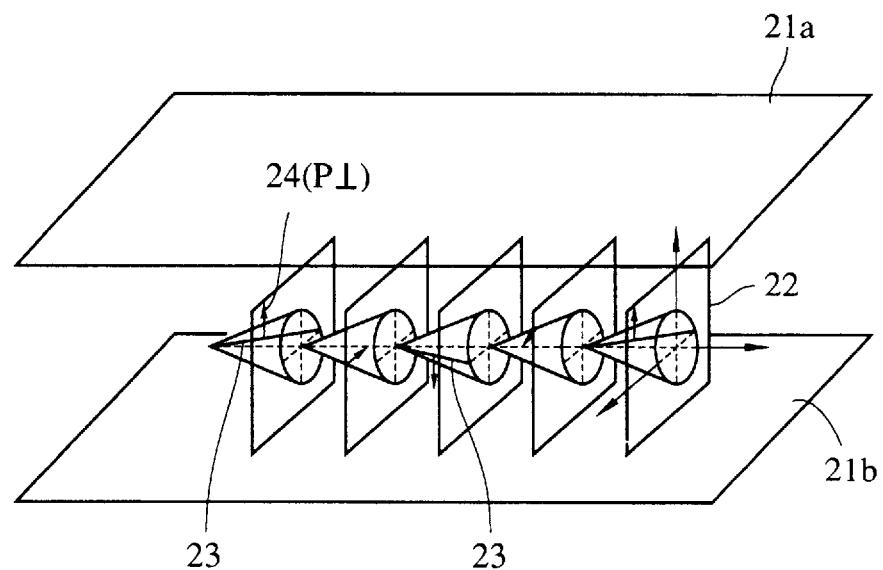
FIG. 2 is a perspective view which schematically illustrates an example of a device cell to explain the operation of a liquid crystal device using ferroelectric characteristic of liquid crystal.

The transparent electrodes 3 are connected to the external power source 7 through lead wires 6. The polarizing plates 8 are applied on the two external sides of the glass plates 2. Since the liquid crystal device shown in FIG. 1 is a transmissive type device, the light source 9 is provided. FIG. 2 is a schematic view of the cell to explain the operation of the liquid crystal device. Reference numerals 21a and 21b represent substrates (glass plates) respectively coated with thin films made of $In_2O_3$, $SnO_2$ or ITO (Indium Tin Oxide). Liquid crystal of phase S*C or S*H oriented such that their liquid crystal molecule layers 22 are perpendicular to the surfaces of the glass plates 21a and 21b is enclosed between the substrates 21a and 21b. Bold lines 23 represent the liquid crystal molecules, the liquid crystal molecules 23 each having dipole moment (P $\perp$) 24. When voltage, the threshold of which is larger than a predetermined value, is applied between the substrates 21a and 21b, the spiral structures of the liquid crystal molecules 23 are untied. Thus, the direction of orientation of the liquid crystal molecules 23 can be changed such that all dipole moments (P ⊥) 24 face the direction of the electric field. The liquid crystal molecule 23 has an elongated shape in which its longer axial direction and a shorter axial direction have anisotropy of the refraction factor. Therefore, it can easily be understand that placing of polarizers crossed-Nicol each other on the upper and lower surfaces of the glass surface enables a liquid crystal optical modulating device to be constituted, the optical characteristic of which is changed based on the polarity of the applied voltage.

Figure 3:
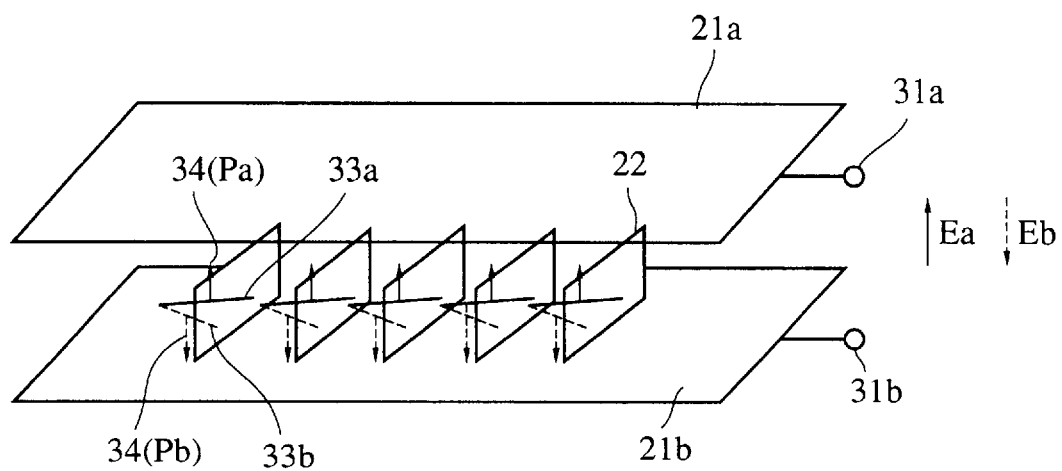
FIG. 3 is a perspective view which schematically illustrates an example of the structure of a device cell to explain the operation of a liquid crystal device using the ferroelectric characteristic of liquid crystal.
Figure 4:
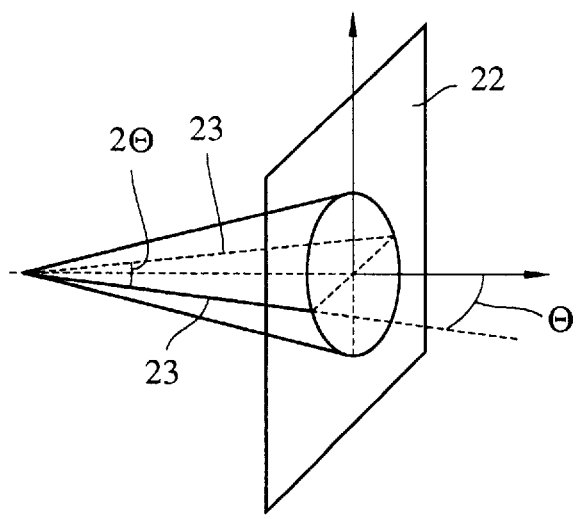
FIG. 4 illustrates tilt angle (θ) of a liquid crystal molecule.

The thickness of the liquid crystal cell for use preferably in the optical modulating device according to the present invention can be reduced satisfactorily (for example, 10 μm or thinner). As the liquid crystal layer is thinned as described above, the spiral structures of the liquid crystal molecules are untied as shown in FIG. 3 even if no electric field is applied. As a result, the dipole moment Pa or Pb is brought into an upward direction 34a or a downward direction 34b. When an electric field Ea or Eb larger than a predetermined threshold is, as shown in FIG. 3, applied to a cell of the foregoing type by voltage applying means 31a and 31b, the dipole moments change their direction to the upward direction 34a or the downward direction 34b to correspond to the electric field vector. Correspondently, the liquid crystal molecules are oriented to a first stable state 33a or a second stable state 33b.

Use of the ferroelectric liquid crystal device as the optical modulating device enables two advantages as described above. The first advantage is that a very first response speed can be obtained. The second advantage is that the liquid crystal molecules have the bistability. The second advantage will now be described with reference to FIG. 3. When the electric field Ea is applied, the direction of the liquid crystal molecules are changed so as to be oriented into the second stable state 33b. Even if the electric field is turned off, the liquid crystal molecules are maintained at the foregoing state. If the applied electric field Ea or Eb does not exceed a predetermined threshold, the previous state of orientation is maintained.

Figure 5B:
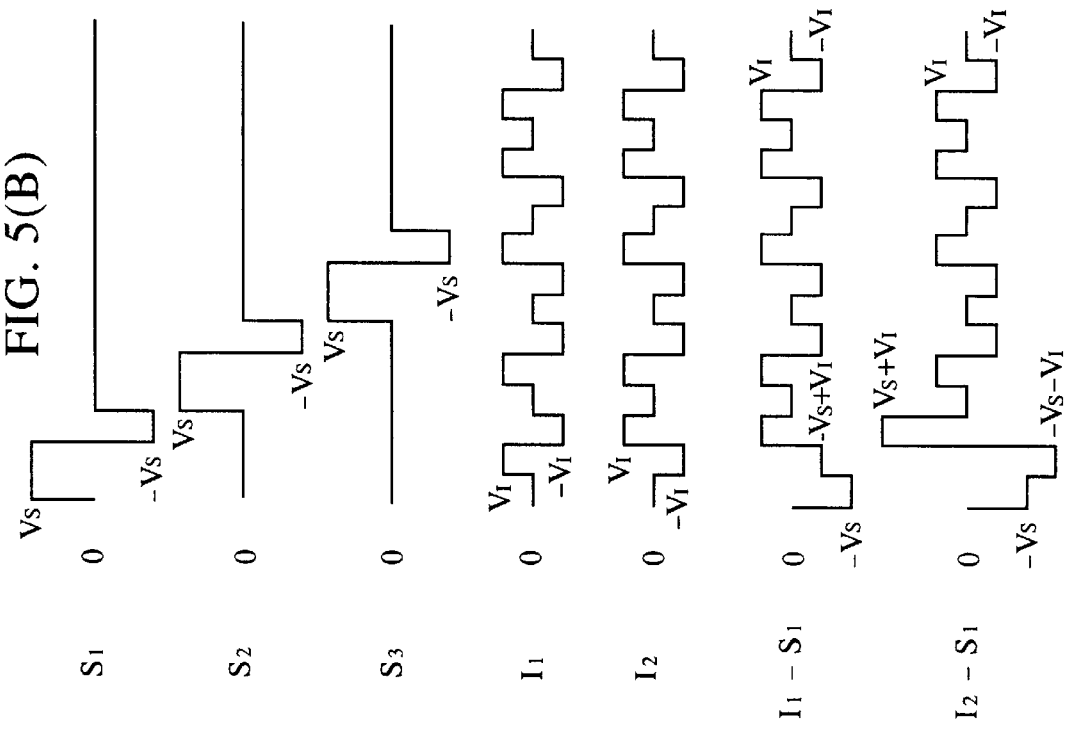
FIGS. 5(A) and 5(B) show waveforms in a method of operating the liquid crystal device according to the present invention.
Figure 5A:
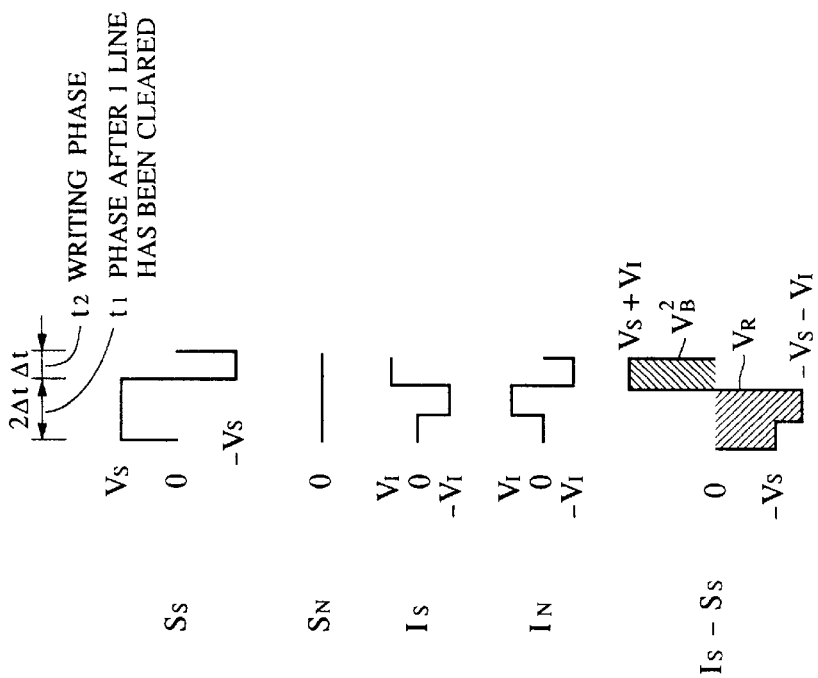

FIG. 5 illustrates operation waveforms according to the present invention. Referring to FIG. 5(A), symbols $S_S$ represent selected scanning waveforms to be applied to selected scanning lines, $S_N$ represent non-selected scanning waveforms to be applied to non-selected scanning lines, $I_S$ represent selected information waveform (black) to be applied to selected data lines and $I_N$ represent non-selected information signal (white) to be applied to non-selected data lines. Referring to FIG. 5(A), ($I_S$–$S_S$) and ($I_N$–$S_S$) represent voltage waveforms to be applied to pixels on the selected scanning lines. Pixels applied with voltage ($I_S$–$S_S$) are brought into a black display state, while pixels applied with voltage ($I_N$–$S_S$) are brought into a white display state.

Figure 6:
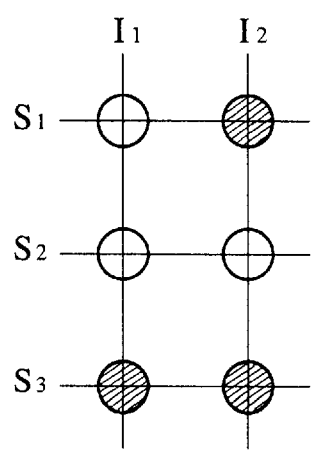
FIG. 6 is a schematic view which illustrates a display pattern to be performed when an actual operation is performed with the time sequential operation waveforms shown in FIG. 5.

FIG. 5(B) illustrates time-sequential waveforms realized when display shown in FIG. 6 is performed with the operation waveforms shown in FIG. 5(A). In the example of the operation shown in FIG. 5, shortest applying time Δt, in which the pixel on the selected scanning line is applied with monopole voltage, corresponds to the time of writing phase $t_2$. The time $t_1$ for clearing one line is set to 2Δt. The values of the respective parameters $V_S$, $V_I$ and Δt of the operation waveforms shown in FIG. 5 are determined depending upon the switching characteristic of the employed liquid crystal material. In this embodiment, determination is fixed such that $V_I/(V_I+V_S)=\frac{1}{3}$. Although the range of the adequate operating voltage can be widened by raising the bias ratio, the raise of the bias ratio causes the amplitude of the information signal to be widened and thus the image quality deteriorates such that flickers take place and the contrast is lowered. Investigations performed by the inventors of the present invention resulted in that the practical bias ratio is 1/3 to 1/4.

The liquid crystal device according to the present invention may be adequately combined with another device or a circuit to constitute a variety of liquid crystal devices.

Figure 8:
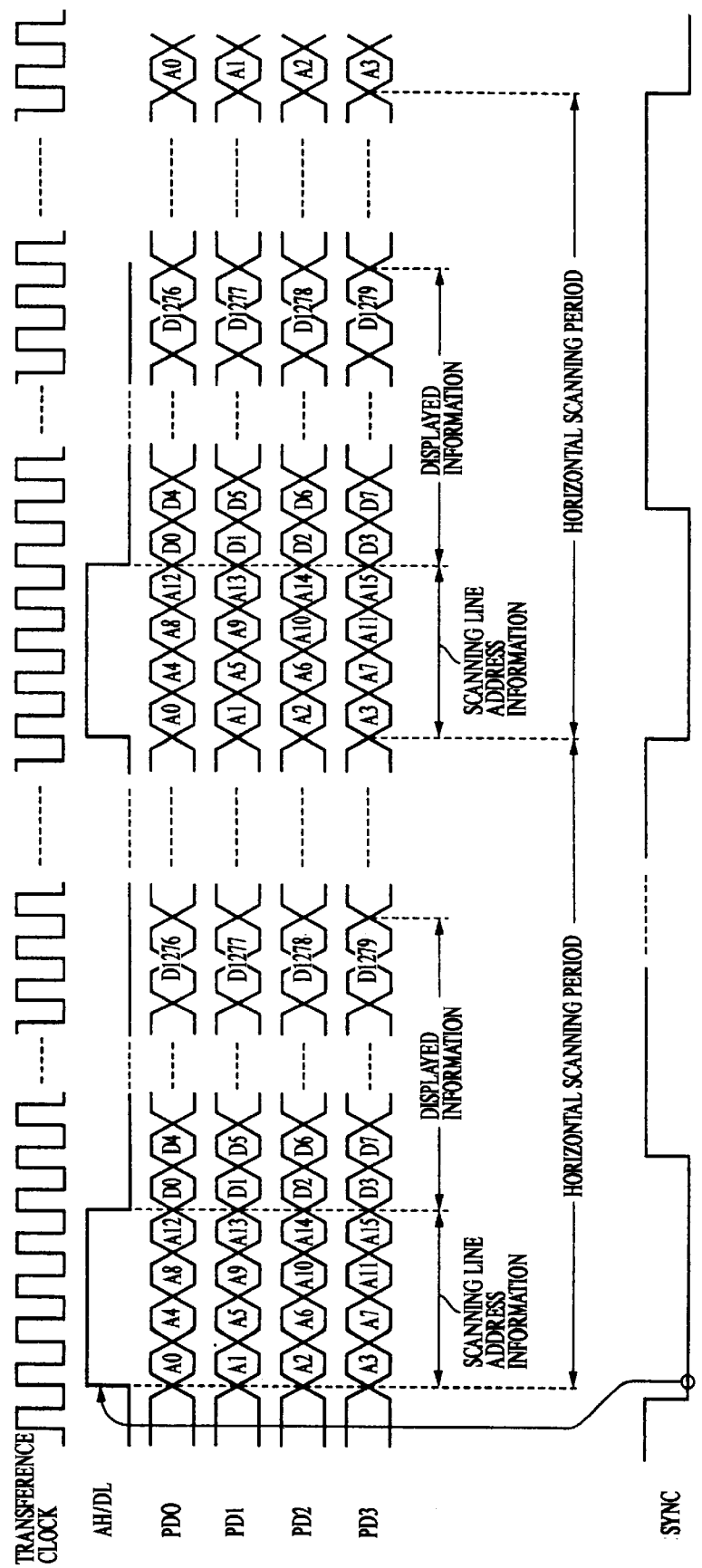
FIG. 8 is a timing chart of image information communication between the liquid crystal display apparatus and the graphic controller.

In particular, the liquid crystal device according to the present invention is used in a display panel portion and a communication synchronizing means is provided so that a liquid crystal display apparatus is realized, the communication synchronizing means being adapted to a data format composed of image information having the scanning address information shown in FIGS. 7 and 8 and a SYNC signal.

Referring to FIGS. 7 and 8, reference numeral 101 represents a liquid crystal display apparatus, 102 represents a graphic controller, 103 represents a display panel, 104 represents a scanning line operating circuit, 105 represents an information line operating circuit, 106 represents a decoder, 107 represents a scanning signal generating circuit, 108 represents a shift register, 109 represents a line memory, 110 represents an information signal generating circuit, 111 represents an operation control circuit, 112 represents a GCPU, 113 represents a host CPU and 114 represents a VRAM.

Image information is generated by the graphic controller 102 provided for the apparatus body, the image information being transferred to the display panel 103 by a signal transferring means shown in FIGS. 7 and 8. The graphic controller 102 controls image information and communication between the host CPU 113 and the liquid crystal display apparatus 101 depending upon the CPU (central processing unit, hereinafter abbreviated to a "GCPU 112") and the VARM (an image information storage memory) 114. The control method according to the present invention is realized mainly on the graphic controller 102. Note that a light source is disposed on the reverse side of the display panel 103.

Examples of the present invention will now be described in detail. The present invention is not limited to the examples below.

EXAMPLE 1

Preparation of optically active 2-[2-{4-(4-methoxyphenyl) phenyl}ethyl]-4-hexyl-4-butanolyde (Example Compound No. 4)

(1) Preparation of 2-(4-bromophenyl) ethylbenzylether 6.12 g (30.4 mmol) of 4-bromophenthylalcohol, 1.34 g (33.4 mmol) of 60% sodium hydride and 23 ml of tetrahydrofuran (THF) were injected. Then, a mixture solution of 7.84 g (62.0 mol) of benzylchloride and 10 ml of THF were dripped, and the materials were stirred for 2.5 hours while being heated at 80° C. After reactions had been completed, the materials were cooled, and water was added, extraction with toluene, cleaning wit water and drying were performed. The solvent was removed by filtration, and then refining was performed with a silica gel column chromatography (developing solvent: toluene/hexane=⅓) so that 7.0 g of 2-(4-bromophenyl) ethylbenzylether was obtained (yield 79%).

(2) Preparation of 2-{4-(4-methoxyphenyl) phenyl}ethylbenzylether 1.57 g (10.3 mmol) of 4-methoxyphenyl malonic acid, 3.0 g (10.3 mmol) of 2-(4-bromophenyl) ethylbenzylether, 0.38 g of tetrakis (triphenylphosphine) palladium, 15 ml of 2M-sodium carbonate solution, 15 ml of toluene and 10 ml of ethanol were heated at 80° C. for 4 hours under presence of nitrogen. After reactions had been completed, extraction with toluene was performed. Then, the extracted solution was dried with anhydrous sodium sulfate. The solvent was removed by filtration, and then refining was performed with a silica gel column chromatography (developing solvent: toluene) and by recrystallization (ethanol) so that 2.63 g of 2-{4-(4-methoxyphenyl) phenyl}ethylbenzylether was obtained (yield 80%).

(3) Preparation of 2-{4-(4-methoxyphenyl) phenyl}ethanol 2,59 g (7.85 mol) of 2-{4-(4-methoxyphenyl) phenyl}ethylbenzylether, 0.4 g of 5% palladium activated carbon, 70 ml of ethanol and 6 ml of dioxane were injected and stirred at room temperature for 7 hours under presence of hydrogen. After the reactions had been completed, the catalyst was removed by tuck filtration and the solvent was removed by filtration so that 1.64 g of 2-{4-(4-methoxyphenyl) phenyl}ethanol was obtained (yield 92%).

(4) Preparation of 4-toluenesulfonic acid 2-{4-(4-methoxyphenyl) phenyl}ethyl 1.64 g (7.18 mmol) of 2-{4-(4-methoxyphenyl) phenyl}ethanol, 1.44 g (7.54 mmol) of 4-toluenesulfonic acid chloride, 3.20 g (40.5 mmol) of pyridine and 5 ml of dichloromethane were stirred at room temperature for 5 hours. After the reactions had been completed, cooling was performed, 10 ml of 6M-hydrochloric acid was added, extraction with toluene was performed, and the extracted solution was dried with anhydrous sodium sulfate. After the solvent had been removed by filtration, refining was performed with a silica gel column chromatography (developing solvent: toluene) so that 2.37 g of 4-toluenesulfonic acid 2-{4-(4-methoxyphenyl) phenyl}ethyl was obtained (yield 86%).

(5) Preparation of 2-[2-{4-(4-methoxyphenyl) phenyl}ethyl] diethyl malonate 0.29 g (7.3 mmol) of 60% sodium hydrate and 1 ml of N,N-dimethylformamide (DMF) were injected, and mixture solution of 1.07 g (6.7 mol) of dimethyl malonate and 3 ml of DMF were dripped to the foregoing materials. Stirring at room temperature was performed for 15 minutes, and then mixed solution of 2.30 g (6.01 mmol) of 4-toluene sulfonic acid 2-{4-(4-methoxyphenyl) phenyl}ethyl and 5 mol of DMF was dripped, and then heating and stirring at 100° C. were performed for 6 hours. After the reactions had been completed, cooling was performed, water was added and extraction with toluene was performed. Then, cleaning with water and drying were performed. After the solvent was removed by filtration, refining was performed with a silica gel column chromatography (developing solvent: toluene/ ethyl acetate=10/1] so that 1.35 g of 2-[2-{4-(4-methoxyphenyl)phenyl}ethyl]diethyl malonate was obtained.

(6) Preparation of optically active 2-[2-{4-(4-methoxyphenyl) phenyl}ethyl]-4-hexyl-4-butanolyde 0.60 g (1.62 mmol) of 2-[2-{4-(4-methoxyphenyl) phenyl}ethyl]diethyl malonate, 0.20 g (1.78 mmol) of t-butoxy potassium and 5 ml of t-butanol were injected. Then, mixed solution of 0.21 g (1.62 mmol) of optically active 1,2-epoxyoctane and 2 ml of t-butanol was dripped, and then heating and stirring at 90° C. were performed for 4 hours. After the reactions had been completed, 6M-hydrochloric acid was added so that the pH was made to be 1, and extraction with ethyl acetate was performed. After the extracted solution was dried, the solvent was removed by filtration. Then, refining was performed with a silica gel column chromatography (developing solvent: toluene/ethyl acetate=20/1) and by recrystallization (toluene/methanol) so that 0.20 g of optically active 2-[2-{4-(4-methoxyphenyl) phenyl}ethyl]-4-hexyl-4-butanolyde was obtained (yield 32% and melting point 134.8° C.).

EXAMPLE 2

Preparation of optically active 2-[4-{4-(3-fluorononyloxy) phenyl}phenyl]ethyl-4-hexyl-4-butanolyde (Example Compound No. 5)

(1) Preparation of optically active 2-{4-(4-hydroxyphenyl) phenyl}ethyl-4-hexyl-4-butanolyde 0.38 g (1.0 mmol) of optically active 2-{4-(4-methoxyphenyl) phenyl}ethyl-4-hexyl-4-butanolyde and 6 ml of dichloromethane were cooled to −80° C. Then, mixed solution of 0.15 g (1.2 mmol) of boron tribromide and 3 ml of dichloromethane was dripped. Then, stirring was performed at room temperature for 15 hours, and 10 ml of water was added, and extraction with ethyl acetate was performed. The extracted solution was cleaned with solution of sodium hydrogen carbonate, and then it was dried with anhydrous sodium sulfate. After the solvent was removed by filtration, refining was performed with a silica gel column chromatography (developing solvent: toluene/ethyl acetate=10/1) and by recrystallization (toluene/hexane) so that 0.30 g of optically active 2-{4-(4-hydroxyphenyl) phenyl}ethyl-4-hexyl-4-butanolyde was obtained (yield 82%).

(2) Preparation of optically active 2-[4-{4-(3-fluorononyloxy) phenyl}phenyl]ethyl-4-hexyl-4-butanolyde 0.033 g (0.83 mmol) of 60% sodium hydrate and 2 ml of DMF were injected, and a mixed solution of 0.29 g (0.79 mol) of optically active 2-{4-(4-hydroxyphenyl) phenyl}ethyl-4-hexyl-4-butanolyde and 3 ml of DMF was dripped. Stirring was performed at room temperature for 15 minutes, and then a mixed solution of 0.26 g (0.82 mmol) of 4-toluene sulfonic acid 3-fluorononyl and 2 ml of DMF was dripped. Then, heating and stirring at 60° C. were performed for one hour. After the reactions had been completed, cooling was performed, water and methanol were added. Then, precipitated crystal was filtered. The obtained crystal was cleaned with water and methanol. Then, refining was performed with a silica gel column chromatography (developing solvent: toluene/ethyl acetate=10/1) and by recrystallization so that 0.32 g of 2-[4-{4-(3-fluorononyloxy) phenyl}phenyl]ethyl-4-hexy-4-butanolyde was obtained (yield 80% and melting point 129.7° C.).

EXAMPLE 3

Preparation of optically active 2-[2-{4-(2-octylindane-5-yl) phenyl}ethyl]-4-octyl-4-butanolyde (Example Compound No. 47)

(1) Preparation of 2-{4-(2-octylindane-5-yl) phenyl}ethanol 2.74 g (10.0 mmol) of 2-octylindane-5-boronic acid, 2.0 g (10.0 mmol) of 2-(4-bromophenyl) ethanol, 0.38 g of tetrakis (triphenylphosphine) palladium, 15 ml of 2M-sodium carbonate solution, 15 ml of toluene and 10 ml of ethanol were heated at 80° C. for 6 hours under presence of nitrogen. After reactions had been completed, extraction with toluene was performed. Then, the extracted solution was dried with anhydrous sodium sulfate. The solvent was removed by filtration, and then refining was performed by re-crystallization (hexane/ethanol) so that 2.40 g of 2-{4-(2-octylindane-5-yl) phenyl}ethanol was obtained (yield 68%).

(2) Preparation of 4-toluene sulfonic acid 2-{4-(2-octylindane-5-yl) phenyl}ethyl 2.40 g (6.85 mmol) of 2-{4-(2-octylindane-5-yl) phenyl}ethanol, 1.31 g (6.85 mmol) of 4-toluenesulfonic acid chloride and 3.20 g (40.5 mmol) of pyridine were stirred at room temperature for 3 hours. After the reactions had been completed, cooling was performed, 10 ml of 6M-hydrochloric acid was added, extraction with toluene was performed, and the extracted solution was dried with anhydrous sodium sulfate. After the solvent had been removed by filtration, refining was performed with a silica gel column chromatography (developing solvent: toluene) so that 2.70 g of 4-toluene sulfonic acid 2-{4-(2-octylindane-5-yl) phenyl}ethyl was obtained (yield 78%).

(3) Preparation of 2-[2-{4-(2-octylindane-5-yl) phenyl}ethyl]diethyl malonate 0.23 g (5.67 mmol) of 60% sodium hydrate and 1 ml of DMF were injected, and mixture solution of 0.91 g (5.67 mol) of dimethyl malonate and 3 ml of DMF were dripped to the foregoing materials. Stirring at room temperature was performed for 15 minutes, and then mixed solution of 2.60 g (5.15 mmol) of 4-toluene sulfonic acid 2-{4-(2-octylindane-5-yl)phenyl}ethyl and 5 ml of DMF was dripped, and then heating and stirring at 90° C. were performed for 4 hours. After the reactions had been completed, cooling was performed, water was added and extraction with toluene was performed. Then, cleaning with water and drying were performed. After the solvent was removed by filtration, refining was performed with a silica gel column chromatography (developing solvent: toluene/ ethyl acetate=10/1] so that 1.52 g of 2-[2-{4-(2-octylindane-5-yl) phenyl}ethyl]diethyl malonate was obtained (yield 60%).

(4) Preparation of optically active 2-[2-{4-(2-octylindane-5-yl) phenyl}ethyl]-4-octyl-4-butanolyde 0.70 g (1.40 mmol) of 2-[2-{4-(2-octylindane-5-yl) phenyl}ethyl]diethyl malonate, 0.17 g (1.56 mmol) of t-butoxy potassium and 8 ml of t-butanol were injected. Then, mixed solution of 0.22 g (1.42 mmol) of 1,2-epoxydecane and 4 ml of t-butanol was dripped, and then heating and stirring at 90° C. were performed for 8 hours. After the reactions had been completed, 6M-hydrochloric acid was added so that the pH was made to be 1, and extraction with ethyl acetate was performed. After the extracted solution was dried, the solvent was removed by filtration. Then, refining was performed with a silica gel column chromatography (developing,solvent: toluene/ethyl acetate=20/1) and by recrystallization (toluene/methanol) so that 0.30 g of optically active 2-[2-{4-(2-octylindane-5-yl) phenyl}ethyl]-4-octyl-4-butanolyde was obtained (yield 40%).

Phase Transition Temperature (°C.)

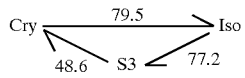

EXAMPLE 4-1

Preparation of optically active 2-[2-{4-(5-decylpyrimidine-2-yl) phenyl}ethyl]-4-hexyl-4-butanolyde (Example Compound No. 19)

(1) Preparation of 4-(2-benzyloxyethyl) phenyl boronic acid 3.8 g (13.0 mmol) of 4-(2-benzyloxyethyl) phenylbromide and 30 ml of dry THF were cooled to −80° C., and 9.4 ml of n-butyllithium (1.65M) was dripped to it. Stirring at the foregoing temperature was performed for 3 hours, and then mixture solution of 5.68 g (30.2 mmol) of triisopropoxyboron and 15 ml of dry THF was dripped, and stirring at room temperature was performed for 13 hours. After the reactions had been completed, 15 ml of 10% hydrochloric acid was added, and extraction with ethyl acetate was performed. After the extracted solution was dried, the solvent was removed by filtration. Then, refining was performed with a silica gel column chromatography (developing solvent: toluene/ethyl acetate=20/1) so that 3.21 g of 4-(2-benzyloxyethyl) phenyl boronic acid was obtained (yield 64%).

(2) Preparation of 2-{4-(5-decylpyrimidine-2-yl) phenyl}ethylbenzylether 1.27 g (4.96 mmol) of 4-(2-benzyloxyethyl) phenylboronic acid, 1.26 g (4.96 mmol) of 2-chloro-5-decylpyrimidine, 0.19 g of tetrakis (triphenylphosphine) palladium, 8 ml of 2M sodium carbonate, 8 ml of toluene and 4 ml of ethanol were, under presence of nitrogen, heated at 80° C. for 3 hours. After the reactions had been completed, extraction with toluene was performed and the extracted solution was dried with anhydrous sodium sulfate. The solvent was removed by filtration and refining was performed by recrystallization (toluene/methanol) so that 1.65 g of 2-{4-(5-decylpyrimidine-2-yl) phenyl}ethylbenzylether was obtained (yield 77%).

(3) Preparation of acetic acid 2-{4-(5-decylpyrimidine-2-yl) phenyl}ethyl 1.00 g (2.32 mmol) of 2-{4-(5-decylpyrimidine-2-yl) phenyl}ethylbenzylether, 0.036 g (0.116 mmol) of 90% tin bromide, 0.71 g (5.81 mmol) of bromide acetate and 10 ml of dichloromethane were stirred at room temperature for 48 hours. After the reactions had been completed, 3M sodium hydrate solution was added to neutralize it. Then, extraction with dichloromethane was performed. The extracted solution was dried with anhydrous sodium sulfate and the solvent was removed by filtration so that 1.49 g of rough acetic acid 2-{4-(5-decylpyrimidine-2-yl) phenyl}ethyl was obtained.

(4) Preparation of 2-{4-(5-decylpyrimidine-2-yl) phenyl}ethanol 1.49 g of rough acetic acid 2-{4-(5-decylpyrimidine-2-yl) phenyl}ethyl, 0.40 g (10 mmol) of sodium hydrate and 20 ml of ethanol were heated and stirred at 90° C. for one hour. After the reactions had been completed, the solvent was removed by filtration, and 3M hydrochloric acid was added so as to be neutralized and extraction with ethyl acetate was performed. The extracted solution was dried with anhydrous sodium sulfate, and then the solvent was removed by filtration. Then, refining was performed with a silica gel column chromatography (developing solvent: toluene/ethyl acetate= 20/1) so that 0.65 g of 2-{4-(5-decylpyrimidine-2-yl) phenyl}ethanol was obtained (total yield from benzylether derivative 82%).

(5) Preparation of 4-toluene sulfonic acid 2-{4-(5-decylpyrimidine-2-yl) phenyl}ethyl 0.65 g (1.91 mmol) of 2-{4-(5-decylpyrimidine-2-yl) phenyl}ethanol, 0.36 g (1.91 mmol) of 4-toluene sulfonic acid chloride and 1.00 g (12.7 mmol) of pyridine were stirred at room temperature for 4 hours. After the reactions had been completed, cooling was performed, 10 ml of 6M hydrochloric acid was added, extraction with toluene was performed and the extracted solution was dried with anhydrous sodium sulfate. The solvent was removed by filtration, and then refining was performed with a silica gel column chromatography (developing solvent: toluene) so that 0.87 g of 4-toluene sulfonic acid 2-{4-(5-decylpyrimidine-2-yl) phenyl}ethyl was obtained (yield 92%).

(6) Preparation of 2-[2-{4-(5-decylpyrimidine-2-yl) phenyl}ethyl]diethyl malonate 0.09 g (2.29 mmol) of 60% sodium hydrate and 0.3 ml of DMF were injected, and mixture solution of 0.32 g (2.00 mol) of dimethyl malonate and 1 ml of DMF was dripped to the foregoing materials. Stirring at room temperature was performed for 15 minutes, and then mixed solution of 0.87 g (1.76 mmol) of 4-toluene sulfonic acid 2-{4-(5-decylpyrimidine-2-yl) phenyl}ethyl and 2 ml of DMF was dripped, and then heating and stirring at 90° C. were performed for 5 hours. After the reactions had been completed, cooling was performed, water was added and extraction with toluene was performed. Then, cleaning with water and drying were performed. After the solvent was removed by filtration, refining was performed with a silica gel column chromatography (developing solvent: toluene/ethyl acetate=20/1] so that 0.43 g of 2-[2-{4-(5-decylpyrimidine-2-yl) phenyl}ethyl]diethyl malonate was obtained (yield 51%).

(7) Preparation of optically active 2-[2-{4-(5-decylpyrimidine-2-yl) phenyl}ethyl]-4-hexyl-4-butanolyde 0.43 g (0.89 mmol) of 2-[2-{4-(5-decylpyrimidine-2-yl) phenyl}ethyl]diethyl malonate, 0.11 g (0.98 mmol) of t-butoxypotassium and 4 ml of t-butanol were injected. Then, mixed solution of 0.11 g (0.89 mmol) of optically active 1,2-epoxyoctane and 2 ml of t-butanol was dripped, and heating and stirring at 90° C. were performed for 3 hours. After the reactions had been completed, 6M hydrochloric acid was added to make the pH to be 1, and extraction with ethyl acetate was performed. The extracted solution was dried, and the solvent was removed by filtration, and then refining was performed with a silica gel column chromatography (developing solvent: toluene/ethyl acetate=20/1) so that 0.03 g of optically active 2-[2-{4-(5-decylpyrimidine-2-yl) phenyl}ethyl]-4-hexyl-4-butanolyde was obtained (yield 7% and melting point 66.3° C.).

EXAMPLE 4-2

Preparation of optically active 2-[2-{4-(5-decylpyrimidine-2-yl) phenyl}ethyl]-4-hexyl-4-butanolyde (Example Compound No. 19) <Fine adjustment of conditions for Example 4-1>

(1) Preparation of 4-(2-benzyloxyethyl) phenyl boronic acid 13.7 g (47.1 mmol) of 4-(2-benzyloxyethyl) phenylbromide and 80 ml of dry THF were cooled to −75° C., and 34.0 ml of n-butyllithium (1.65M) was dripped to it. Stirring at the foregoing temperature was performed for 3 hours, and then mixture solution of 12.9 g (68.7 mmol) of triisopropoxyboron and 50 ml of dry THF was dripped, and stirring at −75° C. was performed for 2 hours and that at room temperature was performed for 14 hours. After the reactions had been completed, 50 ml of 10% hydrochloric acid was added, and extraction with ethyl acetate was performed. After the extracted solution was dried, the solvent was removed by filtration. Then, refining was performed with a silica gel column chromatography (developing solvent: toluene/ethyl acetate=20/1) so that 8.62 g of 4-(2-benzyloxyethyl) phenyl boronic acid was obtained (yield 71%).

(2) Preparation of 2-{4-(5-decylpyrimidine-2-yl) phenyl}ethylbenzylether 1.27 g (4.96 mmol) of 4-(2-benzyloxyethyl) phenylboronic acid, 1.26 g (4.96 mmol) of 2-chloro-5-decylpyrimidine, 0.19 g of tetrakis (triphenylphosphine) palladium, 8 ml of 2M sodium carbonate, 8 ml of toluene and 4 ml of ethanol were, under presence of nitrogen, heated at 80° C. for 3 hours. After the reactions had been completed, extraction with toluene was performed and the extracted solution was dried with anhydrous sodium sulfate. The solvent was removed by filtration and refining was performed by recrystallization (toluene/methanol) so that 1.65 g of 2-{4-(5-decylpyrimidine-2-yl) phenyl}ethylbenzylether was obtained (yield 77%).

(3) Preparation of acetic acid 2-{4-(5-decylpyrimidine-2-yl) phenyl}ethyl 1.00 g (2.32 mmol) of 2-{4-(5-decylpyrimidine-2-yl) phenyl}ethylbenzylether, 0.036 g (0.116 mmol) of 90% tin bromide, 0.71 g (5.81 mmol) of bromide acetate and 10 ml of dichloromethane were stirred at room temperature for 48 hours. After the reactions had been completed, 3M sodium hydrate solution was added to neutralize it. Then, extraction with dichloromethane was performed. The extracted solution was dried with anhydrous sodium sulfate and the solvent was removed by filtration so that 1.49 g of rough acetic acid 2-{4-(5-decylpyrimidine-2-yl) phenyl}ethyl was obtained.

(4) Preparation of 2-{4-(5-decylpyrimidine-2-yl) phenyl}ethanol 1.49 g of rough acetic acid 2-{4-(5-decylpyrimidine-2-yl) phenyl}ethyl, 0.40 g (10 mmol) of sodium hydrate and 20 ml of ethanol were heated and stirred at 90° C. for one hour. After the reactions had been completed, the solvent was removed by filtration, and 3M hydrochloric acid was added so as to be neutralized and extraction with ethyl acetate was performed. The extracted solution was dried with anhydrous sodium sulfate, and then the solvent was removed by filtration. Then, refining was performed with a silica gel column chromatography (developing solvent: toluene/ethyl acetate=20/1) so that 0.65 g of 2-{4-(5-decylpyrimidine-2-yl) phenyl}ethanol was obtained (total yield from benzylether derivative 82%).

(5) Preparation of 4-toluene sulfonic acid 2-{4-(5-decylpyrimidine-2-yl) phenyl}ethyl 0.65 g (1.91 mmol) of 2-{4-(5-decylpyrimidine-2-yl) phenyl}ethanol, 0.36 g (1.91 mmol) of 4-toluene sulfonic acid chloride and 1.00 g (12.7 mmol) of pyridine were stirred at room temperature for 4 hours. After the reactions had been completed, cooling was performed, 10 ml of 6M hydrochloric acid was added, extraction with toluene was performed and the extracted solution was dried with anhydrous sodium sulfate. The solvent was removed by filtration, and then refining was performed with a silica gel column chromatography (developing solvent: toluene) so that 0.87 g of 4-toluene sulfonic acid 2-{4-(5-decylpyrimidine-2-yl) phenyl}ethyl was obtained (yield 92%).

(6) Preparation of 2-[2-{4-(5-decylpyrimidine-2-yl) phenyl}ethyl]diethyl malonate 0.30 g (7.52 mmol) of 60% sodium hydrate and 5 ml of DMF were injected, and mixture solution of 1.26 g (7.85 mol) of dimethyl malonate and 2 ml of DMF was dripped to the foregoing materials. Stirring at room temperature was performed for 15 minutes, and then mixed solution of 3.38 g (6.83 mmol) of 4-toluene sulfonic acid 2-{4-(5-decylpyrimidine-2-yl) phenyl}ethyl and 10 ml of DMF was dripped, and then heating and stirring at 90° C. were performed for 7 hours. After the reactions had been completed, cooling was performed, water was added and extraction with toluene was performed. Then, cleaning with water and drying were performed. After the solvent was removed by filtration, refining was performed with a silica gel column chromatography (developing solvent: toluene/ethyl acetate=20/1] so that 2.49 g of 2-[2-{4-(5-decylpyrimidine-2-yl) phenyl}ethyl]diethyl malonate was obtained (yield 76%).

(7) Preparation of optically active 2-[2-{4-(5-decylpyrimidine-2-yl) phenyl}ethyl]-4-hexyl-4-butanolyde 1.93 g (4.0 mmol) of 2-[2-{4-(5-decylpyrimidine-2-yl) phenyl}ethyl]diethyl malonate, 0.55 g (4.4 mmol) of t-butoxypotassium and 15 ml of t-butanol were injected. Then, mixed solution of 0.62 g (4.8 mmol) of optically active (R)-1,2-epoxyoctane and 6 ml of t-butanol was dripped, and heating and stirring at 90° C. were performed for 6 hours. After the reactions had been completed, 6M hydrochloric acid was added to make the pH to be 1, and extraction with ethyl acetate was performed. The extracted solution was dried, and the solvent was removed by filtration, and then refining was performed with a silica gel column chromatography (developing solvent: toluene/ethyl acetate=20/1) and by recrystallization (once with hexane/ethyl acetate and once hexane/isopropanol) so that 0.69 g of optically active 2-[2-{4-(5-decylpyrimidine-2-yl) phenyl}ethyl]-4-hexyl-4-butanolyde (mixture ratio of cis/trans=83/17) was obtained (yield 35% and melting point 66.3° C.).

EXAMPLE 5-1
Preparation of optically active 2-(5-hexenyl)-4-hexyl-4-butanolyde (Example Compound No. 513)
(1) Preparation of 2-(5-hexenyl) diethyl malonate
0.59 g (14.7 mmol) of 60% sodium hydrate and 5 ml of DMF were injected, and mixed solution of 2.36 g (14.7 mol) of dimethyl malonate 5 ml of DMF was dripped. Stirring at room temperature was performed for 15 minutes, and then mixed solution of 2.04 g (12.3 mol) of 6-bromo-1-hexene and 5 ml of DMF was dripped. Then, heating and stirring at 90° C. were performed for 6 hours. After the reactions had been completed, water was added, extraction with ethyl acetate was performed, and cleaning with water and drying were performed. After the solvent had been removed, distillation under reduced pressure was performed so that 2.78 g of 2-(5-hexenyl) diethyl malonate was obtained (yield 93% and melting point 100° C. to 110° C./6 torr).
(2) Preparation of optically active 2-(5-hexenyl)-4-hexyl-4-butanolyde
2.30 g (9.5 mmol) of 2-(5-hexenyl) diethyl malonate, 1.30 g (10.4 mmol) of t-butoxypotassium and 20 ml of t-butanol were injected. Then, mixed solution of 1.22 g (9.5 mmol) of optically active 1,2-epoxyoctane and 6 ml of t-butanol was dripped, and heating and stirring at 90° C. were performed for 5 hours. After the reactions had been completed, 6M hydrochloric acid was added to make the pH to be 1, and extraction with ethyl acetate was performed. The extracted solution was dried, and the solvent was removed by filtration, and then refining was performed with a silica gel column chromatography (developing solvent: toluene) so that 1.37 g of optically active 2-(5-hexenyl)-4-hexyl-4-butanolyde was obtained (yield 48%).

EXAMPLE 5-2
Preparation of 2-[6-{4-(5-decylpyrimidine-2-yl) phenyl}hexyl]-4-hexyl-4-butanolyde (Example Compound No. 124)
0.80 g (2.66 mmol) of optically active 2-(5-hexenyl)-4-hexyl-4-butanolyde (Example Compound No. 513) and 3 ml of THF were injected, and they were cooled to –17° C. Then, 6.4 ml of 9-borabicyclo [3.3.1]nonane (0.5M THF solution) was dripped, and stirring at 0° C. was performed for one hour. Then, stirring at room temperature was performed for one hour, and then 0.08 g (0.073 mmol) of tetrakis (triphenylphosphine) palladium, 1.00 g (2.66 mmol) of 5-decyl-2-(4-bromophenyl) pyrimidine, 10 ml of DMF, and 0.74 g (5.32 mmol) of potassium carbonate were added, and stirring at 60° C. was performed for 5 hours. After reactions had been completed, water was added, and extraction with ethyl acetate was performed. The extracted solution was dried, and then the solvent was removed by filtration. Then, refining was performed with a silica gel column chromatography (developing solvent: toluene/ethyl acetate=50/1) and by recrystallization (hexane/ethyl acetate) so that 0.32 g of 2-[6-{4-(5-decylpyrimidine-2-yl) phenyl}hexyl]-4-hexyl-4-butanolyde was obtained (yield 22% and melting point 64.3° C.).

EXAMPLE 6
Preparation of optically active 2-[2-{4-(2-octylindane-5-yl) phenyl}ethyl]-4-phenyl-4-butanolyde (Example Compound No. 257)
0.70 g (1.40 mmol) of 2-[2-{4-(2-octylindane-5-yl) phenyl}ethyl]diethyl malonate, 0.17 g (1.56 mmol) of t-butoxypotassium and 8 ml of t-butanol were injected. Then, mixed solution of 0.17 g (1.42 mmol) of optically active styrene oxide and 4 ml of t-butanol was dripped, and heating and stirring at 90° C. were performed for 3 hours. After the reactions had been completed, 6M hydrochloric acid was added to make the pH to be 1, and extraction with ethyl acetate was performed. The extracted solution was dried, and the solvent was removed by filtration, and refining was performed with a silica gel column chromatography (developing solvent: toluene) and by recrystallization (toluene/methanol) so that 0.08 g of optically active 2-[2-{4-(2-octylindane-5-yl) phenyl}ethyl]-4-phenyl-4-butanolyde was obtained (yield 11% and melting point 96.9° C.).

EXAMPLE 7
Preparation of optically active 2-[2-{4-(2-octylindane-5-yl) phenyl}ethyl]-4-(4-methoxyphenyl)-4-butanolyde (Example Compound No. 468)
0.70 g (1.40 mmol) of 2-[2-{4-(2-octylindane-5-yl) phenyl}ethyl]diethyl malonate, 0.17 g (1.56 mmol) of t-butoxypotassium and 8 ml of t-butanol were injected. Then mixed solution of 0.21 g (1.42 mmol) of optically active 4-methoxystyreneoxide and 4 ml of t-butanol was dripped, and heating and stirring at 90° C. were performed for 3 hours. After the reactions had been completed, 6M hydrochloric acid was added to make the pH to be 1, and extraction with ethyl acetate was performed. The extracted solution was dried, and the solvent was removed by filtration, and refining was performed with a silica gel column chromatography (developing solvent: toluene) and by recrystallization (toluene/methanol) so that 0.05 g of optically active 2-[2-{4-(2-octylindane-5-yl) phenyl}ethyl]-4-(4-methoxyphenyl)-4-butanolyde was obtained (yield 7% and melting point 140.7° C.).

EXAMPLE 8
Preparation of optically active 2-[2-{4-(5-decylpyrimidine-2-yl) phenyl}ethyl]-4-phenyl-4-butanolyde (Example Compound No. 229)
0.50 g (1.04 mmol) of 2-[2-{4-(5-decylpyrimidine-2-yl) phenyl}ethyl]diethyl malonate, 0.13 g (1.14 mmol) of t-butoxypotassium and 3 ml of t-butanol were injected. Then, mixed solution of 0.15 g (1.25 mmol) of optically active styreneoxide and 2 ml of t-butanol was dripped, and heating and stirring at 90° C. were performed for 3 hours. After the reactions had been completed, 6M hydrochloric acid was added to make the pH to be 1, and extraction with ethyl acetate was performed. After the extracted solution was dried, and the solvent was removed by filtration. Then, refining was performed with a silica gel column chromatography (developing solvent: toluene/ethyl acetate=10/1) and by recrystallization (methanol) so that 0.09 g of optically active 2-[2-{4-(5-decylpyrimidine-2-yl) phenyl}ethyl]-4-phenyl-4-butanolyde was obtained (yield 18% and melting point 79.5° C.).

EXAMPLE 9
Preparation of optically active 2-methyl-4-[8-{4-(5-decylpyrimidine-2-yl) phenyl}octyl]-4-butanolyde (Example Compound No. 476)

(1) Preparation of optically active 1,2-epoxy-8-{4-(5-decylpyrimidine-2-yl) phenyl}decane 1.36 g (8.8 mmol) of optically active 1,2-epoxy-9-decene and 6 ml of THF were injected, and they were cooled to −17° C. Then, 9-borabicyclo [3.3.1]nonane (0.5M THF solution) was dripped, and stirring at 0° C. was performed for one hour. Then, stirring at room temperature was performed for one hour, and then 0.26 g (0.073 mmol) of tetrakis (triphenylphosphine) palladium, 3.00 g (8.00 mmol) of 5-decyl-2-(4-bromophenyl) pyrimidine, 10 ml of DMF, and 2.21 g (16.0 mmol) of potassium carbonate were added, and stirring at 60° C. was performed for 5 hours. After reactions had been completed, water was added, and extraction with ethyl acetate was performed. The extracted solution was dried, and then the solvent was removed by filtration. Then, refining was performed with a silica gel column chromatography (developing solvent: toluene/ethyl acetate=50/1) and by recrystallization (toluene/methanol) so that 2.10 g of 1,2-epoxy-8-{4-(5-decylpyrimidine-2-yl) phenyl}decane was obtained (yield 58%).

(2) Preparation of optically active 2-methyl-4-[8-{4-(5-decylpyrimidine-2-yl) phenyl}octyl]-4-butanolyde 0.39 g (2.22 mmol) of 2-methyl diethyl malonate, 0.31 g (2.44 mmol) of t-butoxypotassium and 5 ml of t-butanol were injected. Then, mixed solution of 1.00 g (2.22 mmol) of optically active compound 1,2-epoxy-8-{4-(5-decylpyrimidine-2-yl) phenyl}decane and 6 ml of t-butanol was dripped, and then heating and stirring at 90° C. were performed for 4 hours. After the reactions had been completed, 6M-hydrochloric acid was added so that the pH was made to be 1, and extraction with ethyl acetate was performed. After the extracted solution was dried, the solvent was removed by filtration. Then, refining was performed with a silica gel column chromatography (developing solvent: hexane/ethyl acetate=10/1) and by recrystallization (methanol) so that 0.30 g of optically active 2-methyl-4-[8-{4-(5-decylpyrimidine-2-yl) phenyl}octyl]-4-butanolyde was obtained (yield 27% and melting point 76.4° C.).

EXAMPLE 10

Preparation of optically active 2-[2-{4-(5-decyloxypyrimidine-2-yl) phenyl}ethyl]-4-hexyl-4-butanolyde (Example Compound No. 483)

(1) Preparation of 2-{4-(5-decyloxypyrimidine-2-yl) phenyl}ethylbenzylether 8.62 g (33.7 mmol) of 4-(2-benzyloxyethyl) phenyl boronic acid, 9.13 g (33.7 mmol) of 2-chloro-5-decyloxypyrimidine, 1.29 g of tetrakis (triphenylphosphine) palladium, 54 ml of 2M-sodium carbonate solution, 54 ml of toluene and 27 ml of ethanol were heated at 80° C. for 4 hours under presence of nitrogen. After reactions had been completed, extraction with toluene was performed. Then, the extracted solution was dried with anhydrous sodium sulfate. The solvent was removed by filtration, and then refining was performed by recrystallization (toluene/methanol) so that 9.30 g of 2-{4-(5-decyloxypyrimidine-2-yl) phenyl}ethylbenzylether was obtained (yield 62%).

(2) Preparation of acetic acid 2-{4-(5-decyloxypyrimidine-2-yl) phenyl}ethyl 9.30 g (20.8 mmol) of 2-{4-(5-decyloxypyrimidine-2-yl) phenyl}ethylbenzylether, 0.279 g (0.116 mmol) of 90% tin bromide, 8.0 g (62.4 mmol) of bromide acetate and 50 ml of dichloromethane were stirred at room temperature for 48 hours. After the reactions had been completed, 3M sodium hydrate solution was added to neutralize it, and then extraction with dichloromethane was performed. The extracted solution was dried with anhydrous sodium sulfate, and then the solvent was removed by filtration so that 12.5 g of rough acetic acid 2-{4-(5-decyloxypyrimidine-2-yl) phenyl}ethyl was obtained.

(3) Preparation of 2-{4-(5-decyloxypyrimidine-2-yl) phenyl}ethanol 12.5 g of rough acetic acid 2-{4-(5-decyloxypyrimidine-2-yl) phenyl}ethyl, 3.78 g (89.7 mmol) of sodium hydrate and 100 ml of ethanol were heated and stirred at 90° C. for 3 hours. After the reactions had been completed, the solvent was removed by filtration, and 3M hydrochloric acid was added to neutralize it. Then, extraction with ethyl acetate was performed. The extracted solution was dried with anhydrous sodium sulfate, and then the solvent was removed by filtration. Then, refining was performed with a silica gel column chromatography (developing solvent: toluene/ethyl acetate=10/1) so that 2.0 g of 2-{4-(5-decyloxypyrimidine-2-yl) phenyl}ethanol was obtained (total yield from benzylether derivative 27%).

(4) Preparation of 4-toluene sulfonic acid 2-{4-(5-decyloxypyrimidine-2-yl) phenyl}ethyl 2.0 g (5.6 mmol) of 2-{4-(5-decyloxypyrimidine-2-yl) phenyl}ethanol, 1.07 g (5.6 mmol) of 4-toluene sulfonic acid chloride and 1.2 g (15.0 mmol) of pyridine were stirred at room temperature for 3 hours. After the reactions had been completed, cooling was performed, and 6M hydrochloric acid was added, and extraction with ethyl acetate was performed. Then, the extracted solution was dried with anhydrous sodium sulfate. After the solvent had been removed by filtration, refining was performed with a silica gel column chromatography (developing solvent: toluene) so that 1.68 g of 4-toluene sulfonic acid 2-{4-(5-decyloxypyrimidine-2-yl) phenyl}ethyl was obtained (yield 59%).

(5) Preparation of 2-[2-{4-(5-decyloxypyrimidine-2-yl) phenyl}ethyl]diethyl malonate 0.14 g (3.51 mmol) of 60% sodium hydrate and 3 ml of DMF were injected, and mixed solution of 0.59 g (3.67 mol) of dimethyl malonate and 1 ml of DMF was dripped. Stirring at room temperature was performed for 15 minutes, and mixed solution of 1.63 g (3.19 mmol) of 4-toluene sulfonic acid 2-{4-(5-decyloxypyrimidine-2-yl) phenyl}ethyl and 5 ml of DMF was dripped. Then, heating and stirring at 90° C. was performed for 7 hours. After the reactions had been completed, cooling was performed, water was added, extraction with toluene was performed, cleaning with water and drying were performed. After the solvent had been removed by filtration, refining was performed with a silica gel column chromatography (developing solvent: hexane/ethyl acetate=5/1) so that 0.98 g of -[2-{4-(5-decyloxypyrimidine-2-yl) phenyl}ethyl]diethyl malonate was obtained (yield 62%)

(6) Preparation of optically active 2-[2-{4-(5-decyloxypyrimidine-2-yl) phenyl}ethyl]-4-hexyl-4-butanolyde 0.4 g (0.8 mmol) of 2-[2-{4-(5-decyloxypyrimidine-2-yl) phenyl}ethyl]diethyl malonate, 0.11 g (0.88 mmol) of t-butoxypotassium and 3 ml of t-butanol were injected. Then, mixed solution of 0.12 g (0.97 mmol) of optically active (R)-1,2-epoxyoctane and 1 ml of t-butanol was dripped. Then, heating and stirring at 90° C. were performed for 6 hours. After the reactions had been completed, 6M hydrochloric acid was added to make the pH to be 1, and then extraction with ethyl acetate was performed. The extracted solution was dried, and the solvent was removed by filtration. Then, refining was performed with a silica gel column chromatography (developing solvent: hexane/ethyl acetate=5/1) and by recrystallization (hexane/ethyl acetate) so that 0.1 g of optically active 2-[2-{4-(5- decyloxypyrimidine-2-yl) phenyl}ethyl]-4-hexyl-4-butanolyde (mixture ratio of cis/trans=75/25) was obtained (yield 25% and melting point 73.3° C.).

EXAMPLE 11
Preparation of optically active 2-[6-{4-(5-decyloxypyrimidine-2-yl) phenyl} hexyl]-4-hexyloxymethyl butanolyde (Example Compound No. 501)

0.54 g (1.08 mmol) of 2-[2-{4-(5-decyloxypyrimidine-2-yl) phenyl}ethyl]diethyl malonate, 0.15 g (1.19 mmol) of t-butoxypotassium and 3 ml of t-butanol were injected. Then, mixed solution of 0.21 g (1.30 mmol) of optically active (R)-hexylglycidyl ether and 1 ml of t-butanol was dripped, and then heating and stirring at 90° C. were performed for 4 hours. After the reactions had been completed, 6M hydrochloric acid was added to make pH to be 1, and extraction with ethyl acetate was performed. After the extracted solution had been dried, the solvent was removed by filtration. Then, refining was performed with a silica gel column chromatography (developing solvent: hexane/ethyl acetate=5/1) so that 0.10 g of optically active trans-2-[6-{4-(5-decyloxypyrimidine-2-yl) phenyl}hexyl]-4-hexyloxymethyl butanolyde and 0.08 g of optically active cis-2-[6-{4-(5-decyloxypyrimidine-2-yl) phenyl}hexyl]-4-hexyloxymethyl butanolyde were obtained (melting point of the trans structure 31.1° C. and that of the cis structure 53.3° C.).

EXAMPLE 12
Preparation of optically active 2-(3-butenyl)-4-hexyl-4-butanolyde (Example Compound No. 511)

(1) Preparation of 2-(3-butenyl) diethyl malonate 20 g (870 mmol) of metal sodium and 340 ml of ethanol were injected, and then 112 g (700 mmol) of dimethyl malonate was added. Stirring at room temperature was performed for 15 minutes, and then 97 g (719 mmol) of 4-bromo-1-butene was added. Then, heating and stirring at 90° C. were performed for 15 hours. After the reactions had been completed, ethanol was removed by filtration, and then 500 ml of water was added. Then, extraction with ether was performed, and cleaning with water and drying were performed. After the solvent had been removed by filtration, distillation was performed under reduced pressure so that 112 g of 2-(3-butenyl) diethyl malonate was obtained (yield 58% and melting point 90° C. to 100° C./4 torr).

(2) Preparation of optically active 2-(3-butenyl)-4-hexyl-4-butanolyde 67 g (313 mmol) of 2-(3-butenyl) diethyl malonate, 38.6 g (344 mmol) of t-butoxypotassium and 300 ml of t-butanol were injected. Then, 40 g (313 mmol) of optically active (R)-1,2-epoxyoctane was dripped, and then heating and stirring at 90° C. were performed for 20 hours. After the reactions had been completed, 6M hydrochloric acid was added to make the pH to be 1. Then, extraction with ethyl acetate was performed, and the extracted solution was dried. Then, the solvent was removed by filtration and refining was performed by distillation under reduced pressure and by a silica gel column chromatography (developing solvent: hexane/ethyl acetate=16/1) so that 21.6 g of optically active 2-(3-butenyl)-4-hexyl-4-butanolyde was obtained (yield 31% and melting point 95° C. to 105° C./1 torr).

EXAMPLE 13
Preparation of 2-[4-{4-(5-decylpyrimidine-2-yl) phenyl}butyl]-4-hexyl-4-butanolyde (Example Compound No. 504)

0.72 g (2.66 mmol) of optically active 2-(3-butenyl)-4-hexyl-4-butanolyde and 3 ml of THF were injected, and they were cooled to −17° C. Then, 6.4 ml of 9-borabicyclo [3.3.1]nonane (0.5M THF solution) was dripped, and stirring at 0° C. was performed for one hour. Furthermore, stirring at room temperature was performed for one hour, and then 0.08 g (0.073 mmol) of tetrakis (triphenylphosphine) palladium, 1.00 g (2.66 mmol) of 5-decyl-2-(4-bromophenyl) pyrimidine, 10 ml of DMF and 0.74 g (5.32 mmol) of potassium carbonate were added. Then, they were stirred at 60° C. for 5 hours. After the reactions had been completed, water was added, and extraction with ethyl acetate was performed. After the extracted solution had been dried, the solvent was removed by filtration. Then, refining was performed with a silica gel column chromatography (developing solvent: hexane/ethyl acetate= 50/1) and by recrystallization (once by hexane/ethyl acetate and once by acetone) so that 0.10 g of optically active 2-[4-{4-(5-decylpyrimidine-2-yl) phenyl}butyl]-4-hexyl-4-butanolyde (mixture ratio of cis/trans=97/3) was obtained (yield 7% and melting point 57.2° C.).

EXAMPLE 14
Preparation of optically active 2-(2-propenyl)-4-hexyl-4-butanolyde (Example Compound No. 510)

(1) Preparation of 2-(2-propenyl) diethyl malonate 19 g (826 mmol) of metal sodium and 420 ml of ethanol were injected, and then 135 g (844 mmol) of dimethyl malonate was added. Stirring at room temperature was performed for 15 minutes, and then 100 g (826 mmol) of allylbromide was added. Then, heating and stirring at 90° C. were performed for 15 hours. After the reactions had been completed, ethanol was removed by filtration, and then 500 ml of water was added. Then, extraction with ether was performed, and cleaning with water and drying were performed. After the solvent had been removed by filtration, refining was performed with a silica gel column chromatography (developing solvent: hexane/ethyl acetate 4/1) so that 89 g of 2-(2-propenyl) diethyl malonate was obtained (yield 54%).

(2) Preparation of 2-(2-propenyl)-4-hexyl-4-butanolyde 73 g (365 mmol) of 2-(2-propenyl) diethyl malonate, 44 g (392 mmol) of t-butoxypotassium and 400 ml of t-butanol were injected. Then, 47.4 g (313 mmol) of optically active (R)-1,2-epoxyoctane was dripped, and then heating and stirring at 90° C. were performed for 20 hours. After the reactions had been completed, 6M hydrochloric acid was added to make the pH to be 1. Then, extraction with ethyl acetate was performed, and the extracted solution was dried. Then, the solvent was removed by filtration and refining was performed by distillation under reduced pressure and by a silica gel column chromatography (developing solvent: hexane/ethyl acetate=20/1) so that 2.9 g of optically active trans-2-(2-propenyl)-4-hexyl-4-butanolyde and 17.1 g of optically active cis-2-(2-propenyl)-4-hexyl-4-butanolyde were obtained (yield 26% and melting point 80° C. to 90° C./1 torr).

EXAMPLE 15
Preparation of optically active trans-2-[3-{4-(5-decylpyrimidine-2-yl) phenyl}propyl]-4-hexyl-4-butanolyde (Example Compound No. 505)

0.69 g (2.66 mmol) optically active trans-2-(2-propenyl) -4-hexyl-4-butanolyde and 3 ml of THF were injected, and they were cooled to −17° C. Then, 6.4 ml of 9-borabicyclo [3.3.1]nonane (0.5M THF solution) was dripped, and stirring at 0° C. was performed for one hour. Then, stirring at room temperature was performed for one hour, and then 0.08 g (0.073 mmol) of tetrakis (triphenylphosphine) palladium, 1.18 g (2.66 mmol) of trifuoromethanesulfonic acid 4-(5- decylpyrimidine-2-yl) phenyl, 10 ml of DMF, and 0.74 g (5.32 mmol) of potassium carbonate were added, and stirring at 60° C. was performed for 5 hours. After reactions had been completed, water was added, and extraction with ethyl acetate was performed. The extracted solution was dried, and then the solvent was removed by filtration. Then, refining was performed with a silica gel column chromatography (developing solvent: hexane/ethyl acetate=20/1) and by recrystallization (acetone) so that 0.16 g of optically active trans-2-[3-{4-(5-decylpyrimidine-2-yl) phenyl}propyl]-4-hexyl-4-butanolyde was obtained (yield 12% and melting point 57.9° C.).

EXAMPLE 16
Preparation of optically active cis-2-[3-{4-(5-decylpyrimidine-2-yl) phenyl}propyl]-4-hexyl-4-butanolyde (Example Compound No. 505)

0.69 g (2.66 mmol) optically active cis-2-(2-propenyl)-4-hexyl-4-butanolyde and 3 ml of THF were injected, and they were cooled to −17° C. Then, 6.4 ml of 9-borabicyclo [3.3.1]nonane (0.5M THF solution) was dripped, and stirring at 0° C. was performed for one hour. Then, stirring at room temperature was performed for one hour, and then 0.08 g (0.073 mmol) of tetrakis (triphenylphosphine) palladium, 1.18 g (2.66 mmol) of trifuoromethanesulfonic acid 4-(5-decylpyrimidine-2-yl) phenyl, 10 ml of DMF, and 0.74 g (5.32 mmol) of potassium carbonate were added, and stirring at 60° C. was performed for 5 hours. After reactions had been completed, water was added, and extraction with ethyl acetate was performed. The extracted solution was dried, and then the solvent was removed by filtration. Then, refining was performed with a silica gel column chromatography (developing solvent: hexane/ethyl acetate=20/1) and by recrystallization (acetone) so that 0.30 g of optically active cis-2-[3-{4-(5-decylpyrimidine-2-yl) phenyl}propyl]-4-hexyl-4-butanolyde was obtained (yield 22% and melting point 73.0° C.).

EXAMPLE 17
Preparation of optically active 2-[3-{2-(4-decylphenyl) pyrimidine-5-yl) phenyl}butyl]-4-hexyl-4-butanolyde (Example Compound No. 175)

1.09 g (3.99 mmol) of optically active 2-(3-butenyl)-4-hexyl-4-butanolyde and 3 ml of THF were injected, and they were cooled to −17° C. Then, 9.6 ml of 9-borabicyclo [3.3.1]nonane (0.5M THF solution) was dripped, and stirring at 0° C. was performed for one hour. Then, stirring at room temperature was performed for one hour, and then 0.13 g (0.073 mmol) of tetrakis (triphenylphosphine) palladium, 1.77 g (3.99 mmol) of trifuoromethanesulfonic acid 2-(4-decyphenyl)pyrimidine-5-yl, 10 ml of DMF, and 1.11 g (7.98 mmol) of potassium carbonate were added, and stirring at 60° C. was performed for 5 hours. After reactions had been completed, water was added, and extraction with ethyl acetate was performed. The extracted solution was dried, and then the solvent was removed by filtration. Then, refining was performed with a silica gel column chromatography (developing solvent: hexane/ethyl acetate=5/1) and by recrystallization (acetone) so that 0.42 g of optically active 2-[3-{2-(4-decylphenyl) pyrimidine-5-yl) phenyl}butyl]-4-hexyl-4-butanolyde was obtained (yield 20% and melting point 84.8° C.).

EXAMPLE 18
Preparation of 2-[2-{4-(5-decylpyrimidine-2-yl) phenyl}ethyl]-4-butyl-4-butanolyde (Example Compound No. 11)

0.43 g (0.89 mmol) of 2-[2-{4-(5-decylpyrimidine-2-yl) phenyl}ethyl]diethyl malonate, 0.11 g (0.98 mmol) of t-butoxypotassium and 4 ml of t-butanol were injected. Then, mixed solution of 0.11 g (1.07 mmol) of optically active (R)-1,2-epoxyhexane and 2 ml of t-butanol was dripped, and heating and stirring at 90° C. were performed for 6 hours. After the reactions had been completed, 6M hydrochloric acid was added to make pH to be 1, and extraction with ethyl acetate was performed. After the extracted solution had been dried, the solvent was removed by filtration. Then, refining was performed with a silica gel column chromatography (developing solvent: hexane/ethyl acetate 10/1) and by recrystallization (acetone) so that 0.05 g of 2-[2-{4-(5-decylpyrimidine-2-yl) phenyl}ethyl]-4-butyl-4-butanolyde was obtained (yield 12% and melting point 62° C.).

EXAMPLE 19
Preparation of 2-[2-{4-(5-decylpyrimidine-2-yl) phenyl}ethyl]-4-propyl-4-butanolyde (Example Compound No. 503)

0.92 g (1.91 mmol) of 2-[2-{4-(5-decylpyrimidine-2-yl) phenyl}ethyl]diethyl malonate, 0.26 g (2.10 mmol) of t-butoxypotassium and 5 ml of t-butanol were injected. Then, mixed solution of 0.22 g (2.29 mmol) of optically active (R)-1,2-epoxypentane and 2 ml of t-butanol was dripped, and heating and stirring at 90° C. were performed for 6 hours. After the reactions had been completed, 6M hydrochloric acid was added to make pH to be 1, and extraction with ethyl acetate was performed. After the extracted solution had been dried, the solvent was removed by filtration. Then, refining was performed with a silica gel column chromatography (developing solvent: hexane/ethyl acetate 10/1) and by recrystallization (acetone) so that 0.22 g of 2-[2-{4-(5-decylpyrimidine-2-yl) phenyl}ethyl]-4-propyl-4-butanolyde was obtained (yield 26% and melting point 54° C.).

EXAMPLE 20
Preparation of 2-[4-{4-(4-hexyl-4-butanolyde-2-yl) butyl}phenyl]-5-{4-(4-hexyl-4-butanolyde-2-yl) butyl}pyrimidine (Example Compound No. 502)

2.0 g (7.34 mmol) of optically active 2-(3-butenyl)-4-hexyl-4-butanlyde and 9 ml of THF were injected, and they were cooled to −17° C. Then, 17.7 ml of 9-borabicyclo [3.3.1]nonane (0.5M THF solution) was dripped, and stirring at 0° C. was performed for one hour. Furthermore, stirring at room temperature was performed for one hour, and then 0.16 g (0.073 mmol) of tetrakis (triphenylphosphine) palladium, 0.94 g (2.45 mmol) of trifluoromethane sulfonic acid 2-(4-bromophenyl) pyrimidine-5-yl, 10 ml of DMF and 1.35 g (9.8 mmol) of potassium carbonate were added. Then, they were stirred at 60° C. for 5 hours. After the reactions had been completed, water was added, and extraction with ethyl acetate was performed. After the extracted solution had been dried, the solvent was removed by filtration. Then, refining was performed with a silica gel column chromatography (developing solvent: hexane/ethyl acetate=5/1) and by recrystallization (once by hexane/ethyl acetate and once by toluene/methanol) so that 0.20 g of 2-[4-{4-(4-hexyl-4-butanolyde-2-yl) butyl}phenyl]-5-{4-(4-hexyl-4-butanolyde-2-yl) butyl}pyrimidine was obtained (yield 13%).

Phase Transition Temperature (°C.)

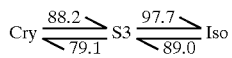

where S3 is undefined smectic phase

EXAMPLE 21
Preparation of optically active 2-vinyl-4-hexyl-4-butanolyde (Example Compound No. 509)

12.8 g (100 mmol) of naphthalene and 100 ml of dry THF were injected, and 1.4 g (200 mmol) of lithium was added at room temperature. Stirring was performed for 30 minutes, and then 14.6 g (200 mmol) of diethylamine was added at room temperature and they were stirred for 30 minutes. Then, mixed solution of 8.6 g (100 mmol) of vinyl acetate and 50 ml of dry THF was dripped at a temperature of −10° C. or lower. Stirring was performed at the foregoing temperature for 30 minutes, and then 12.8 g (100 mol) of (R)-1,2-epoxyoctane was dripped at a temperature of −10° C. or lower. Then, stirring at the foregoing temperature was performed for 30 minutes, and heat reflux was performed for 2 hours. After the reactions had been completed, cooling was performed, and they were immersed into ice water, and hydrochloric acid was added to be made acid. Extraction with diisopropyl ether was performed, and cleaning with water was performed. Then, anhydrous magnesium sulfate was added to be dried. After the solvent had been removed by filtration, 18.8 g of obtained carboxylic acid was added to 20 ml of diisopropyl ether. Then, stirring was performed at 40° C. for 9 hours. After the reactions had been completed, the solvent was removed by filtration. Then, refining was performed with a silica gel column chromatography (developing solvent: hexane/ethyl acetate=10/1) so that 2.75 g of optically active 2-vinyl-4-hexyl-4-butanolyde was obtained (yield 14%).

EXAMPLE 22
Preparation of optically active 4-(3-butenyl)-2-hexyl-4-butanolyde (Example Compound No. 522)

54.8 g (225 mmol) of 2-hexyl diethyl malonate, 25.2 g (225 mmol) of t-butoxypotassium and 500 ml of t-butanol were injected. Then, 20 g (204 mmol) of optically active (R)-1,2-epoxy-5-hexene was dripped, and heating and stirring at 90° C. were performed for 7 hours. After the reactions had been completed, 6M hydrochloric acid was added to make the pH to be 1, and extraction with ethyl acetate was performed. After the extracted solution had been dried, the solvent was removed by filtration. Then, refining was performed by distillation under reduced pressure and with a silica gel column chromatography (developing solvent: hexane/ethyl acetate 10/1) so that 24 g of optically active 4-(3-butenyl)-2-hexyl-4-butanolyde was obtained (yield 53%).

EXAMPLE 23
Preparation of optically active 4-[4-{4-(5-decylpyrimidine-2-yl) phenyl}butyl]-2-hexyl-4-butanolyde (Example Compound No. 506)

0.84 g (3.74 mmol) of 4-(3-butenyl)-2-hexyl-4-butanolyde and 2 ml of THF were injected, and they were cooled to −17° C. Then, 8.0 ml of 9-borabicyclo [3.3.1] nonane (0.5M THF solution) was dripped, and stirring was performed at 0° C. for one hour. Then, stirring was performed at room temperature for one hour, and 0.04 g of tetrakis (triphenylphosphine) palladium, 0.50 g (1.33 mmol) of 5-decyl-2-(4-bromophenyl) pyrimidine, 6 ml of DMF and 0.37 g of potassium carbonate were added, and they were stirred at 60° C. for 7 hours. After the reactions had been completed, water was added, and extraction with ethyl acetate was performed. After the extracted solution had been dried, the solvent was removed by filtration. Then, refining was performed with a silica gel column chromatography (developing solvent: hexane/ethyl acetate=5/1) and by recrystallization so that 0.20 g of optically active 4-[4-{4-(5-decylpyrimidine-2-yl) phenyl}butyl]-2-hexyl-4-butanolyde was obtained.

EXAMPLE 24
Preparation of optically active 4-[4-{4-(4-pentylcyclohexyl) phenyl}butyl]-2-hexyl-4-butanolyde (Example Compound No. 507)

0.84 g (3.74 mmol) of optically active 4-(3-butenyl)-2-hexyl-4-butanolyde and 2 ml of THF were injected, and they were cooled to −17° C. Then, 8 ml of 9-borabicyclo [3.3.1] nonane (0.5M THF solution) was dripped, and stirring was performed at 0° C. for one hour. Then, stirring at room temperature was performed for one hour, and then 0.04 g of tetrakis (triphenylphosphine) palladium, 0.42 g (1.36 mmol) of 4-(4-pentylcyclohexyl) phenylbromide, 6 ml of DMF and 0.37 g of potassium carbonate were added, and they were stirred at 60° C. for 7 hours. After the reactions had been completed, water was added and extraction with ethyl acetate was performed. After the extracted solution had been dried, the solvent was removed by filtration. Then, refining was performed with a silica gel column chromatography (developing solvent: hexane/ethyl acetate=5/1) and by recrystallization so that 0.20 g of optically active 4-[4-{4-(4-pentylcyclohexyl) phenyl}butyl]-2-hexyl-4-butanolyde was obtained (melting point 83.9° C.).

EXAMPLE 25
The following compounds containing Example Compound No. 5 prepared in Example 2 were mixed with the following parts by weight so that liquid crystal composition A was prepared.

| | |
|---|---|
| $C_6H_{13}$-Py2-Ph-O$C_{12}H_{25}$ | 4.2 |
| $C_8H_{17}$-Py2-Ph-O$C_9H_{19}$ | 8.4 |
| $C_8H_{17}$-Py2-Ph-O$C_{10}H_{21}$ | 8.4 |
| $C_9H_{19}$-Py2-Ph-O$C_6H_{17}$ | 4.2 |
| $C_{10}H_{21}$O-Ph-COO-Ph-OC$H_2$CH(C$H_3$)$C_2H_5$ | 27.5 |
| $C_6H_{13}$-Btb2-Ph-O$C_8H_{17}$ | 21.1 |
| $C_5H_{11}$-Ph-Td-Ph-$C_5H_{11}$ | 5.3 |
| $C_6H_{13}$-Ph-Td-Ph-$C_4H_9$ | 5.3 |
| $C_{11}H_{23}$-Py2-Ph-OCO-Tn-$C_4H_9$ | 5.3 |
| $C_{11}H_{23}$-Py2-Ph3F-OCO-Tn-$C_4H_9$ | 5.3 |
| $C_6H_{13}$*CHF(C$H_2$)$_2$O-Ph-Ph-(C$H_2$)$_2$-L1-$C_6H_{13}$ | 5.0 |

The phase transition temperature of the liquid crystal composition A is as follows:

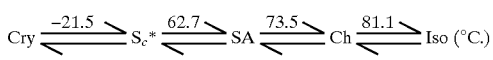

EXAMPLE 26
Two glass plates each having a thickness of 0.7 mm were prepared, and an ITO film was formed on the glass plate so that an electrode, to which voltage was applied, was formed. Then, SiO$_2$ was evaporated on the ITO film so that an insulating layer was formed. Then, isopropyl alcohol solution containing silane coupling material (KBM-602 manufactured by Shinetsu Kagaku) by 0.2% was applied for 15 seconds by a spinner rotating at a rotational speed of 2000 rpm so that surface treatment was performed. Then, heating and drying were performed at 120° C. for 20 minutes. Furthermore, the glass plates with the ITO films, further subjected to surface treatment, were, for 15 seconds, applied with dimethyl acetoamide solution containing polyimide resin precursor (SP-510 manufactured by Toray) by 1.5% by a spinner rotating at a rotational speed of 2000 rpm. After a desired film had been formed, heat shrinkage baking process was performed at 300° C. for 60 minutes. Thus, a film having a thickness of about 250 Å was applied.

The baked film was subjected to a rubbing process using acetate filling, and then it was cleaned with isopropyl alcohol solution. Then, silica beads having an average diameter of 2 μm were placed on one of the glass plates in such a manner that the axes of the rubbing processes run parallel to one another. Then, an adhesive sealant ("LiqussoBond" manufactured by Chisso) was used to bond the glass plates to each other. Then, the glass plates were heated to 100° C. for 60 minutes so that a cell was manufactured. Then, the liquid crystal composition B mixed in Example 10 was, in an isotropic fluid state, injected into the cell. Then, the cell was gradually cooled from the anisotropic phase to 25° C. at a rate of 20° C./hour so that a liquid crystal device (ferroelectric liquid crystal device) was manufactured. The thickness of the cell was measured by a Berek phase plate, resulting in about 2 μm. The thus-manufactured liquid crystal device was used to measure the intensity of the spontaneous polarization. The results are as follows:

|  | 10° C. | 30° C. | 40° C. |
|---|---|---|---|
| Spontaneous Polarization | 11.6 nc/cm² | 8.7 nc/cm² | 5.8 nc/cm² |

EXAMPLE 27

In the composition according to Example 25, Example Compound No. 47 manufactured in Example 3 was used in place of the Example Compound No. 5 so that liquid crystal composition B was prepared. The phase transition temperature of the liquid crystal composition B was as follows:

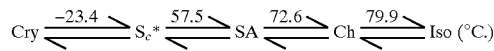

A ferroelectric liquid crystal liquid crystal device was manufactured by the same method as that of Example 26 except liquid crystal composition B being injected into the cell so that the spontaneous polarization was measured. The results are were as follows:

|  | 10° C. | 30° C. | 40° C. |
|---|---|---|---|
| Spontaneous Polarization | 7.8 nc/cm² | 5.5 nc/cm² | 4.5 nc/cm² |

EXAMPLE 28

Example Compound No. 19 manufactured in Example 4 was used in place of the Example Compound No. 5 according to Example 25 so that liquid crystal composition C was prepared. The phase transition temperature of the liquid crystal composition C was as follows:

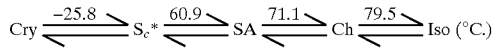

A ferroelectric liquid crystal liquid crystal device was manufactured by the same method as that of Example 11 except liquid crystal composition C being injected into the cell so that the spontaneous polarization was measured. The results are were as follows:

|  | 10° C. | 30° C. | 40° C. |
|---|---|---|---|
| Spontaneous Polarization | 15.2 nc/cm² | 12.2 nc/cm² | 10.1 nc/cm² |

EXAMPLE 29

Example Compound No. 257 manufactured in Example 6 was used in place of the Example Compound No. 5 according to Example 25 so that liquid crystal composition D was prepared. The phase transition temperature of the liquid crystal composition D was as follows:

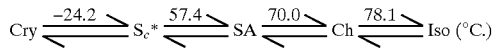

A ferroelectric liquid crystal liquid crystal device was manufactured by the same method as that of Example 11 except liquid crystal composition D being injected into the cell so that the spontaneous polarization was measured. The results are were as follows:

|  | 10° C. | 30° C. | 40° C. |
|---|---|---|---|
| Spontaneous Polarization | 9.0 nc/cm² | 7.1 nc/cm² | 5.0 nc/cm² |

EXAMPLE 30

Example Compound No. 229 manufactured in Example 8 was used in place of the Example Compound No. 5 according to Example 25 so that liquid crystal composition E was prepared. The phase transition temperature of the liquid crystal composition E was as follows:

A ferroelectric liquid crystal liquid crystal device was manufactured by the same method as that of Example 11 except liquid crystal composition E being injected into the cell so that the spontaneous polarization was measured. The results are were as follows:

|  | 10° C. | 30° C. | 40° C. |
|---|---|---|---|
| Spontaneous Polarization | 14.5 nc/cm² | 11.5 nc/cm² | 9.1 nc/cm² |

As can be understood from Examples 25 to 30, addition of the optically active compound according to the present invention to another liquid crystal compound in a small quantity will enable a liquid crystal composition having a large spontaneous polarization to be manufactured. Thus, it can be understood that the optically active compound according to the present invention has great performance for attaining the spontaneous polarization.

EXAMPLE 31

The following compounds were mixed with the following parts by weight so that liquid crystal composition F was prepared.

| Constitutional Formula | Parts by Weight |
|---|---|
| $C_9H_{19}$-Py2-Ph-$OC_9H_{19}$ | 6 |
| $C_{10}H_{21}$-Py2-Ph-$OC_8H_{17}$ | 6 |
| $C_8H_{17}$O-Pr1-Ph-O$(CH_2)_5$*CH$(CH_3)C_2H_5$ | 7 |
| $C_{11}H_{23}$O-Py2-Ph-O$(CH_2)_2$*CH$(CH_3)C_2H_5$ | 14 |
| $C_{10}H_{21}$-Pr2-Ph-$C_6H_{13}$ | 8 |
| $C_6H_{13}$-Py2-Ph-Ph-$C_4H_9$ | 4 |
| $C_8H_{17}$-Ph-Pr2-Ph-$OC_5H_{11}$ | 2 |
| $C_3H_7$-Cy-COO-Ph-Py1-$C_{12}H_{25}$ | 10 |
| $C_5H_{11}$-Cy-COO-Ph-Py1-$C_{12}H_{25}$ | 5 |
| $C_{10}H_{21}$O-Ph-COS-Ph-$OC_8H_{17}$ | 10 |
| $C_6H_{13}$-Ph-COO-Ph-Ph-OCH$_2$CH$(CH_3)C_2H_5$ | 7 |
| $C_3H_7$-Cy-$CH_2$O-Ph-Py1-$C_8H_{17}$ | 7 |
| $C_{10}H_{21}$-Ph-Ph-$OCH_2$-Ph-$C_7H_{15}$ | 5 |
| $C_{12}H_{25}$-Py2-Ph-$OCH_2$*CH(F)$C_5H_{11}$ | 2 |
| $C_5H_{11}$-Cy-COO-Ph-$OCH_2$*CH(F)$C_6H_{13}$ | 2 |
| $C_{12}H_{25}$O-Ph-Pa-COO$(CH_2)_3$*CH$(CH_3)C_2H_5$ | 2 |
| $C_{12}H_{25}$O-Ph-Pa-O$(CH_2)_3$*CH$(CH_3)OC_3H_7$ | 3 |

Furthermore, the following example compounds were mixed to the liquid crystal composition F with the following parts by weight so that liquid crystal composition G was prepared.

| Example Compound No. | Constitutional Formula | Parts by Weight |
|---|---|---|
| 15 | $C_{13}H_{27}$-Py2-Ph-$(CH_2)_2$-L1-$C_5H_{11}$ | 2 |
| 51 | $C_{12}H_{25}$-Btb2-Ph-$(CH_2)_2$-L1-$C_6H_{13}$ | 1 |
| 83 | $C_4H_9$-Ph-Tn-$(CH_2)_2$-L1-$C_7H_{15}$ | 2 |
| | F | 95 |

A liquid crystal device was manufactured by the same method as that of Example 11 except liquid crystal composition G being injected into the cell. A peak-to-peak voltage Vpp=20 V was applied to detect optical response (change in the transmitted light quantity 0 to 90%) under crossed-Nicol so that the response speed (hereinafter called "optical response speed") was measured. The results were as follows:

| | 10° C. | 25° C. | 40° C. |
|---|---|---|---|
| Response Speed | 391 μsec | 209 μsec | 113 μsec |

Comparative Example 1

A liquid crystal device was manufactured by the same method as that of Example 26 except liquid crystal composition F being injected into the cell. The optical response speed was measured by the same method as that of Example 16. The results were as follows:

| | 10° C. | 25° C. | 40° C. |
|---|---|---|---|
| Response Speed | 668 μsec | 340 μsec | 182 μsec |

EXAMPLE 32

The following example compounds were mixed with the following parts by weight in place of the example compounds mixed in the composition according to Example 31 so that liquid crystal composition H was prepared.

| Example Compound No. | Constitutional Formula | Parts by Weight |
|---|---|---|
| 22 | $C_7H_{15}$OCO-Cy-Ph-$(CH_2)_2$L1-$C_{14}H_{29}$ | 1 |
| 41 | $C_6H_{13}$-Gp1-Ph-$(CH_2)_2$-L1-$C_{12}H_{25}$ | 2 |
| 100 | $C_3H_7$-Ph-Ph-Pyl-$(CH_2)_2$-L1-$C_7H_{15}$ | 2 |
| | F | 95 |

A liquid crystal device was manufactured by the same method as that of Example 26 except liquid crystal composition H being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 413 μsec | 220 μsec | 121 μsec |

EXAMPLE 33

The following example compounds were mixed with the following parts by weight in place of the example compounds mixed in the composition according to Example 31 so that liquid crystal composition I was prepared.

| Example Compound No. | Constitutional Formula | Parts by Weight |
|---|---|---|
| 9 | $C_8H_{17}$O-Ph-COO-Ph-$(CH_2)_2$-L1-$C_6H_{13}$ | 1 |
| 60 | $C_6H_{13}$-Ph-Pr2-Ph-$(CH_2)_2$-L1-$C_6H_{13}$ | 2 |
| 84 | $C_8H_{17}$-Ph-Tz1-$(CH_2)_2$-L1-$C_{12}H_{25}$ | 2 |
| | F | 95 |

A liquid crystal device was manufactured by the same method as that of Example 26 except liquid crystal composition H being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 435 μsec | 230 μsec | 127 μsec |

EXAMPLE 34

The following example compounds were mixed with the following parts by weight in place of the example compounds mixed in the composition according to Example 31 so that liquid crystal composition J was prepared.

| Example Compound No. | Constitutional Formula | Parts by Weight |
|---|---|---|
| 115 | $C_8H_{17}$-Prl-Ph-$(CH_2)5$-L1-$C_8H_{17}$ | 2 |
| 134 | $C_5H_{11}$-Tz1-Ph-$(CH_2)_8$-L1-$C_8H_{17}$ | 2 |
| 160 | $C_6H_{13}$-Ph-Ph-Ph-$(CH_2)_6$-L1-$C_3H_7$ | 2 |
| | F | 95 |

A liquid crystal device was manufactured by the same method as that of Example 26 except liquid crystal composition J being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 451 μsec | 244 μsec | 135 μsec |

EXAMPLE 35

The following example compounds were mixed with the following parts by weight in place of the example compounds mixed in the composition according to Example 31 so that liquid crystal composition K was prepared.

| Example Compound No. | Constitutional Formula | Parts by Weight |
|---|---|---|
| 236 | $C_{10}H_{21}$-Pd-Ph-$(CH_2)_2$-L1-Ph-$OCH_3$ | 1 |
| 256 | $C_{11}H_{23}$-Id1-Ph-$(CH_2)_4$-L2-Ph-H | 2 |
| 299 | $C_{11}H_{23}$-Ph-Np-$(CH_2)_2$-L1-Ph-$C_6H_{13}$ | 2 |
| | F | 95 |

A liquid crystal device was manufactured by the same method as that of Example 26 except liquid crystal composition K being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 430 μsec | 231 μsec | 128 μsec |

EXAMPLE 36

The following example compounds were mixed with the following parts by weight so that liquid crystal composition L was prepared.

| Constitutional Formula | Parts by Weight |
|---|---|
| $C_7H_{15}$-Py2-Ph-$OC_9H_{19}$ | 12 |
| $C_{11}H_{23}$-Py2-Ph-$OC_6H_{13}$ | 10 |
| $C_8H_{17}$-Pr2-Ph-$O(CH_2)_5$*$CH(CH_3)C_2H_5$ | 10 |
| $C_{10}H_{21}$-Py2-Ph-$O(CH_2)_4CH(CH_3)OCH_3$ | 3 |
| $C_8H_{17}$-Py2-Ph-Ph-$OC_6H_{13}$ | 8 |
| $C_6H_{13}$O-Ph-OCO-Np-$OC_9H_{19}$ | 4 |
| $C_3H_7$-Cy-COO-Ph-$C_{11}H_{23}$ | 6 |
| $C_8H_{17}$-Cy-COO-Ph-Pyl-$C_{11}H_{23}$ | 2 |
| $C_5H_{11}$-Cy-COO-Ph-Pyl-$C_{11}H_{23}$ | 8 |
| $C_{10}H_{21}$O-Ph-COO-Ph-$OCH_2$*$CH(CH_3)C_2H_5$ | 15 |
| $C_4H_9$-$CH_2$O-Ph-Pyl-$C_6H_{13}$ | 7 |
| $C_5H_{11}$-Cy-$CH_2$O-Ph-Pyl-$C_6H_{13}$ | 7 |
| $C_9H_{19}$O-Ph-$OCH_2$-Ph-Ph-$C_7H_{15}$ | 4 |
| $C_6H_{13}$*$CH(CH_3)$O-Ph-COO-Ph-Ph-OCO*$CH(CH_3)OC_4H_9$ | 2 |
| $C_{12}H_{25}$-Py2-Ph-OCO*CH(Cl)*$CH(CH_3)C_2H_5$ | 2 |

Furthermore, the following example compounds were mixed to the liquid crystal composition L with the following parts by weight so that liquid crystal composition M was prepared.

| Example Compound No. | Constitutional Formula | Parts by Weight |
|---|---|---|
| 23 | $C_6H_{13}$-Cy-CH=CH-Ph-$(CH_2)_2$L1-$C_{10}H_{21}$ | 2 |
| 48 | $C_5H_{11}$-Id1-Ph2F-$(CH_2)_2$-L1-$C_6H_{13}$ | 2 |
| 88 | $C_8H_{17}OCH_2CH_2$-Ph-Np-$(CH_2)_2$-L1-$C_5H_{11}$ | 2 |
| | L | 94 |

A liquid crystal device was manufactured by the same method as that of Example 26 except liquid crystal composition M being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 451 μsec | 230 μsec | 129 μsec |

Comparative Example 2

A liquid crystal device was manufactured by the same method as that of Example 26 except liquid crystal composition L being injected into the cell. The optical response speed was measured by the same method as that of Example 31, and the switching state was observed. The results were as follows;

| | 10° C. | 25° C. | 40° C. |
|---|---|---|---|
| Response Speed | 784 μsec | 373 μsec | 197 μsec |

EXAMPLE 37

The following example compounds were mixed with the following parts by weight in place of the example compounds mixed in the composition according to Example 36 so that liquid crystal composition N was prepared.

| Example Compound No. | Constitutional Formula | Parts by Weight |
|---|---|---|
| 11 | $C_{10}H_{21}$-Pr2-Ph-$(CH_2)_2$-L1-$C_4H_9$ | 2 |
| 43 | $C_6H_{13}$-Cml-Ph-$(CH_2)_2$-L1-$C_8H_{17}$ | 2 |
| 92 | $C_6H_{13}$-Ph-Ep1-$(CH_2)_2$-L1-$C_6H_{13}$ | 2 |
| L | | 94 |

A liquid crystal device was manufactured by the same method as that of Example 26 except liquid crystal composition N being injected into the cell. The optical response speed was measured by the same method as that of Example 31, and the switching state was observed. The uniformity of orientation in the liquid crystal device was excellent such that monodomain state was obtained. The results were as follows;

|  | 10° C. | 25° C. | 40° C. |
|---|---|---|---|
| Response Speed | 431 μsec | 215 μsec | 119 μsec |

EXAMPLE 38

The following example compounds were mixed with the following parts by weight in place of the example compounds mixed in the composition according to Example 36 so that liquid crystal composition O was prepared.

| Example Compound No. | Constitutional Formula | Parts by Weight |
|---|---|---|
| 31 | $C_9H_{19}$O-Tz2-Ph-$(CH_2)_2$-L1-$C_5H_{11}$ | 2 |
| 58 | $C_3H_7$-Py2-Ph-Ph-$(CH_2)_2$-L1-$C_8H_{17}$ | 2 |
| 78 | $C_4H_9$-Ph-$CH_2$O-Cy-$(CH_2)_2$-L1-$C_7H_{15}$ | 1 |
| L | | 95 |

A liquid crystal device was manufactured by the same method as that of Example 26 except liquid crystal composition O being injected into the cell. The optical response speed was measured by the same method as that of Example 31, and the switching state was observed. The uniformity of orientation in the liquid crystal device was excellent such that monodomain state was obtained. The results were as follows;

|  | 10° C. | 25° C. | 40° C. |
|---|---|---|---|
| Response Speed | 510 μsec | 263 μsec | 150 μsec |

EXAMPLE 39

The following example compounds were mixed with the following parts by weight in place of the example compounds mixed in the composition according to Example 36 so that liquid crystal composition P was prepared.

| Example Compound No. | Constitutional Formula | Parts by Weight |
|---|---|---|
| 331 | $C_6H_{13}$O-Py2-Ph-$(CH_2)_4$-L2-$C_8H_{17}$ | 2 |
| 374 | $C_5H_{11}$-Ha2-Ph-$(CH_2)_5$-L2-$C_{11}H_{23}$ | 2 |
| 407 | $C_6H_{13}$-Ph-Ep1-$(CH_2)_4$-L2-$C_6H_{13}$ | 2 |
| L | | 94 |

A liquid crystal device was manufactured by the same method as that of Example 26 except liquid crystal composition P being injected into the cell. The optical response speed was measured by the same method as that of Example 31, and the switching state was observed. The uniformity of orientation in the liquid crystal device was excellent such that monodomain state was obtained. The results were as follows;

|  | 10° C. | 25° C. | 40° C. |
|---|---|---|---|
| Response Speed | 486 μsec | 253 μsec | 145 μsec |

EXAMPLE 40

The following example compounds were mixed with the following parts by weight in place of the example compounds mixed in the composition according to Example 36 so that liquid crystal composition Q was prepared.

| Example Compound No. | Constitutional Formula | Parts by Weight |
|---|---|---|
| 310 | $C_{10}H_{21}$-Py2-Ph-$(CH_2)_2$-LM1-$C_7H_{15}$ | 1 |
| 456 | $C_6F_{13}CH_2$O-Py2-Ph-$(CH_2)_2$-L1-$C_6H_{13}$ | 2 |
| 483 | $C_{10}H_{21}$O-Py2-Ph-$(CH_2)_2$-L1-$C_6H_{13}$ | 2 |
| L | | 95 |

A liquid crystal device was manufactured by the same method as that of Example 26 except liquid crystal composition Q being injected into the cell. The optical response speed was measured by the same method as that of Example 31, and the switching state was observed. The uniformity of orientation in the liquid crystal device was excellent such that monodomain state was obtained. The results were as follows;

|  | 10° C. | 25° C. | 40° C. |
|---|---|---|---|
| Response Speed | 440 μsec | 224 μsec | 128 μsec |

EXAMPLE 41

The following compounds were mixed with the following parts by weight so that liquid crystal composition R was prepared.

| Constitutinoal Formula | Parts by Weight |
|---|---|
| $C_8H_{17}$-Py2-Ph-$OC_6H_{13}$ | 10 |
| $C_8H_{17}$-Py2-Ph-$OC_9H_{19}$ | 5 |
| $C_{10}H_{21}$-Py2-Ph-$OCOC_8H_{17}$ | 7 |
| $C_{10}H_{21}$-Py2-Ph-O$(CH_2)_3$CH$(CH_3)OC_3H_7$ | 7 |

-continued

| Constitutinoal Formula | Parts by Weight |
|---|---|
| $C_{12}H_{25}$-Py2-Ph-O$(CH_2)_4$CH$(CH_3)$OCH$_3$ | 6 |
| $C_5H_{11}$-Py2-Ph-Ph-$C_6H_{15}$ | 5 |
| $C_7H_{15}$-Py2-Ph-Ph-$C_6H_{13}$ | 5 |
| $C_4H_9$-Cy-COO-Ph-Py1-$C_{12}H_{25}$ | 8 |
| $C_3H_7$-Cy-COO-Ph-Py1-$C_{10}H_{21}$ | 8 |
| $C_9H_{19}$O-Ph-COO-Ph-O$C_5H_{11}$ | 20 |
| $C_8H_{17}$-Ph-COO-Ph-Ph-OCH$_2$CH$(CH_3)C_2H_5$ | 5 |
| $C_8H_{17}$-Ph-OCO-Ph-Ph-*CH$(CH_3)$OCO$C_6H_{13}$ | 5 |
| $C_6H_{13}$-Ph-OCH$_2$-Ph-Ph-$C_7H_{15}$ | 6 |
| $C_{12}H_{25}$-Py2-Ph-OCH$_2$*CH(F)$C_6H_{13}$ | 3 |

The following example compounds were mixed with the following parts by weight to the foregoing liquid crystal composition R so that liquid crystal composition S was prepared.

| Example Compound No. | Constitutional Formula | Parts by Weight |
|---|---|---|
| 1 | $C_6H_{13}$-Ph-$(CH_2)_2$-L1-$C_8H_{17}$ | 2 |
| 25 | $C_5H_{11}$-Pa-Ph-$(CH_2)_2$-L1-$C_8H_{17}$ | 2 |
| 34 | $C_6H_{13}$-Boa2-Ph-$(CH_2)_2$-L1-$C_{10}H_{21}$ | 2 |
| L | | 94 |

A liquid crystal device was manufactured by the same method as that of Example 26 except liquid crystal composition S being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 372 μsec | 195 μsec | 106 μsec |

Comparative Example 3

A liquid crystal device was manufactured by the same method as that according to Example 26 except liquid crystal composition R mixed in the composition according to Example 24 being injected into the cell. The optical response speed was measured by the same method as that according to Example 31. The results were as follows.

| | 10° C. | 25° C. | 40° C. |
|---|---|---|---|
| Response Speed | 653 μsec | 317 μsec | 159 μsec |

EXAMPLE 42

The following example compounds were mixed with the following parts by weight in place of the example compounds mixed in the composition according to Example 41 so that liquid crystal composition T was prepared.

| Example Compound No. | Constitutional Formula | Parts by Weight |
|---|---|---|
| 26 | $C_{10}H_{21}$-Pd-Ph-$(CH_2)_2$-L1-$C_6H_{13}$ | 2 |
| 37 | $C_6H_{13}$-Btb2-Ph-$(CH_2)_2$-L1-$C_{14}H_{29}$ | 2 |
| 53 | $CH_2$=CH$(CH_2)_3$O-Ep2-Ph-$(CH_2)_2$-L1-$C_6H_{13}$ | 1 |
| R | | 95 |

A liquid crystal device was manufactured by the same method as that of Example 26 except liquid crystal composition T being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 411 μsec | 217 μsec | 118 μsec |

EXAMPLE 43

The following example compounds were mixed with the following parts by weight in place of the example compounds mixed in the composition according to Example 41 so that liquid crystal composition U was prepared.

| Example Compound No. | Constitutional Formula | Parts by Weight |
|---|---|---|
| 18 | $C_5H_{11}$-Py2-Ph23F-$(CH_2)_2$-L1-$C_4H_9$ | 2 |
| 72 | $C_6H_{13}$-Ph-Py1-$(CH_2)_2$-L1-$C_6H_{13}$ | 2 |
| 93 | $C_9H_{19}$O-Gp1-$(CH_2)_2$-L1-$C_8H_{17}$ | 2 |
| R | | 94 |

A liquid crystal device was manufactured by the same method as that of Example 26 except liquid crystal composition U being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 366 μsec | 191 μsec | 104 μsec |

EXAMPLE 44

The following example compounds were mixed with the following parts by weight in place of the example compounds mixed in the composition according to Example 41 so that liquid crystal composition V was prepared.

| Example Compound No. | Constitutional Formula | Parts by Weight |
|---|---|---|
| 153 | $C_6H_{13}$-Tn-Ph-$(CH_2)_4$-L1-$C_7H_{15}$ | 2 |
| 170 | H-Hb2-Ph-$(CH_2)_8$-L1-$C_8H_{17}$ | 1 |
| 194 | $C_5H_{11}$-Epl-$(CH_2)_8$-L1-$C_4H_9$ | 2 |
| | R | 95 |

A liquid crystal device was manufactured by the same method as that of Example 26 except liquid crystal composition V being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 450 μsec | 237 μsec | 130 μsec |

EXAMPLE 45

The following example compounds were mixed with the following parts by weight in place of the example compounds mixed in the composition according to Example 40 so that liquid crystal composition W was prepared.

| Example Compound No. | Constitutional Formula | Parts by Weight |
|---|---|---|
| 230 | $C_8H_{17}$-Py2-Ph3F-$(CH_2)_2$-L1-Ph-$C_6H_{13}$ | 2 |
| 336 | $C_6H_{13}$-Cy-Ph-$(CH_2)_8$-L2-$C_3H_6OC_4H_9$ | 2 |
| 379 | $C_7H_{15}$-Ph-Py2-Ph-$(CH_2)_6$-L2-$C_{10}H_{21}$ | 2 |
| | R | 94 |

A liquid crystal device was manufactured by the same method as that of Example 26 except liquid crystal composition W being injected into the cell. The optical response speed was measured by the same method as that of Example 31, and the switching state was observed. The uniformity of orientation in the liquid crystal device was excellent such that monodomain state was obtained. The results were as follows;

| | 10° C. | 25° C. | 40° C. |
|---|---|---|---|
| Response Speed | 400 μsec | 212 μsec | 116 μsec |

As can be understood from Examples 31 to 45, the liquid crystal devices having the liquid crystal compositions G to K, M to Q and S to W according to the present invention between substrates thereof are able to improve the operation characteristic and high speed response at low temperatures. Also the temperature dependency of the optical response speed can be reduced.

EXAMPLE 46

A liquid crystal device was manufactured by the same method as that of Example 26 except that 2% water solution of polyvinyl alcohol resin (PUA-117 manufactured by Kurare) in place of dimethylacetoamide solution containing polyimide resin precursor by 1.5% according to Example 26. The optical response speed was measured by the same method as that according to Example 31. The results were as follows:

| | 10° C. | 25° C. | 40° C. |
|---|---|---|---|
| Response Speed | 378 μsec | 202 μsec | 109 μsec |

EXAMPLE 47

A liquid crystal device was manufactured by the same method as that of Example 26 except that the orientation control layer was formed only by polyimide resin in such a manner that SiO2 according to Example 26 was not used. The optical response speed was measured by the same method as that according to Example 31. The results were as follows:

| | 10° C. | 25° C. | 40° C. |
|---|---|---|---|
| Response Speed | 350 μsec | 188 μsec | 101 μsec |

As can be understood from Examples 46 and 47, the liquid crystal devices respectively having the liquid crystal compositions according to the present invention are able to improve the operation characteristic and the temperature dependency of the optical response speed can be reduced even if the structure of the device, such as the orientation control film, is changed.

EXAMPLE 48

The following compounds were mixed with the following parts by weight so that liquid crystal composition X was prepared.

| | |
|---|---|
| $C_6H_{13}$-Py2-Ph-O $(CH_2)_4C_3F_7$ | 5 |
| $C_{11}H_{23}$-Py2-Ph-$OCH_2C_4F_9$ | 10 |
| $C_8H_{17}$O-Pr1-Ph-O $(CH_2)_5CH$ $(CH_3)$ $C_2H_5$ | 5 |
| $C_{10}H_{21}$-Py2-Ph-O $(CH_2)_4CH$ $(CH_3)$ $OCH_3$ | 10 |
| $C_6H_{13}$-Py2-Ph-Ph-$C_8H_{17}$ | 7 |
| $C_8H_{17}$-Py2-Ph-$OC_6H_{13}$ | 15 |
| $C_8H_{11}$-Cy-COO-Ph-Py1-$C_{12}H_{25}$ | 5 |
| $C_4H_9$-Cy-COO-Ph-Py1-$C_{11}H_{23}$ | 5 |
| $C_3H_7$-Cy-COO-Ph-Py1-$C_{11}H_{23}$ | 5 |
| $C_{12}H_{25}$O-Ph-Pa-CO $(CH_2)_3$*CH $(CH_3)$ $C_2H_5$ | 2 |
| $C_{10}H_{21}$-Py2-Ph-$OCH_2$*CH (F) $C_2H_5$ | 5 |
| $C_6H_{13}$-Cy-COO-Ph-$OCH_2$*CH (F) $C_6H_{13}$ | 2 |
| $C_8H_{17}$-Ph-OCO-Ph-Ph-CH $(CH_3)$ $OCOC_6H_{13}$ | 6 |
| $C_8H_{17}$-Py2-Ph-OCO-Ph-F | 2 |
| $C_7H_{15}$O-Ph-Tz1-Ph-$C_5H_{11}$ | 3 |
| $C_6H_{13}$O-Btb2-Ph-OCO $(CH_2)_6C_2F_5$ | 3 |
| $C_8H_{17}$O-Ph-COS-Ph-$OCH_2C_3F_7$ | 10 |

Furthermore, the following example compounds were mixed with the foregoing liquid crystal composition X with the following parts by weight so that liquid crystal composition XA was prepared.

| Example Compound No. | Constitutional Formula | Parts by Weight |
|---|---|---|
| 27 | $C_6H_{13}$-Dt2-Ph-$(CH_2)_2$-L1-$(CH_2)_7$CH=$CH_2$ | 1 |
| 33 | $C_{10}H_{21}$-Dx2-Ph-$(CH_2)_2$-L1-$C_7H_{15}$ | 1 |
| 104 | $C_7H_{15}$-Tn-Ph-Py1-$(CH_2)_2$L1-$C_8H_{17}$ | 1 |
| | X | 97 |

Then, the foregoing liquid crystal compositions were used in the following procedure to manufacture cells, the optical response of which was observed.

Two glass plates each having a thickness of 0.7 mm were prepared, and an ITO film was formed on the glass plate so that an electrode, to which voltage was applied, was formed. Then, $SiO_2$ was evaporated on the ITO film so that an insulating layer was formed. Then, isopropyl alcohol solution containing silane coupling material (KBM-602 manufactured by Shinetsu Kagaku) by 0.2% was applied for 15 seconds by a spinner rotating at a rotational speed of 2000 rpm so that surface treatment was performed. Then, heating and drying were performed at 120° C. for 20 minutes. Furthermore, the glass plates with the ITO films, further subjected to surface treatment, were, for 15 seconds, applied with dimethyl acetoamide solution containing polyimide resin precursor (SP-510 manufactured by Toray) by 1.0% by a spinner rotating at a rotational speed of 3000 rpm. After a desired film had been formed, heat shrinkage baking process was performed at 300° C. for 60 minutes. Thus, a film having a thickness of about 120 Å was applied.

The baked film was subjected to a rubbing process using acetate filling, and then it was cleaned with isopropyl alcohol solution. Then, silica beads having an average diameter of 1.5 µm were placed on one of the glass plates in such a manner that the axes of the rubbing processes run parallel to one another. Then, an adhesive sealant ("LiqussoBond" manufactured by Chisso) was used to bond the glass plates to each other. Then, the glass plates were heated to 100° C. for 60 minutes so that a cell was manufactured. The thickness of the cell was measured by a Berek phase plate, resulting in about 1.5 µm. Then, the liquid crystal composition XA was, in an isotropic fluid state, injected into the cell. Then, the cell was gradually cooled from the anisotropic phase to 25° C. at a rate of 20° C./hour so that a liquid crystal device (ferroelectric liquid crystal device) was manufactured. The liquid crystal device was used to measure the contrast at 30° C. with the operating waveform (⅓ bias ratio) shown in FIG. 5, resulting in 15.1.

Comparative Example 4

A liquid crystal device was manufactured by the same method as that of Example 33 except liquid crystal composition X mixed in Example 33 being injected into the cell. By using similar operation waveforms, the contrast at the time of the operation at 30° C. was measured. The resulted contrast was 8.1.

EXAMPLE 49

The following example compounds were mixed with the foregoing with the following parts by weight in place of the example compounds of the compositions according to Example 48 so that liquid crystal composition XB was prepared.

| Example Compound No. | Constitutional Formula | Parts by Weight |
|---|---|---|
| 21 | $C_6H_{13}$-Cy-Ph-$(CH_2)_2$-L1-$C_4H_8OC_4H_9$ | 1 |
| 36 | $C_{16}H_{33}$O-Bta2-Ph-$(CH_2)_2$-L1-$C_6H_{13}$ | 2 |
| 65 | $C_4H_9$-Ph3TF-Pa-Ph-$(CH_2)_2$-L1-$(CH_2)_3CH(CH_3)_2$ | 2 |
| | X | 95 |

A liquid crystal device was manufactured by the same method as that of Example 48 except the foregoing composition being used. By using similar operation waveforms to those in Example 48, the contrast at the time of the operation at 30° C. was measured. The resulted contrast was 17.3.

EXAMPLE 50

The following example compounds were mixed with the foregoing with the following parts by weight in place of the example compounds of the compositions according to Example 48 so that liquid crystal composition XC was prepared.

| Example Compound No. | Constitutional Formula | Parts by Weight |
|---|---|---|
| 44 | $C_8H_{17}$-1o1-Ph-$(CH_2)_2$-L1-$C_6H_{13}$ | 1 |
| 86 | $C_6H_{13}$-Ph2F-Td-$(CH_2)_2$-L1-$(CH_2)_3CH(CH_3)C_6H_{13}$ | 2 |
| 102 | $C_5H_{11}$-Ph-Ph3F-Tz1-$(CH_2)_2$-L1-$C_3H_7$ | 2 |
| | X | 95 |

A liquid crystal device was manufactured by the same method as that of Example 48 except the foregoing composition being used. By using similar operation waveforms to those in Example 48, the contrast at the time of the operation at 30° C. was measured. The resulted contrast was 17.7.

EXAMPLE 51

The following example compounds were mixed with the foregoing with the following parts by weight in place of the example compounds of the compositions according to Example 48 so that liquid crystal composition XD was prepared.

| Example Compound No. | Constitutional Formula | Parts by Weight |
|---|---|---|
| 6 | $C_7H_{15}$O-Ph-Ph23F-$(CH_2)_2$-L1-$C_6H_{13}$ | 1 |
| 59 | $C_5H_{11}$-Ha2-Ph-$(CH_2)_2$-L1-$C_{11}H_{23}$ | 2 |
| 95 | $C_3H_7$COO-Ph-Gp1-$(CH_2)_2$-L1-$C_{11}H_{23}$ | 2 |
| | X | 95 |

A liquid crystal device was manufactured by the same method as that of Example 48 except the foregoing composition being used. By using similar operation waveforms to those in Example 48, the contrast at the time of the operation at 30° C. was measured The resulted contrast was 21.2.

EXAMPLE 52

The following example compounds were mixed with the foregoing with the following parts by weight in place of the example compounds of the compositions according to Example 48 so that liquid crystal composition XE was prepared.

| Example Compound No. | Constitutional Formula | Parts by Weight |
|---|---|---|
| 126 | $C_8H_{17}$-Py2-Ph-$(CH_2)_4$-L1-$CH_2OC_6H_{13}$ | 2 |
| 147 | $C_6H_{13}$-Cm1-Ph-$(CH_2)_4$-L1-$C_8H_{17}$ | 1 |
| 186 | $C_3H_7$-Ph2C1-Tn-$(CH_2)_{13}$-L1-$C_{10}H_{21}$ | 1 |
| X | | 96 |

A liquid crystal device was manufactured by the same method as that of Example 48 except the foregoing composition being used. By using similar operation waveforms to those in Example 48, the contrast at the time of the operation at 30° C. was measured. The resulted contrast was 19.0.

EXAMPLE 53

The following example compounds were mixed with the foregoing with the following parts by weight in place of the example compounds of the compositions according to Example 48 so that liquid crystal composition XF was prepared.

| Example Compound No. | Constitutional Formula | Parts by Weight |
|---|---|---|
| 226 | $C_6H_{13}O$-Py2-Ph-$(CH_2)_6$-L2-Ph-$C_6H_{13}$ | 2 |
| 261 | $C_{12}H_{25}$-Btb2-Ph-$(CH_2)_9$-L1-Ph-H | 2 |
| 294 | $C_8H_{17}$-Ph-Tz1-$(CH_2)_2$-L1-Ph-H | 1 |
| X | | 95 |

A liquid crystal device was manufactured by the same method as that of Example 33 except the foregoing composition being used. By using similar operation waveforms to those in Example 48, the contrast at the time of the operation at 30° C. was measured. The resulted contrast was 18.2.

EXAMPLE 54

The following example compounds were mixed with the foregoing with the following parts by weight in place of the example compounds of the compositions according to Example 48 so that liquid crystal composition XG was prepared.

| Example Compound No. | Constitutional Formula | Parts by Weight |
|---|---|---|
| 326 | $C_{10}H_{21}$-Pr2-Ph-$(CH_2)_6$-L2-$C_4H_9$ | 2 |
| 460 | $C_{10}F_{21}CH_2O$-Py2-Ph-$(CH_2)_2$-L1.-$C_6H_{13}$ | 2 |
| 464 | $C_6F_{13}CH_2O$-Ph-Ph-$(CH_2)_8$-L2-$C_6H_{13}$ | 1 |
| X | | 95 |

A liquid crystal device was manufactured by the same method as that of Example 48 except the foregoing composition being used. By using similar operation waveforms to those in Example 48, the contrast at the time of the operation at 30° C. was measured. The resulted contrast was 23.1.

As can be understood from Examples 48 to 54, the liquid crystal device including any of the liquid crystal compositions XA, XB, XC, XD, XE, XF and XG had intense contrast at the time of the operation.

EXAMPLE 55

The following example compounds were mixed with the foregoing with the following parts by weight in place of the example compounds of the compositions according to Example 48 so that liquid crystal composition XH was prepared.

| Example Compound No. | Constitutional Formula | Parts by Weight |
|---|---|---|
| 19 | $C_{10}H_{21}$-Py2-Ph-$(CH_1)_2$-L1-$C_6H_{13}$ | 5 |
| X | | 95 |

A liquid crystal device was manufactured by the same method as that of Example 48 except the foregoing composition being used. By using similar operation waveforms to those in Example 48, the contrast at the time of the operation at 30° C. was measured. The resulted contrast was 16.3.

Comparative Example 5

Compounds which had been disclosed in U.S. Pat. No. 4,973,425 and in which a lactone ring and a mesogen skeleton were bonded with each by a methyleneoxy group was prepared by a method disclosed in the same. The melting points of compounds A and B are as follows:

| | | melting point |
|---|---|---|
| Comparative Compound A | cis-$C_{10}H_{21}$-Py2-Ph-$OCH_2$-L2-$C_6H_{13}$ | 137.3° C. |
| Comparative Compound B | trans-$C_{10}H_{21}$-Py2-Ph-$OCH_2$-L2-$C_6H_{13}$ | 97.1° C. |

Then, compound A was mixed with the following parts by weight in place of the example compound of the composition according to Example 48 so that liquid crystal composition XI as prepared.

| Constitutional Formula | Parts by Weight |
|---|---|
| cis-$C_{10}H_{21}$-Py2-Ph-$OCH_2$-L2-$C_6H_{13}$ | 5 |
| X | 95 |

A liquid crystal device was manufactured by the same method as that of Example 48 except the foregoing composition being used. By using similar operation waveforms to those in Example 48, the contrast at the time of the operation at 30° C. was measured. The resulted contrast was 10.4.

Compound B was mixed with the following parts by weight in place of the example compound of the composition according to Example 48 so that liquid crystal composition XJ was prepared.

| Constitutional Formula | Parts by Weight |
|---|---|
| trans-$C_{10}H_{21}$-Py2-Ph-$OCH_2$-L2-$C_6H_{13}$ | 5 |
| X | 95 |

A ferroelectric liquid crystal device was manufactured by the same method as that of Example 48 except the foregoing composition being used. By using similar operation waveforms to those in Example 48, the contrast at the time of the operation at 30° C. was measured. The resulted contrast was 9.2.

As can be understood from Example 55 and Comparative Example 5, the liquid crystal device containing liquid crystal composition H according to the present invention exhibited greatly intense contrast at the time of the operation as compared with the liquid crystal device containing liquid crystal composition XI and XJ including compound A or B.

EXAMPLE 56

A liquid crystal device was manufactured by the same method as that of Example 48 except 2% water solution of polyvinyl alcohol resin (PVA-117 manufactured by Kurare) being used in place of dimethylacetoamide solution of polyimide resin precursor by 1.0% according to Example 48. By employing a similar method to that in Example 48, the contrast at the time of the operation at 30° C. was measured. The resulted contrast was 16.1.

EXAMPLE 57

A liquid crystal device was manufactured by the same method as that of Example 48 except the orientation control layer being formed by only polyimide resin without SiO2 employed in Example 48. By employing a similar method to that in Example 48, the contrast at the time of the operation at 30° C. was measured. The resulted contrast was 14.5.

EXAMPLE 58

A ferroelectric liquid crystal device was manufactured by the same method as that of Example 48 except 1% NMP solution of polyamide acid (LQ1802 manufactured by Hitachi Kasei) being baked at 270° C. for one hour in place of dimethyl acetoamide solution of polyimide precursor by 1.0% employed in Example 48. By employing a similar method to that in Example 48, the contrast at the time of the operation at 30° C. was measured. The resulted contrast was 28.1.

As can be understood from Examples 56, 57 and 58, even if the structure of the device is changed, the liquid crystal device according to the present invention having the liquid crystal composition disposed between substrates enables intense contrast similar to the device according to Example 48. Even if the operation waveform is changed, the detailed investigation resulted in that the liquid crystal device having the liquid crystal composition (ferroelectric liquid crystal composition) according to the present invention enables intense contrast to be obtained.

As described above, according to the present invention, there is provided a novel optically active compound exhibiting excellent performance of realizing spontaneous polarization. In particular, the liquid crystal composition containing the optically active compound according to the present invention can be operated by making using of the ferroelectric characteristic of the liquid crystal composition. As described above, the liquid crystal device according to the present invention using the characteristic of the liquid crystal composition has excellent switching characteristic, high-speed response, capability of reducing in dependency of the optical response speed upon the temperature, and intense contrast. A display apparatus comprising the liquid crystal device according to the present invention with a light source, an operating circuit and the like as a display device is an excellent apparatus.

Although the invention has been described in its preferred form with a certain degree of particularity, it is understood that the present disclosure of the preferred form can be changed in the details of construction and the combination and arrangement of parts may be resorted to without departing from the spirit and the scope of the invention as hereinafter claimed.

What is claimed is:

1. An optically active compound represented by the following general formula (I):

$$R_1-A_1-A_2-X_1-A_3-(CH_2)_p-L-A_4-R_2 \qquad (I)$$

where $R_1$ is F, CN or straight chain, branched alkyl group (one or more —$CH_2$— in the alkyl group may be replaced by —O—, —S—, —CO—, —CH(CN)—, —CH=CH— or —C≡C— under condition that heteroatoms do not position adjacently and one or more hydrogen atom in the alkyl group may be replaced by fluorine atom) having 1 to 30 carbon atoms or cyclic alkyl group wherein the cyclic alkyl is a 3–6 membered heterocyclic ring having 1 or 2 oxygen heteroatoms, wherein 1 or 2 nonadjacent —$CH_2$— moieties is optionally replaced with —CO—, said heterocyclic ring being optionally substituted by at least one alkyl group and $R_2$ is H, F, CN or straight chain or branched alkyl group (one or more —$CH_2$— in the alkyl group may be replaced by —O—, —S—, —CO—, —CH(CN)—, —CH=CH— or —C≡C— under condition that heteroatoms do not position adjacently and one or more hydrogen atom in the alkyl group may be replaced by fluorine atom) having 1 to 30 carbon atoms; $A_3$ is a group selected from the group consisting of 1,4-phenylene, pyridine-2,5-diyl, pyrimidine-2,5-diyl, pyrazine-2,5-diyl, pyridazine-3,6-diyl, 1,4-cyclohexylene, 1,3-dioxane-2,5-diyl, 1,3-ditiane-2,5-diyl, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2,6-diyl, quinoxaline-2,6-diyl, quinoline-2,6-diyl, 2,6-naphthylene, indane-2,5-diyl, 2-alkylindane-2,5-diyl (the alkyl group is a straight chain or branched alkyl group having 1 to 18 carbon atoms), indanone-2,6-diyl, 2-alkylindane-2,6-diyl (the alkyl group is a straight chain or branched alkyl group having 1 to 18 carbon atoms), coumarane-2,5-diyl and 2-alkylcoumarane-2,5-diyl (the alkyl group is a straight chain or branched alkyl group having 1 to 18 carbon atoms), each of which may be substituted by at least one substituent selected from the group consisting of F, Cl, Br, $CH_3$, and CN; $A_1$, $A_2$ and $A_4$ are independently single bonds or $A_3$; $X_1^+$ is a single bond, —COO—, —OCO—, —$CH_2$O—, —O$CH_2$—, —$CH_2CH_2$—, —CH=CH— or —C≡C—; p is an integer from 2 to 20; L is optically active butanolyde-2,4-diyl or optically active 4-alkylbutanolyde-2,4-diyl (the alkyl group is straight-chain or branched alkyl group having 1 to 5 carbon atoms) or optically active 2-alkylbutanolyde-2,4-diyl (the alkyl group is straight-chain or branched alkyl group having 1 to 5 carbon atoms).

2. An optically active compound according to claim 1, wherein said optically active compound represented by general formula (I) is any of compounds in (Ia) to (Id):

(Ia) an optically active compound in which $A_1$ and $A_2$ respectively are single bonds or groups selected from the group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, $CH_3$, $CF_3$ and CN, $A_3$ is 1,4-phenylene, which may be substituted by at least one substituent selected from the group consisting of F, Cl, Br, $CH_3$, $CF_3$ and CN and $A_4$ is a single bond;

(Ib) an optically active compound in which A₁ and A₂ are single bonds or 1,4-phenylene, which may be substituted by at least one substituent selected from the group consisting of F, Cl, Br, CH₃, CF₃ and CN, A₃ is a group selected from the group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl and A₄ is a single bond;

(Ic) an optically active compound in which A₁ is a single bond, A₂ and A₄ are respectively groups selected from the following group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, CH₃, CF₃ and CN, and A₃ is 1,4-phenylene, which may be substituted by at least one substituent selected from the group consisting of F, Cl, Br, CH₃, CF₃ and CN; and (Id) an optically active compound in which A₁ is a single bond, A₂ is a single bond or 1,4-phenylene, which may be substituted by at least one substituent selected from the group consisting of F, Cl, Br, CH₃, CF₃ and CN, A₃ is a group selected from the group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl and A₄ is 1,4-phenylene, which may be substituted by at least one substituent selected from the group consisting of F, Cl, Br, CH₃, CF₃ and CN.

3. An optically active compound according to claim 1, wherein said optically active compound represented by general formula (I) is any of compounds in (Iaa) to (Idb):

(Iaa) an optically active compound in which A₁, A₂, A₄ and X₁ are single bonds, and A₃ is 1,4-phenylene, which may be substituted by at least one substituent selected from the group consisting of F, Cl, Br, CH₃, CF₃ and CN;

(Iab) an optically active compound in which A₁, A₄ and X₁ are single bonds, A₂ is a group selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, each of which may be substituted by at least one substituent selected from the group consisting of F, Cl, Br, CH₃, CF₃ and CN, and A₃ is 1,4-phenylene or that having one or two substituents, which may be substituted by at least one substituent selected from the group consisting of F, Cl, Br, CH₃, CF₃ and CN;

(Iac) an optically active compound in which A₄ and X₁ are single bonds, A₁ is pyrimidine-2,5-diyl, A₂ and A₃ are 1,4-phenylene, which may be substituted by at least one substituent selected from the group consisting of F, Cl, Br, CH₃, CF₃ and CN;

(Iad) an optically active compound in which A₄ and X₁ are single bonds, A₁ and A₂ are respectively groups selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl and indane-2,5-diyl, each of which may be substituted by at least one substituent selected from the group consisting of F, Cl, Br, CH₃, CF₃ and CN, and A₃ is 1,4-phenylene, which may be substituted by at least one substituent selected from the group consisting of F, Cl, Br, CH₃, CF₃ and CN;

(Iba) an optically active compound in which A₁, A₂, A₄ and X₁ are respectively single bonds, A₃ is a group selected from the group consisting of pyridine-2,5-diyl, 1,4-cyclohexylene, quinoxaline-2,6-diyl, quinoline-2,6-diyl and 2,6-naphthylene;

(Ibb) an optically active compound in which A₁, A₄ and X₁ are single bonds, A₂ is 1,4-phenylene, which may be substituted by at least one substituent selected from the group consisting of F, Cl, Br, CH₃, CF₃ and CN, and A₃ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, quinoxaline-2,6-diyl, quinoline-2,6-diyl and 2,6-naphthylene;

(Ica) an optically active compound in which A₁ and X₁ are single bonds, A₂ is groups selected from the group consisting of 1,4-phenylene, pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, each of which may be substituted by at least one substituent selected from the group consisting of F, Cl, Br, CH₃, CF₃ and CN, and A₃ and A₄ are 1,4-phenylene, which may be substituted by at least one substituent selected from the group consisting of F, Cl, Br, CH₃, CF₃ and CN;

(Ida) an optically active compound in which A₁ and X₁ are single bonds, A₃ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, A₂ and A₄ are 1,4-phenylene, which may be substituted by at least one substituent selected from the group consisting of F, Cl, Br, CH₃, CF₃ and CN; and (Idb) an optically active compound in which A₁, A₂ and X₁ are single bonds, A₃ is a group selected from the group consisting of 1,4-phenylene, pyridine-2,5-diyl, 1,4-cyclohexylene, quinoxaline-2,6-diyl, quinoline-2,6-diyl and 2,6-naphthylene, and A₄ is 1,4-phenylene, which may be substituted by at least one substituent selected from the group consisting of F, Cl, Br, CH₃, CF₃ and CN.

4. An optically active compound according to claim 1, wherein R₁ is selected from the group consisting of:

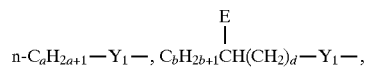

73
-continued

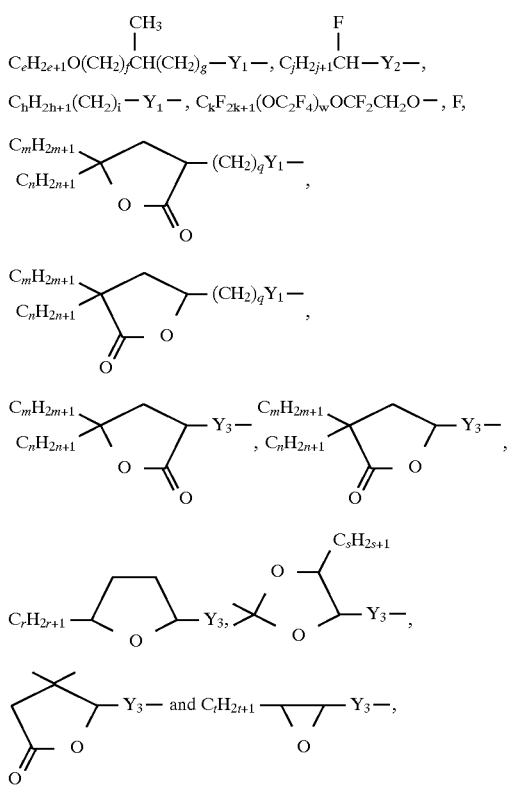

and R$_2$ is selected from the group consisting of:

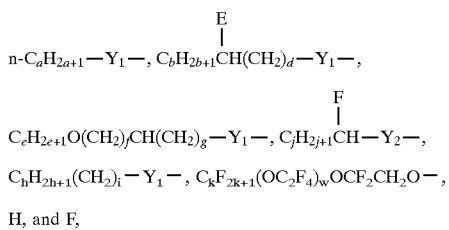

H, and F, where a is an integer from 1 to 16; d, g and i are independently integers from 0 to 7; b, e, h, j and k are independently integers from 1 to 10; f and w are independently 0 or 1; m, n, q, r, s and t are independently integers from 0 to 10 in which b+d≦16, e+f+g≦16 and h+i≦16; E is CH$_3$ or CF$_3$; Y$_1$ is a single bond, —O—, —COO— or —OCO—; Y$_2$ is —COO—, —CH$_2$O, —CH$_2$CH$_2$O—, —CH$_2$CH$_2$CH$_2$O— or —CH$_2$CH$_2$—; and Y$_3$ is a single bond, —COO—, CH$_2$O—, —OCO— or —OCH$_2$— which may be optically active groups.

5. An optically active compound according to claim 1, wherein p of said optically active compound represented by general formula (I) is an integer from 2 to 12.

6. An optically active compound according to claim 1, wherein p of said optically active compound represented by general formula (I) is 2, 4, 6 or 8.

7. An optically active compound according to claim 1 wherein p of said optically active compound represented by general formula (I) is 3, 5, 7 or 9.

8. An optically active compound comprising a structure represented by the following general formula (I'):

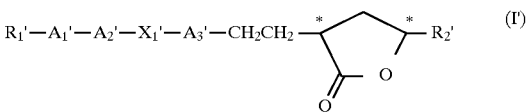

where R$_1$' is H, F, CN or a straight, branched alkyl group (one or more —CH$_2$— in the alkyl group may be replaced by —O—, —S—, —CO—, —CH(CN)—, —CH=CH— or —C≡C— under condition that heteroatoms do not position adjacent and the hydrogen atom in the alkyl group may be replaced by a fluorine atom) or cyclic alkyl group wherein the cyclic alkyl is a 3–6 membered heterocyclic ring having 1 or 2 oxygen heteroatoms, wherein 1 or 2 non-adjacent —CH$_2$— moieties is optionally replaced with —CO—, said heterocyclic ring being optionally substituted by at least one alkyl group having 1 to 20 carbon atoms; R$_2$' is a straight or branched alkyl group (one or more —CH$_2$— in the alkyl group may be replaced by —O—, —CO—, or —CH=CH— under condition that heteroatoms do not position adjacent and the hydrogen atom in the alkyl group may be replaced by a fluorine atom) having 1 to 20 carbon atoms; A$_3$' is a group selected from the group consisting of 1,4-phenylene, pyridine-2,5-diyl, pyrimidine-2,5-diyl, pyrazine-2,5-diyl, pyridazine-3,6-diyl, 1,4-cyclohexylene, 1,3-dioxane-2,5-diyl, 1,3-ditiane-2,5-diyl, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2,6-diyl, quinoxaline-2,6-diyl, quinoline-2,6-diyl, 2,6-naphthylene, indane-2,5-diyl, 2-alkylindane-2,5-diyl (the alkyl group is a straight chain or branched alkyl group having 1 to 18 carbon atoms), indanone-2,6-diyl, 2-alkylindane-2,6-diyl (the alkyl group is a straight chain or branched alkyl group having 1 to 18 carbon atoms), coumarane-2,5-diyl and 2-alkylcoumarane-2,5-diyl (the alkyl group is a straight chain or branched alkyl group having 1 to 18 carbon atoms), each of which may be substituted by at least one substituent selected from the group consisting of F, Cl, Br, CH$_3$, CF$_3$ and CN; A$_1$' and A$_2$' are single bonds or selected from A$_3$'; X$_1$' is a single bond, —COO—, —OCO—, —CH$_2$O—, —OCH$_2$—, —CH$_2$CH$_2$—, —CH=CH— or —C≡C—; and * represents optically active characteristic.

9. An optically active compound according to claim 8, wherein said optically active compound represented by general formula (I') is any of materials in (Ia') or (Ib'):

(Ia') an optically active compound in which A$_1$' and A$_2$' are single bonds or groups selected from the group consisting of 1,4-phenylene, pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl, each of which may be substituted by at least one substituent selected from the group consisting of F, Cl, Br, CH$_3$, CF$_3$ and CN and A$_3$ is 1,4-phenylene substituted by at least one group selected from the group consisting of F, Cl, Br, CH$_3$, CF$_3$ and CN and A$_4$ is a single bond; or (Ib') an optically active compound in which A$_1$' and A$_2$' are single bonds or 1,4-phenylene, which may be substitutes by at least one substituent selected from the group consisting of F, Cl, Br, CH$_3$, CF$_3$ and CN, A$_3$ is a group selected from the group consisting of pyridine-2,5-diyl, pyrimidine-2,5-diyl, pyrazine-2,5-diyl, pyridazine-3,6-diyl, 1,4-cyclohexylene, thiophene-2,5-diyl, thiazole-2,5-diyl, thiaziazole-2,5-diyl, benzoxazole-2,5-diyl, benzoxazole-2,6-diyl, benzothiazole-2,5-diyl, benzothiazole-2,6-diyl, benzofuran-2,5-diyl, benzofuran-2-6-diyl, quinoxaline-2,6-diyl, quinoline-2,6-diyl, 2,6-naphthylene, indane-2,5-diyl and coumarane-2,5-diyl.

10. An optically active compound according to claim 8, wherein said optically active compound represented by general formula (I') is any of materials in (Iaa') or (Ibb'):

(Iaa') an optically active compound in which $A_1'$, $A_2'$ and $X_1'$ are single bonds and $A_3'$ is 1,4-phenylene, which may be substituted by at least one substituent selected from the group consisting of F, Cl, Br, $CH_3$, $CF_3$ and CN;

(Iab') an optically active compound in which $A_1'$ is a single bond and both $A_2'$ and $A_3'$ are 1,4-phenylene, which may be at least one substituent selected from the group consisting of F, Cl, Br, $CH_3$, $CF_3$ and CN;

(Iac') an optically active compound in which $A_1'$ and $X_1'$ are single bonds, $A_2'$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, benzothiazole-2,6-diyl, quinoxaline-2,6-diyl, quinoline-2,6-diyl, 2,6-naphthylene and indane-2,5-diyl, $A_3'$ is 1,4-phenylene, which may be substituted by at least one substituent selected from the group consisting of F, Cl, Br, $CH_3$, $CF_3$ and CN; and (Iba') an optically active compound in which $A_1'$, $A_2'$ and $X_1'$ are single bonds and $A_3'$ is a group selected from the group consisting of pyridine-2,5-diyl, 1,4-cyclohexylene, quinoxaline-2,6-diyl, quinoline-2,6-diyl and 2,6-naphthylene (Ibb') An optically active compound in which $A_1'$ and $X_1'$ are single bonds, $A_2'$ is 1,4-phenylene, which may be substituted by at least one substituent selected from the group consisting of F, Cl, Br, $CH_3$, $CF_3$ and CN and $A_3'$ is a group selected from the group consisting of pyridine-2,5-diyl, pyrimidine-2,5-diyl, 1,4-cyclohexylene, thiophene-2,5-diyl, thiazole-2,5-diyl, thiaziazole-2,5-diyl, quinoxaline-2,6-diyl, quinoline-2,6-diyl and 2,6-naphthylene.

11. An optically active compound according to claim 8, wherein R1' and R2' of said optically active compound represented by general formula (I') respective are any of materials in (i') to (v'):

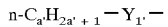  (i')

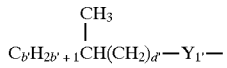  (ii')

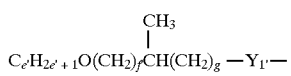  (iii')

where a' is an integer from 1 to 16, d', g' and i' respectively are integers from 0 to 7, b', e', h' and j' respectively are integers from 1 to 10, f' is 0 or 1 in which b'+d'≦16, e'+f'+g'≦16 and h'+i'≦16 are satisfied, Y1' is a single bond, —O—, —COO— or —OCO— and $Y_2'$ is —COO— or —$CH_2O$—, which may be optically active.

12. A liquid crystal composition comprising one or more kinds of said optically active compounds claimed in any of claims 1–11.

13. A liquid crystal composition according to claim 12, wherein said optically active compound is contained by 1 wt % to 80 wt %.

14. A liquid crystal composition according to claim 12, wherein said optically active compound is contained by 1 wt % to 60 wt %.

15. A liquid crystal composition according to claim 12, wherein said optically active compound is contained by 1 wt % to 40 wt %.

16. A liquid crystal composition according to claim 12, wherein said liquid crystal compound has a chiral smectic phase.

17. A liquid crystal composition according to claim 12, wherein two or more kinds of said optically active compounds.

18. A liquid crystal device comprising said liquid crystal composition according to claim 16 disposed between a pair of electrode substrates.

19. A liquid crystal device according to claim 18, wherein an orientation control layer is further formed on said electrode substrate.

20. A liquid crystal device according to claim 18, wherein said orientation control layer is a layer subjected to a rubbing process.

21. A liquid crystal device according to claim 18, wherein said pair of electrode substrates are disposed with a thickness realized when spirals of liquid crystal molecules are untied.

22. A liquid crystal apparatus comprising said liquid crystal device according to claim 18 and a circuit for operating said liquid crystal device.

23. A liquid crystal apparatus according to claim 22, wherein said liquid crystal device is used as a display device.

24. A liquid crystal apparatus according to claim 23 further comprising a light source.

25. A display method comprising the step of:
selecting a liquid crystal device according to claim 22; and
controlling said liquid crystal composition to display information.

* * * * *

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

Page 1 of 10

It is certified that error appears in the above-identified patent and that said Letters Patent is hereby corrected as shown below:

TITLE PAGE:

[56] REFERENCES CITED

Foreign Patent Documents
"2138274" should read --2-138274--.
"2138385" should read --2-138385--.
"2261893" should read --2-261893--.
"2286673" should read --2-286673--.
"2289561" should read --2-289561--.
"3052882" should read --3-052882--.
"3058981" should read --3-058981--.
"3173878" should read --3-173878--.
"3173879" should read --3-173879--.
"4193872" should read --4-193872--.
"4272989" should read --4-272989--.
"4334376" should read --4-334376--.

COLUMN 2

Line 33, "being" should be deleted.

COLUMN 4

Line 19, "liquid crystal" (second occurrence) should be deleted.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 8

Line 64, "$-CH_2O-O,$" should read ---$CH_2O-$,--.

COLUMN 9

Line 48, "hetero atoms" should read --heteroatoms--.
Line 58, "alkylindane-2,5-diyl" should read --2-alkylindane-2,5-diyl--.

COLUMN 11

Line 32, "a olefin" should read --an olefin--.

COLUMN 17

Table 1 Continued, No. 113, "Pu" should read --Ph--.

COLUMN 19

Table 1 Continued, No. 176, "$C_5H_{13}$" should read --$C_6H_{13}$--.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 23

Table 1 Continued, No. 332, "$C_6H_{13}{}^1(CF_3)CH_2O$" should read --$C_6H_{13}{}^1CH(CF_3)CH_2O$

COLUMN 25

Table 1 Continued, No. 402, "402" (second occurrence) should read --403--.
No. 404, "$C_5H_{13}$" should read --$C_6H_{13}$--.
No. 429, "$C_5H_{13}$" should read --$C_6H_{13}$--.

COLUMN 27

Table 1 Continued, No. 502, "La1(0,5)-(CH2)4" should read --La1(0,6)-$(CH_2)4$--.
Line 43, "is" should read --are--.
Line 51, "$R_2$ is" (second occurrence) should be deleted.
Line 61, "R2" should read --$R_2$--.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 32

Line 1, "respective" should read --respectively--.
   Line 2, "respective" should read --respectively--.

COLUMN 33

Line 62, "liquid crystal" (second occurrence) should be deleted.

COLUMN 34

Line 40, "arbitrary" should read --an arbitrary--.

COLUMN 35

Line 6, "understand" should read --understood--.

COLUMN 36

Line 55, "wit" should read --with--.

COLUMN 37

Line 10, "2,59g" should read --2.59g--.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 39

Line 42, "(developing, solvent:" should read
--(developing solvent:--.

COLUMN 50

Line 35, "acetate 10/1)" should read --acetate=10/1)--.

COLUMN 51

Line 52, "acetate 10/1)" should read --acetate=10/1)--.

COLUMN 52

Line 44, "$C_9H_{19}$-Py2-Ph-$OC_{10}H_{17}$" should read
--$C_9H_{19}$-Py2-Ph-$OC_8H_{17}$--.

COLUMN 53

Line 49, "liquid crystal" (second occurrence) should be deleted.
Line 53, "are" should be deleted.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 54

Line 5, "liquid crystal" (second occurrence) should be deleted.
Line 9, "are" should be deleted.
Line 27, "liquid crystal" (second occurrence) should be deleted.
Line 31, "are" should be deleted.
Line 49, "liquid crystal" (second occurrence) should be deleted.
Line 53, "are" should be deleted.

COLUMN 57

Line 6, "$C_8H_{17}-Pr1-Ph-(CH_2)5-L1-C_8H_{17}$" should read --$C_8H_{17}-Pr1-Ph-(CH_2)_5-L1-C_8H_{17}$--.

COLUMN 58

Line 11, "$C_4H_9-CH_2O-Ph-Py1-C_6H_{13}$" should read --$C_4H_9-Cy-CH_2O-Ph-Py1-C_6H_{13}$--.

UNITED STATES PATENT AND TRADEMARK OFFICE
CERTIFICATE OF CORRECTION

PATENT NO.  : 5,849,217

DATED       : December 15, 1998

INVENTOR(S) : SHINICHI NAKAMURA ET AL.

It is certified that error appears in the above-identified patent and that said Letters Patent is hereby corrected as shown below:

COLUMN 60

Line 62, "Constitutinoal Formula" should read
    --Constitutional Formula--.

COLUMN 61

Line 2, "Constitutinoal Formula" should read
    --Constitutional Formula--.
  Line 5, "$C_5H_{11}$-Py2-Ph-Ph-$C_6H_{15}$" should read
    --$C_5H_{11}$-Py2-Ph-Ph-$C_6H_{13}$--.
  Line 58, "follows." should read --follows;--.

COLUMN 64

Line 19, "SiO2" should read --$SiO_2$--.
  Line 52, "$C_8H_{11}$-Cy-COO-Ph-Py1-$C_{12}H_{25}$" should read
    --$C_5H_{11}$-Cy-COO-Ph-Py1-$C_{12}H_{25}$--.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 68

Line 8, "$C_{10}H_{21}$-Py2-Ph-$(CH_1)2$-L1-$C_6H_{13}$" should read --$C_{10}H_{21}$-Py2-Ph-$(CH_2)_2$-L1-$C_6H_{13}$--.
Line 36, "as prepared." should read --was prepared.--.

COLUMN 69

Line 49, "making using" should read --making use--.
Line 54, "in dependency" should read --independency--.
Line 64, "the combination" should read --that recombination--.

COLUMN 70

Line 5, "chain," should read --chain or--.
Line 9, "atom" should read --atoms--.
Line 20, "atom" should read --atoms--.
Line 39, "$X_1+$" should read --$X_1$--.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 71

Lines 62-63, "or that having one or two substituents" should be deleted.

COLUMN 72

Line 31, "groups" should read --a group--.

COLUMN 74

Line 66, "substitutes" should read --substituted--.

COLUMN 75

Line 31, "and" (second occurrence) should be deleted.
Line 37, "2,6-naphthylene(Ibb')" should read
--2,6-naphthylene; and ¶ (Ibb')--.
Line 48, "respective" should be deleted.

UNITED STATES PATENT AND TRADEMARK OFFICE
CERTIFICATE OF CORRECTION

PATENT NO. : 5,849,217

DATED : December 15, 1998

INVENTOR(S) : SHINICHI NAKAMURA ET AL.

It is certified that error appears in the above-identified patent and that said Letters Patent is hereby corrected as shown below:

COLUMN 76

Line 32, "claim 16" should read --claim 12--.
Line 51, "step" should read --steps--.
Line 52, "claim 22," should read --claim 18--.

Signed and Sealed this

Twenty-third Day of November, 1999

Q. TODD DICKINSON

Attest:

Attesting Officer    Acting Commissioner of Patents and Trademarks